US00RE44613E

(19) United States
(12) Reissued Patent
Duffy et al.

(10) Patent Number: US RE44,613 E
(45) Date of Reissued Patent: Nov. 26, 2013

(54) N-SUBSTITUTED GLYCINE DERIVATIVES: HYDROXYLASE INHIBITORS

(75) Inventors: Kevin J. Duffy, Collegeville, PA (US); William Henry Miller, Collegeville, PA (US); Andrea K. Myers, Collegeville, PA (US); Antony N. Shaw, King of Prussia, PA (US); Michael N. Zimmerman, Collegeville, PA (US)

(73) Assignee: GlaxoSmithKline LLC, Philadelphia, PA (US)

(21) Appl. No.: 13/281,965

(22) Filed: Oct. 26, 2011

Related U.S. Patent Documents

Reissue of:
(64) Patent No.: 7,608,621
Issued: Oct. 27, 2009
Appl. No.: 11/972,702
Filed: Jan. 11, 2008

U.S. Applications:
(60) Provisional application No. 60/884,710, filed on Jan. 12, 2007.

(51) Int. Cl.
*A01N 43/58* (2006.01)
*A61K 31/50* (2006.01)

(52) U.S. Cl.
USPC ..... 514/247; 544/240

(58) Field of Classification Search
USPC ..... 544/240; 514/247
See application file for complete search history.

(56) References Cited

U.S. PATENT DOCUMENTS

| | | | | |
|---|---|---|---|---|
| 5,620,995 | A | 4/1997 | Weidmann et al. | |
| 5,658,933 | A | 8/1997 | Weidmann et al. | |
| 6,605,625 | B2 | 8/2003 | Peukert et al. | |
| 6,972,296 | B2 * | 12/2005 | Biediger et al. | 514/349 |
| 2001/0007869 | A1 | 7/2001 | Bare et al. | |
| 2003/0153503 | A1 | 8/2003 | Klaus et al. | |
| 2004/0063709 | A1 | 4/2004 | Taveras et al. | |
| 2005/0020487 | A1 | 1/2005 | Klaus et al. | |
| 2006/0276477 | A1 | 12/2006 | Klaus et al. | |
| 2007/0249550 | A1 | 10/2007 | Sitkovsky | |
| 2007/0292433 | A1 | 12/2007 | Seeley et al. | |
| 2007/0293575 | A1 | 12/2007 | Seeley et al. | |
| 2010/0003190 | A1 | 1/2010 | Kolyada et al. | |

FOREIGN PATENT DOCUMENTS

| | | |
|---|---|---|
| WO | 03/088917 | 10/2003 |
| WO | 2006/048330 | 5/2006 |
| WO | 2008/013838 | 1/2008 |
| WO | 2008/040002 | 4/2008 |
| WO | 2009/142732 | 11/2009 |

OTHER PUBLICATIONS

Nemeth, Advances in Hematology, 2012, Article ID 750643, 9 pages.*
Haase, Am. J. Physiol. Renal Physiol. 291: F271-F281, 2006.*
Kaelin, Biochem. & Biophys. Research Commun., 338 (2005) 627-638.*
M.A. Goldberg et al., 84 PNAS, 7972-7976 (1987).*
Y. Setoguchi et al., 84 Blood, 2946-2953 (1994).*
V. Bardet et al., 12 Liver Transplantation 1649-1654 (2006).*
I.C. Macdougall, Seminars in Nephrology, 313-318 (2006).*
Auerbach et al, 22 Journal of Clinical Oncology 1301-1307 (2004).*
Mikhail et al., "Stimulating Erythropoiesis: Future Perspectives," Kidney Blood Press. Res., 2008, 31(4), pp. 234-246.
Mikhail, et al., Kidney & Blood Pressure Research, 2008;31:234-246.*

* cited by examiner

*Primary Examiner* — James O Wilson
*Assistant Examiner* — Alexander R Pagano
(74) *Attorney, Agent, or Firm* — Kathryn L. Coulter; Tony W. Peng

(57) ABSTRACT

The invention described herein relates to certain pyridazinedione N-substituted glycine derivatives of formula (I)

(I)

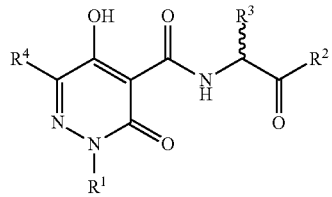

which are antagonists of HIF prolyl hydroxylases and are useful for treating diseases benefiting from the inhibition of this enzyme, anemia being one example.

24 Claims, No Drawings

N-SUBSTITUTED GLYCINE DERIVATIVES: HYDROXYLASE INHIBITORS

Matter enclosed in heavy brackets [ ] appears in the original patent but forms no part of this reissue specification; matter printed in italics indicates the additions made by reissue.

*CROSS REFERENCE TO RELATED APPLICATIONS*

*This application is a reissue application of U.S. application Ser. No. 11/972,702, filed Jan. 11, 2008, now U.S. Pat. No. 7,608,621, which claims the benefit of U.S. Provisional Application No. 60/884,710, filed Jan. 12, 2007.*

FIELD OF THE INVENTION

This invention relates to certain heteroaromatic N-substituted glycine derivatives that are inhibitors of HIF prolyl hydroxylases, and thus have use in treating diseases benefiting from the inhibition of this enzyme, anemia being one example.

BACKGROUND OF THE INVENTION

Anemia occurs when there is a decrease or abnormality in red blood cells, which leads to reduced oxygen levels in the blood. Anemia occurs often in cancer patients, particularly those receiving chemotherapy. Anemia is often seen in the elderly population, patients with renal disease, and in a wide variety of conditions associated with chronic disease.

Frequently, the cause of anemia is reduced erythropoietin (Epo) production resulting in prevention of erythropoiesis (maturation of red blood cells). Epo production can be increased by inhibition of prolyl hydroxylases that regulate hypoxia inducible factor (HIF).

One strategy to increase erythropoietin (Epo) production is to stabilize and thus increase the transcriptional activity of the HIF. HIF-alpha subunits (HIF-1alpha, HIF-2alpha, and HIF-3alpha) are rapidly degraded by proteosome under normoxic conditions upon hydroxylation of proline residues by prolyl hydroxylases (EGLN1, 2, 3). Proline hydroxylation allows interaction with the von Hippel Lindau (VHL) protein, a component of an E3 ubiquitin ligase. This leads to ubiquitination of HIF-alpha and subsequent degradation. Under hypoxic conditions, the inhibitory activity of the prolyl hydroxylases is suppressed, HIF-alpha subunits are therefore stabilized, and HIF-responsive genes, including Epo, are transcribed. Thus, inhibition of prolyl hydroxylases results in increased levels of HIF-alpha and thus increased Epo production.

The compounds of this invention provide a means for inhibiting these hydroxylases, increasing Epo production, and thereby treating anemia. Ischemia, stroke, and cytoprotection may also benefit by administering these compounds.

SUMMARY OF THE INVENTION

In the first instance, this invention relates to a compound of formula (I):

(I)

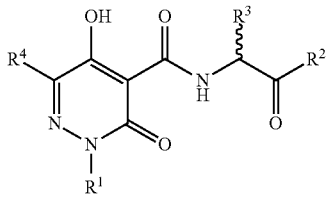

wherein:

$R^1$ is selected from the group consisting of hydrogen, —$NR^5R^6$, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^4$ is selected from the group consisting of hydrogen, $COOR^9$, $CONR^7R^8$, —$NR^5R^6$, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^2$ is $NR^7R^8$ or —$OR^9$;

$R^3$ is H or $C_1$-$C_4$alkyl;

$R^5$ and $R^6$ are each independently selected from the group consisting of hydrogen, $C_1$-$C_{10}$ alkyl, $C_3$-$C_8$cycloalkyl, $C_1$-$C_{10}$ alkyl-$C_3$-$C_8$cycloalkyl, $C_3$-$C_8$heterocycloalkyl, $C_1$-$C_{10}$ alkyl-$C_3$-$C_8$heterocycloalkyl, aryl, $C_1$-$C_{10}$alkyl-aryl, heteroaryl, $C_1$-$C_{10}$alkyl-heteroaryl, —CO($C_1$-$C_4$ alkyl), —CO($C_3$-$C_6$ cycloalkyl), —CO($C_3$-$C_6$ heterocycloalkyl), —CO(aryl), —CO(heteroaryl), and —$SO_2$($C_1$-$C_4$ alkyl); or $R^5$ and $R^6$ taken together with the nitrogen to which they are attached form a 5- or 6- or 7-membered saturated ring optionally containing one other heteroatom selected from the group consisting of oxygen, nitrogen and sulphur;

$R^7$ and $R^8$ are each independently selected from the group consisting of hydrogen, $C_1$-$C_{10}$ alkyl, $C_2$-$C_{10}$ alkenyl, $C_2$-$C_{10}$ alkynyl, $C_3$-$C_8$ cycloalkyl, $C_3$-$C_8$ heterocycloalkyl, aryl and heteroaryl;

$R^9$ is H or a cation, or $C_1$-$C_{10}$alkyl which is unsubstituted or substituted with one or more substituents independently selected from the group consisting of $C_3$-$C_6$ cycloalkyl, heterocycloalkyl, aryl, and heteroaryl; and wherein any carbon or heteroatom of $R^1$, $R^2$, $R^3$, $R^4$, $R^5$, $R^6$, $R^7$, $R^8$, $R^9$ is unsubstituted or, where possible, is substituted with one or more substituents independently selected from the group consisting of $C_1$-$C_6$ alkyl, aryl, heteroaryl, halogen, —$OR^{10}$, $NR^5R^6$, cyano, nitro, —C(O)$R^{10}$, —C(O)O$R^{10}$, —S$R^{10}$, —S(O)$R^{10}$, —S(O)$_2$ $R^{10}$, —$NR^5R^6$, —$CONR^5R^6$, —N($R^5$)C(O)$R^{10}$, —N($R^5$)C(O)O$R^{10}$, —OC(O)$NR^5R^6$, —N($R^5$)C(O)$NR^5R^6$, —$SO_2NR^5R^6$, —N($R^5$)$SO_2R^{10}$, $C_1$-$C_{10}$alkenyl, $C_1$-$C_{10}$alkynyl, $C_3$-$C_6$ cycloalkyl, $C_3$-$C_6$ heterocycloalkyl, aryl and heteroaryl group; wherein $R^5$ and $R^6$ are the same as defined above and $R^{10}$ is hydrogen, $C_1$-$C_{10}$alkyl, $C_2$-$C_{10}$alkenyl, $C_2$-$C_{10}$alkynyl, —CO($C_1$-$C_4$ alkyl), —CO(aryl), —CO(heteroaryl), —CO($C_3$-$C_6$ cycloalkyl), —CO($C_3$-$C_6$ heterocycloalkyl), —$SO_2$($C_1$-$C_4$ alkyl), $C_3$-$C_8$ cycloalkyl, $C_3$-$C_8$heterocycloalkyl, $C_6$-$C_{14}$ aryl, $C_1$-$C_{10}$alkyl-aryl, heteroaryl, or $C_1$-$C_{10}$alkyl-heteroaryl;

or a pharmaceutically acceptable salt or solvate thereof.

In a second aspect of the present invention, there is provided a compound of formula (I) or a salt or solvate thereof for use in mammalian therapy, e.g. treating amenia. An example of this therapeutic approach is that of a method for treating anemia caused by increasing the production of erythropoietin (Epo) by inhibiting HIF prolyl hydroxylases comprising administering a compound of formula (I) to a patient in need thereof, neat or admixed with a pharmaceutically acceptable excipient, in an amount sufficient to increase production of Epo.

In a third aspect of the present invention, there is provided a pharmaceutical composition comprising a compound of formula (I) or a salt, solvate, or the like thereof, and one or more of pharmaceutically acceptable carriers, diluents and excipients.

In a fourth aspect, there is provided the use of a compound of formula (I) or a salt or solvate thereof in the preparation of a medicament for use in the treatment of a disorder mediated by inhibiting HIF prolyl hydroxylases, such as an anemia, that can be treated by inhibiting HIF prolyl hydroxylases.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_4$ alkyl" and "$C_1$-$C_{10}$ alkyl" refers to an alkyl group having at least 1 and up to 4 or 10 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, n-octyl, n-nonyl, and n-decyl, and branched analogs of the latter 5 normal alkanes.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethenylene) and propynyl (or propenylene).

When "cycloalkyl" is used it refers to a non-aromatic, saturated, cyclic hydrocarbon ring containing the specified number of carbon atoms. So, for example, the term "$C_3$-$C_8$ cycloalkyl" refers to a non-aromatic cyclic hydrocarbon ring having from three to eight carbon atoms. Exemplary "$C_3$-$C_8$ cycloalkyl" groups useful in the present invention include, but are not limited to, cyclopropyl, cyclobutyl, cyclopentyl, cyclohexyl, cycloheptyl and cyclooctyl.

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "$C_3$-$C_8$ heterocycloalkyl" is used, it means a non-aromatic heterocyclic ring containing the specified number of ring atoms being, saturated or having one or more degrees of unsaturation and containing one or more heteroatom substitutions selected from O, S and/or N. Such a ring may be optionally fused to one or more other "heterocyclic" ring(s) or cycloalkyl ring(s). Examples of "heterocyclic" moieties include, but are not limited to, aziridine, thiirane, oxirane, azetidine, oxetane, thietane, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

"Aryl" refers to optionally substituted monocyclic and polycarbocyclic unfused or fused groups having 6 to 14 carbon atoms and having at least one aromatic ring that complies with Hückel's Rule. Examples of aryl groups are phenyl, biphenyl, naphthyl, anthracenyl, phenanthrenyl and the like.

"Heteroaryl" means an optionally substituted aromatic monocyclic ring or polycarbocyclic fused ring system wherein at least one ring complies with Hückel's Rule, has the specified number of ring atoms, and that ring contains at least one heteratom selected from N, O, and/or S. Examples of "heteroaryl" groups include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl.

The term "optionally" means that the subsequently described event(s) may or may not occur, and includes both event(s), which occur, and events that do not occur.

The term "solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxy-ethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

A group of compounds of particular interest are those wherein:

$R^1$ is selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^4$ is selected from the group consisting of hydrogen, $COOR^9$, $CONR^7R^8$, —$NR^5R^6$, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^2$ is —$NR^7R^8$, —$OR^9$;

$R^3$ is H or $C_1$-$C_4$alkyl;

$R^9$ is H or a cation, or $C_1$-$C_{10}$alkyl which is unsubstituted or substituted with one or more substituents independently selected from the group consisting of $C_3$-$C_6$ cycloalkyl, heterocycloalkyl, aryl, and heteroaryl; and wherein any carbon or heteroatom of $R^1$, $R^2$, $R^3$, $R^4$, $R^9$ is unsubstituted or, where possible, is substituted with one or more substituents independently selected from the group consisting of $C_1$-$C_6$ alkyl, aryl, heteroaryl, halogen, —$OR^{10}$, —$NR^5R^6$, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, $OC(O)NR^5R^6$, $N(R^5)C(O)NR^5R^6$, —$SO_2NR^5R^6$, —$N(R^5)SO_2R^{10}$, $C_1$-$C_{10}$ alkenyl, $C_1$-$C_{10}$ alkynyl, $C_3$-$C_6$ cycloalkyl, $C_3$-$C_6$ heterocycloalkyl, aryl and heteroaryl group, wherein $R^5$, and $R^6$ are the same as defined above and $R^{10}$ is hydrogen, $C_1$-$C_{10}$alkyl, $C_2$-$C_{10}$alkenyl, $C_2$-$C_{10}$alkynyl, —$CO(C_1$-$C_4$ alkyl), —CO(aryl), —CO(heteroaryl), —$CO(C_3$-$C_6$ cycloalkyl), —$CO(C_3$-$C_6$ heterocycloalkyl), —$SO_2(C_1$-$C_4$ alkyl), $C_3$-$C_8$ cycloalkyl, $C_3$-$C_8$heterocycloalkyl, $C_6$-$C_{14}$ aryl, $C_1$-$C_{10}$alkyl-aryl, heteroaryl, or $C_1$-$C_{10}$alkyl-heteroaryl;

or a pharmaceutically acceptable salt or solvate thereof.

Another group of compounds of particular interest are those wherein:

$R^1$ is selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^4$ is selected from the group consisting of hydrogen, $COOR^9$, $CONR^7R^8$, —$NR^5R^6$, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^2$ is —$NR^7R^8$, —$OR^9$;

$R^3$ is H;

$R^9$ is H or a cation;

wherein any carbon or heteroatom of $R^1$, $R^2$, $R^3$, $R^4$ is unsubstituted or, where possible, is substituted with one or more substituents independently selected from $C_1$-$C_6$ alkyl, aryl, heteroaryl, halogen, —$OR^{10}$, —$NR^5R^6$, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, —$OC(O)NR^5R^6$, —$N(R^5)C(O)NR^5R^6$, —$SO_2NR^5R^6$, —$N(R^5)SO_2R^{10}$, $C_1$-$C_{10}$ alkenyl, $C_1$-$C_{10}$ alkynyl, $C_3$-$C_6$ cycloalkyl, $C_3$-$C_6$ heterocycloalkyl, aryl or heteroaryl group, wherein $R^5$, and $R^6$ are the same as defined above and $R^{10}$ is hydrogen, $C_1$-$C_{10}$alkyl, $C_2$-$C_{10}$alkenyl, $C_2$-$C_{10}$alkynyl, —$CO(C_1$-$C_4$ alkyl), —CO(aryl), —CO(heteroaryl), —$CO(C_3$-$C_6$ cycloalkyl), —$CO(C_3$-$C_6$ heterocycloalkyl), —$SO_2(C_1$-$C_4$ alkyl), $C_3$-$C_8$ cycloalkyl, $C_3$-$C_8$heterocycloalkyl, $C_6$-$C_{14}$ aryl, $C_1$-$C_{10}$alkyl-aryl, heteroaryl, and $C_1$-$C_{10}$alkyl-heteroaryl;

or a pharmaceutically acceptable salt thereof.

Another group of compounds of particular interest are those wherein:

$R^1$ is selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^4$ is selected from the group consisting of hydrogen, $COOR^9$, $CONR^7R^8$, —$NR^5R^6$, $C_1$-$C_{10}$alkyl, $C_2$-$C_{10}$alkenyl, $C_2$-$C_{10}$alkynyl, $C_3$-$C_8$cycloalkyl, $C_1$-$C_{10}$alkyl-$C_3$-$C_8$cycloalkyl, $C_5$-$C_8$cycloalkenyl, $C_1$-$C_{10}$alkyl-$C_5$-$C_8$ cycloalkenyl, $C_3$-$C_8$ heterocycloalkyl, $C_1$-$C_{10}$alkyl-$C_3$-$C_8$ heterocycloalkyl, aryl, $C_1$-$C_{10}$alkyl-aryl, heteroaryl and $C_1$-$C_{10}$alkyl-heteroaryl;

$R^2$ is —$OR^9$;

$R^3$ is H;

$R^9$ is H or a cation;

wherein any carbon or heteroatom of $R^1$, $R^4$ is unsubstituted or, where possible, is substituted with one or more substituents independently selected from $C_1$-$C_6$ alkyl, aryl, heteroaryl, halogen, —$OR^{10}$, —$NR^5R^6$, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, —$OC(O)NR^5R^6$, —$N(R^5)C(O)NR^5R^6$, —$SO_2NR^5R^6$, —$N(R^5)SO_2R^{10}$, $C_1$-$C_{10}$ alkenyl, $C_1$-$C_{10}$ alkynyl, $C_3$-$C_6$ cycloalkyl, $C_3$-$C_6$ heterocycloalkyl, aryl or heteroaryl group, wherein $R^5$, and $R^6$ are the same as defined above and $R^{10}$ is hydrogen, $C_1$-$C_{10}$alkyl, $C_2$-$C_{10}$alkenyl, $C_2$-$C_{10}$alkynyl, —$CO(C_1$-$C_4$ alkyl), —CO(aryl), —CO(heteroaryl), —$CO(C_3$-$C_6$ cycloalkyl), —$CO(C_3$-$C_6$ heterocycloalkyl), —$SO_2(C_1$-$C_4$ alkyl), $C_3$-$C_8$ cycloalkyl, $C_3$-$C_8$heterocycloalkyl, $C_6$-$C_{14}$ aryl, $C_1$-$C_{10}$alkyl-aryl, heteroaryl, and $C_1$-$C_{10}$alkyl-heteroaryl;

or a pharmaceutically acceptable salt thereof.

Compounds of further interest are those wherein:

$R^1$ is 2-fluoro-4-bromobenzyl, 4-bromobenzyl, 4-(halophenyl)benzyl, 2-fluoro-4-(halophenyl)benzyl, 2-fluoro-4-triflurormethylbenzyl, 4-trifluorobenzyl, or 2-fluoro-4-($C_1$-$C_4$alkoxyphenyl)benzyl;

$R^2$ is OH;

$R^3$ is H;

$R^4$ is isopropyl, t-butyl or cyclohexyl; or a pharmaceutically acceptable salt thereof.

Processes for preparing the compound of formula (I) are also within the ambit of this invention. To illustrate, a process for preparing a compound of formula (I)

(I)

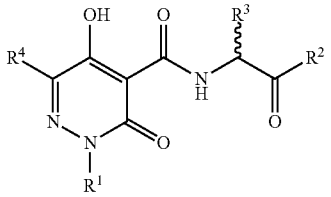

wherein $R^1$, $R^2$, $R^3$ and $R^4$ are the same as defined above for formula (I), the process comprising treating a compound of formula A:

A

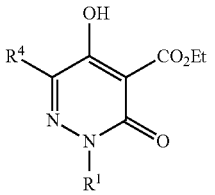

wherein $R^1$ and $R^4$ are the same as for those groups in formula (I) with an α-aminoacid sodium salt in an appropriate solvent, such as 2-methoxyethanol, under either conventional thermal conditions or by microwave irradiation, to form a compound of formula (I) where $R^2$ is —OH;

It will be appreciated by those skilled in the art that the compounds of formula (I) may exist in one or more tautomeric forms such as:

(IA)

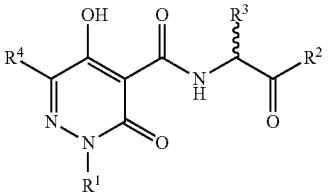

(IB)

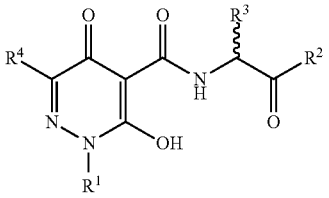

-continued (IC)

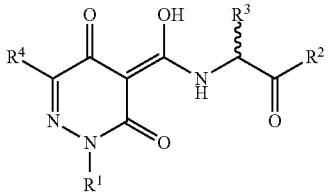

(ID)

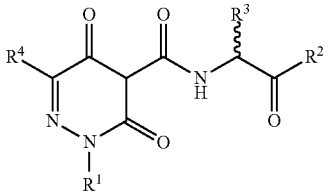

All tautomeric forms of the compounds described herein, including mixtures thereof, are intended to be encompassed within the scope of the invention. Generally, the compounds exemplified herein have been assigned names based on the structure of the tautomer of formula (IA). It should be understood that any reference to named compounds of this invention is intended to encompass all tautomers of the named compounds and any mixtures of tautomers of the named compounds.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the claimed compounds are included within the scope of the compounds of formula (I) as disclosed herein above or claimed herein below.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

DEFINITIONS rt—room temperature
DBU—1,8-diazabicyclo[5.4.0]undec-7-ene
DCM—dichloromethane
DMF—dimethylformamide
DMSO—dimethylsulfoxide
KHMDS—potassium hexamethyldisilazide
LCMS—liquid chromatography/mass spectrometry
MTBE—methyl t-butyl ether
NMR—nuclear magnetic resonance
ODS—octadecyl silyl
PTFE—polytetrafluoroethylene
RP-HPLC—reverse-phase high performance liquid chromatography
TFA—Trifluoroacetic acid
THF—tetrahydrofuran Chemical Background:

The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

Illustrated Methods of Preparation

Scheme 1

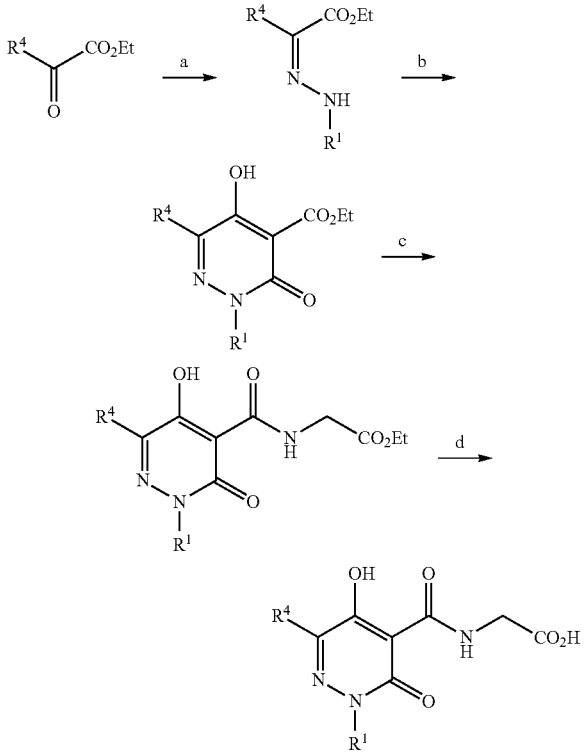

a) $R^1NHNH_2.2HCl$, $EtNPr^i_2$ or NaOAc, $CH_2Cl_2$ or $R^1NHNH_2.2HCl$, DBU, EtOH, microwave, 150° C.; b) $ClOCCH_2CO_2Et$, NaH or DBU, THF, rt or 60° C.;

c) DBU, THF or dioxane, reflux or microwave, 130° C.; d) $NaO_2CCH_2NH_2$, $MeOCH_2CH_2OH$, reflux.

Scheme 2

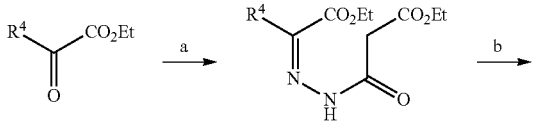

-continued

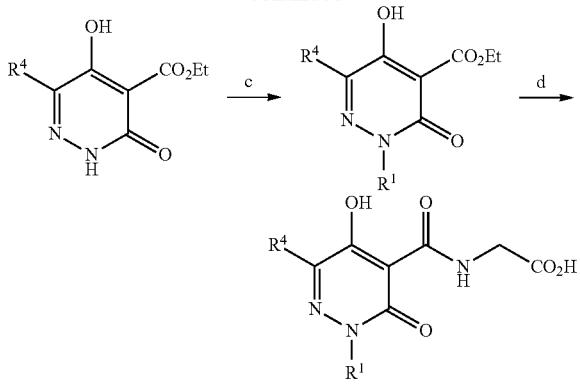

a) $EtO_2CCH_2CONHNH_2$, AcOH, $CH_2Cl_2$ or $EtO_2CCH_2CONHNH_2$, TsOH, PhMe, reflux or $EtO_2CCH_2CONHNH_2$, AcOH, EtOH, (with or without $MgSO_4$), reflux or microwave, 150° C.; b) KHMDS, $KOBu^t$ or DBU, PhMe, $Bu^tOH$ or dioxane, reflux or microwave, 150° C. or $KOBu^t$, $Bu^tOH$, microwave, 150° C.;

c) NaH, $R^1Br$, DMF, 0° C. to rt; d) $NaO_2CCH_2NH_2$, $MeOCH_2CH_2OH$ or EtOH, reflux or microwave, 150° C.

Scheme 3

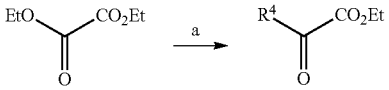

a) $R^4MgBr$ or $R^4Li$, THF or $Et_2O$, −78° C. to 0° C.

Scheme 4

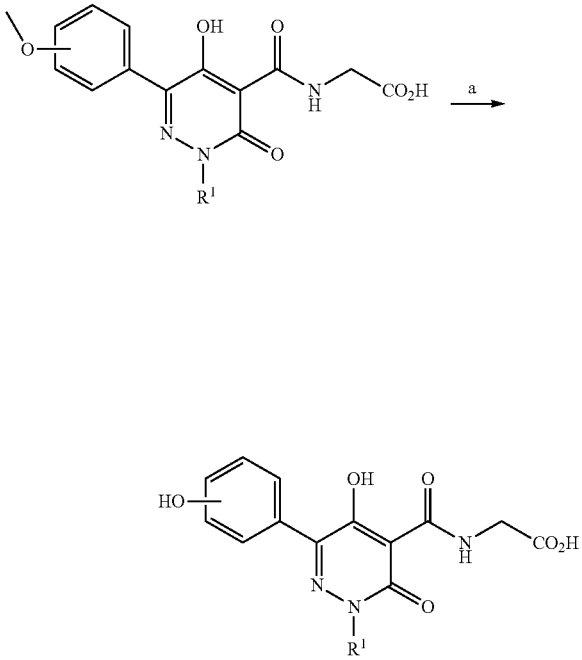

a) 48% aq HBr, AcOH, reflux

Scheme 5

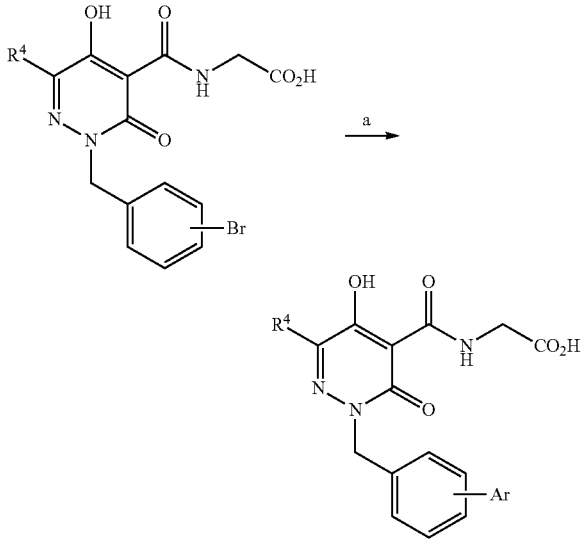

a) $ArB(OH)_2$ or $ArB(OR)_2$, $Pd(PPh_3)_4$, aq $K_2CO_3$, dioxane, microwave, 100° C.

Scheme 6

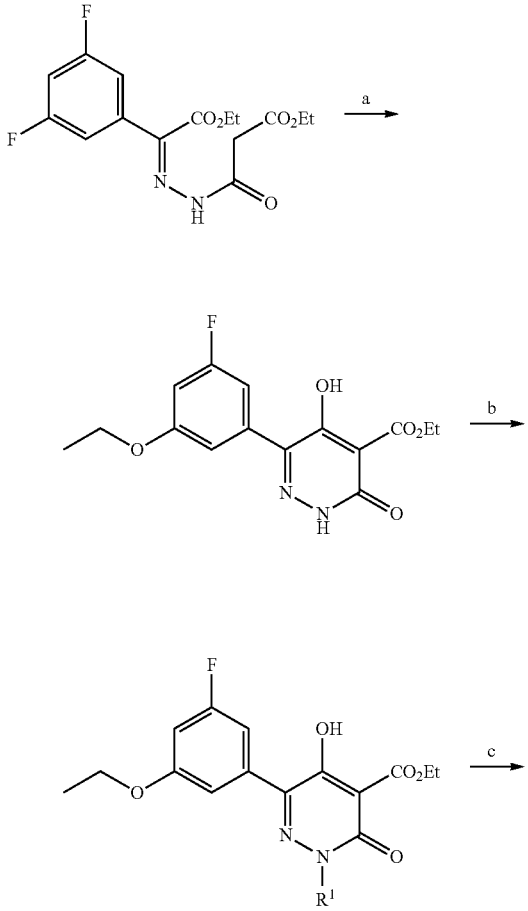

-continued

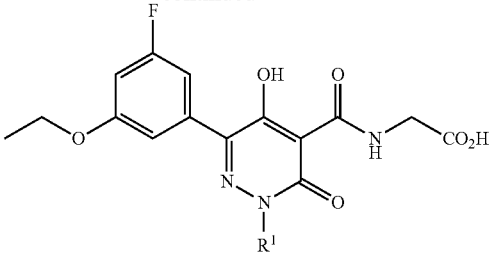

a) KHMDS, dioxane, reflux; b) NaH, $R^1Br$, DMF, 0° C. to rt; c) $NaO_2CCH_2NH_2$. $MeOCH_2CH_2OH$, reflux or microwave, 150° C.g

EXPERIMENTALS

Example 1

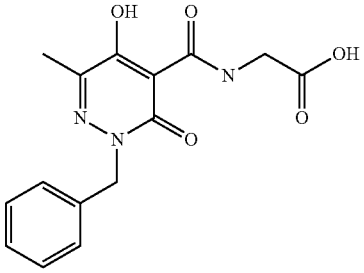

N-{[5-Hydroxy-6-methyl-3-oxo-2-(phenylmethyl)-2, 3-dihydro-4-pyridazinyl]carbonyl}glycine 1a) Ethyl 3-[2-[2-(ethyloxy)-1-methyl-2-oxoethylidene]-1-(phenylmethyl)hydrazino]-3-oxopropanoate. Ethyl pyruvate (0.324 g, 2.79 mmol) was added to a stirred mixture of benzylhydrazine dihydrochloride (0.551 g, 2.82 mmol), diisopropylethylamine (1.00 mL, 5.74 mmol) and dichloromethane (10 mL). Magnesium sulfate (excess) was added and the mixture stirred 0.5 h, then loaded onto a short column of silica gel and the product eluted (50% ethyl acetate/hexane). After evaporation of the solvent, the crude hydrazone (0.339 g) was dissolved in tetrahydrofuran (20 mL) and sodium hydride (0.075 g of a 60% oil suspension, 1.88 mmol) added with stirring. The mixture was stirred 20 min, then ethyl 3-chloro-3-oxopropionate (0.235 mL, 1.84 mmol) injected dropwise and stirring continued at room temperature 10 min and at 60° C. for 0.5 h. Further sodium hydride (0.075 g of a 60% oil suspension, 1.88 mmol) was added and stirring continued at 65° C. for 0.5 h. The mixture was cooled, poured into 0.1M aqueous hydrochloric acid (100 mL) and extracted with ethyl acetate. The extracts were dried ($MgSO_4$) and evaporated under reduced pressure. Ethyl pyruvate (0.324 g, 2.79 mmol) was added to a stirred mixture of the residue in dichloromethane (10 mL) and magnesium sulfate. After 2 h, the mixture was chromatographed (silica gel, 20-50% ethyl acetate/hexane) to give the title compound (0.205 g, 22%) as a gum. LCMS ($ES^+$) m/z 335 ($MH^+$).

1b) Ethyl 5-hydroxy-6-methyl-3-oxo-2-(phenylmethyl)-2, 3-dihydro-4-pyridazinecarboxylate. 1,8-Diazabicyclo[5.4.0] undec-7-ene (0.180 mL, 1.20 mmol) was added to a stirred solution of the compound from example 1(a) (0.203 g, 0.607 mmol) in tetrahydrofuran (5 mL) in 2 portions while heating under reflux under nitrogen over 2 h. The mixture was cooled, poured into 0.1M aqueous hydrochloric acid (50 mL) and extracted with ethyl acetate. The extracts were dried ($MgSO_4$), evaporated under reduced pressure and the residue chromatographed (silica gel, 1-5% methanol/dichloromethane) to give the title compound (0.128 g, 73%) as a solid. 1H NMR (400 MHz, DMSO-$d_6$) δ ppm 1.26 (t, J=7.20 Hz, 3H) 2.21 (s, 3H) 4.26 (q, J=7.16 Hz, 2H) 5.14 (s, 2 H) 7.24-7.36 (m, 5H) 12.13 (s, 1H).

1c) N-{[5-Hydroxy-6-methyl-3-oxo-2-(phenylmethyl)-2, 3-dihydro-4-pyridazinyl]carbonyl}glycine. A stirred mixture of the compound from example 1(b) (0.126 g, 0.437 mmol), anhydrous glycine, sodium salt (0.090 g, 0.927 mmol) and 2-methoxyethanol (4 mL) was heated under reflux under nitrogen for 2 h, cooled and diluted with water (30 mL). 1M aqueous hydrochloric acid (1 mL) was added slowly and the mixture stirred 2 h, then the solid filtered, washed with water and dried to leave the title compound (0.104 g, 75%) as a tan powder. 1H NMR (400 MHz, DMSO-$d_6$) δ ppm 2.25 (s, 3H) 4.10 (d, J=5.56 Hz, 2H) 5.25 (s, 2H) 7.27-7.37 (m, 5H) 10.17 (t, J=5.05 Hz, 1H) 12.97 (s, 1H) 15.65 (s, 1H).

Example 2

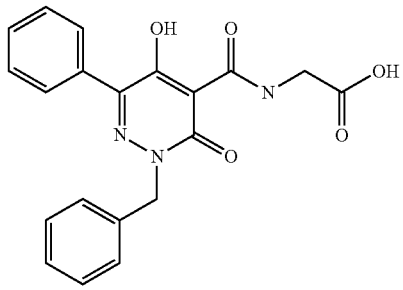

N-{[5-Hydroxy-3-oxo-6-phenyl-2-(phenylmethyl)-2, 3-dihydro-4-pyridazinyl]carbonyl}glycine 2a) Ethyl 3-[2-[2-(ethyloxy)-2-oxo-l-phenylethylidene]-1-(phenylmethyl)hydrazino]-3-oxopropanoate. A mixture of ethyl oxo(phenyl)acetate (0.315 g, 1.77 mmol), benzylhydrazine dihydrochloride (0.334 g, 1.71 mmol), diisopropylethylamine (0.596 mL, 3.42 mmol), dichloromethane (10 mL) and excess magnesium sulfate was stirred for 18 h, then filtered through a plug of silica gel and the cake washed with 50% ethyl acetate/hexane. The solvent was removed under reduced pressure and the crude hydrazone dissolved in tetrahydrofuran (5 mL) and placed under nitrogen. 1,8-Diazabicyclo[5.4.0]undec-7-ene (0.212 mL, 1.42 mmol) was added, followed by ethyl 3-chloro-3-oxopropionate (0.182 mL, 1.42 mmol) dropwise. The mixture was stirred at room temperature for 2 h, then poured into water (50 mL) and extracted with ethyl acetate. The extracts were dried ($MgSO_4$), evaporated under reduced pressure and the residue chromatographed (silica gel, 10-50% ethyl acetate/hexane) to give the title compound (0.117 g) as a gum, sufficiently pure to use in the next reaction. LCMS ($ES^+$) m/z 397 ($MH^+$).

2b) Ethyl 5-hydroxy-3-oxo-6-phenyl-2-(phenylmethyl)-2, 3-dihydro-4-pyridazinecarboxylate. 1,8-Diazabicyclo[5.4.0] undec-7-ene (0.100 mL, 0.670 mmol) was added to a stirred solution of the compound from example 2(a) (0.115 g, 0.290 mmol) in tetrahydrofuran (5 mL) under nitrogen and the mixture stirred under reflux for 2 h, then cooled, poured into 0.1M aqueous hydrochloric acid (50 mL) and extracted with ethyl acetate. The extracts were dried ($MgSO_4$), evaporated under reduced pressure and the residue chromatographed (silica gel, 1-5% methanol/dichloromethane). The material obtained was chromatographed again (silica gel, 20-30% ethyl acetate/hexane, then 1-4% methanol/dichloromethane) to give the title compound (0.037 g, 6% over 3 steps) as a solid. 1H NMR (400 MHz, DMSO-$d_6$) δ ppm 1.28 (t, J=7.08 Hz, 3H) 4.29 (q, J=7.16 Hz, 2H) 5.25 (s, 2H) 7.27-7.38 (m, 5H) 7.44-7.49 (m, 3H), 7.66-7.71 (m, 2H).

2c) N-{[5-Hydroxy-3-oxo-6-phenyl-2-(phenylmethyl)-2,3-dihydro-4-pyridazinyl]carbonyl}glycine. A stirred mixture of the compound from example 2(b) (0.036 g, 0.103 mmol), anhydrous glycine, sodium salt (0.050 g, 0.515 mmol) and 2-methoxyethanol (2 mL) was heated under reflux under nitrogen for 2 h, cooled and diluted with water (20 mL). 1M aqueous hydrochloric acid (0.5 mL) was added slowly and the mixture allowed to stand for 18 h, then the solid filtered, washed with water and dried to leave the title compound (0.030 g, 77%) as a pale pink solid. 1H NMR (400 MHz, DMSO-$d_6$) δ ppm 4.13 (d, J=5.56 Hz, 2H) 5.37 (s, 2 H) 7.29-7.39 (m, 5H) 7.46-7.54 (m, 3H) 7.75-7.82 (m, 2H) 10.26 (t, J=4.93 Hz, 1H) 13.00 (br s, 1H).

Example 3

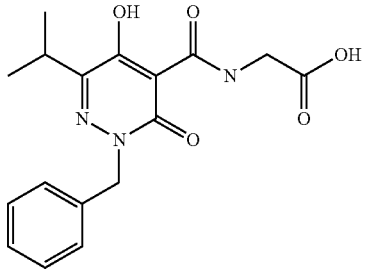

N-{[5-Hydroxy-6-(1-methylethyl)-3-oxo-2-(phenylmethyl)-2,3-dihydro-4-pyridazinyl]carbonyl}glycine 3a) Ethyl 3-oxo-3-[1-(phenylmethyl)hydrazino]propanoate. A mixture of benzylhydrazine dihydrochloride (2.50 g, 12.8 mmol), potassium carbonate (1.77 g, 12.8 mmol), acetone (6.0 mL, 82 mmol) and ethyl acetate (30 mL) was stirred at room temperature while a solution of 1M aqueous sodium hydroxide (6.0 mL, 6.0 mmol) was added dropwise. After the addition, the mixture was stirred 0.5 h, then excess magnesium sulfate added and the mixture filtered. The filtrate was evaporated under reduced pressure and the residue azeotroped with toluene three times, then dissolved in tetrahydrofuran (50 mL). 1,8-Diazabicyclo[5.4.0]undec-7-ene (1.84 mL, 12.3 mmol) was added to the stirred solution under nitrogen at 0° C., followed by ethyl 3-chloro-3-oxopropionate (1.57 mL, 12.3 mmol) dropwise. The mixture was stirred at 0° C. for 5 min, and at room temperature for 3 h, then 1M aqueous hydrochloric acid (50 mL) added. After stirring a further 0.5 h, water (100 mL) was added and the mixture extracted with ethyl acetate. The extracts were washed with brine, dried ($MgSO_4$), evaporated under reduced pressure and the residue chromatographed (silica gel, 1-5% methanol/dichloromethane) to give the title compound (1.60 g) as an oil. 1H NMR (400 MHz, DMSO-$d_6$) δ ppm 1.18 (t, J=7.08 Hz, 3H) 3.56 (s, 2H) 4.08 (q, J=7.16 Hz, 2H) 4.58 (s, 2H) 4.65 (s, 2H) 7.25-7.36 (m, 5H).

3b) Ethyl 5-hydroxy-6-(1-methylethyl)-3-oxo-2-(phenylmethyl)-2,3-dihydro-4-pyridazinecarboxylate. A solution of the compound from example 3(a) (0.120 g, 0.508 mmol), ethyl 3-methyl-2-oxobutanoate (0.066 g, 0.458 mmol) and acetic acid (0.030 g, 0.500 mmol) in dichloromethane (2 mL) was stirred at 50° C. for 18 h, then cooled, diluted with ethyl acetate (2 mL) and filtered. Solvent was removed from the filtrate under reduced pressure and the residue azeotroped 3 times with toluene, then taken up in tetrahydrofuran (10 mL).

Diazabicyclo[5.4.0]undec-7-ene (0.200 mL, 1.34 mmol) was added and the solution refluxed under nitrogen for 1.5 h, then cooled and poured into 1M aqueous hydrochloric acid (10 mL). The mixture was extracted with ether and the organic extracts washed with 1 M aqueous sodium hydroxide. The aqueous extracts were washed with ether, then acidified with 1M aqueous hydrochloric acid and extracted with ether. The extracts were dried ($MgSO_4$), evaporated under reduced pressure and the residue chromatographed (silica gel, 1-5% methanol/dichloromethane) to give the title compound (0.029 g, 20%) as a solid. LCMS ($ES^+$) m/z 317 ($MH^+$).

3c) N-{[5-Hydroxy-6-(1-methylethyl)-3-oxo-2-(phenylmethyl)-2,3-dihydro-4-pyridazinyl]carbonyl}glycine. A stirred mixture of the compound from example 3(b) (0.029 g, 0.092 mmol), anhydrous glycine, sodium salt (0.050 g, 0.515 mmol) and 2-methoxyethanol (2 mL) was heated under reflux under nitrogen for 2 h, cooled and diluted with water (20 mL). 1M aqueous hydrochloric acid (0.5 mL) was added slowly and the mixture stirred for 0.5 h, then the solid filtered, washed with water and dried to leave the title compound (0.025 g, 78%) as a solid. 1H NMR (400 MHz, DMSO-$d_6$) δ ppm 1.20 (d, J=7.07 Hz, 6H) 3.19 (sept, J=6.82 Hz, 1H) 4.09 (d, J=5.56 Hz, 2H) 5.25 (s, 2H) 7.27-7.37 (m, 5H) 10.19 (t, J=5.05 Hz, 1 H) 12.95 (br s, 1H), 15.87 (br s, 1H).

Example 4

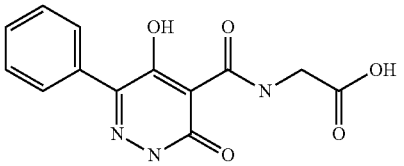

N-[(5-Hydroxy-3-oxo-6-phenyl-2,3-dihydro-4-pyridazinyl)carbonyl]glycine

4a) Ethyl 3-{2-[2-(ethyloxy)-2-oxo-1-phenylethylidene]hydrazino}-3-oxopropanoate. A mixture of ethyl 3-hydrazino-3-oxopropionate (1.46 g, 10.0 mmol), ethyl benzoylformate (2.14 g, 12.0 mmol), acetic acid (0.5 mL, 8.3 mmol) and dichloromethane (10 mL) was stirred at room temperature with excess anhydrous magnesium sulfate for 20 h, then filtered and the cake washed with ethyl acetate. The filtrate was evaporated under reduced pressure, azeotroped 3 times with toluene and chromatographed (silica gel, 10-3-% ethyl acetate/hexane) to give the title compound (0.773 g, 25%). 1H NMR (400 MHz, DMSO-$d_6$) δ ppm 1.15 (t, J=7.07 Hz, 3H) 1.30 (t, J=7.07 Hz, 3H) 3.74 (s, 2H) 4.08 (q, J=7.07 Hz, 2H) 4.40 (q, J=7.18 Hz, 2H) 7.42-7.49 (m, 3H) 7.55-7.59 (m, 2H) 11.57 (s, 1H).

4b) Ethyl 5-hydroxy-3-oxo-6-phenyl-2,3-dihydro-4-pyridazinecarboxylate. A 1 M solution of piperidinium acetate in 5% ethanol/toluene (1.10 mL, 1.10 mmol) was added to a solution of the compound from example 4(a) (0.350 g, 1.14 mmol) in toluene (10 mL) and the mixture stirred under reflux for 1 h. Diazabicyclo[5.4.0]undec-7-ene (0.30 mL, 2.00 mmol) was added and the reflux continued for 2 h. After cooling, the mixture was partitioned between 1M aqueous hydrochloric acid and ethyl acetate. The extracts were dried ($MgSO_4$), evaporated under reduced pressure and the residue chromatographed (silica gel, 2-8% methanol/dichloromethane). The partially purified product was triturated with ether to give the title compound (0.115 g, 39%) as a solid. 1H NMR (400 MHz, DMSO-$d_6$) δ ppm 1.30 (t, J=7.20 Hz, 3H) 4.32 (q, J=7.16 Hz, 2H) 7.43-7.49 (m, 3H) 7.64-7.67 (m, 2H) 13.05 (s, 1H).

4c) N-[(5-Hydroxy-3-oxo-6-phenyl-2,3-dihydro-4-pyridazinyl)carbonyl]glycine. A stirred mixture of the compound from example 4(b) (0.060 g, 0.251 mmol), anhydrous glycine, sodium salt (0.045 g, 0.462 mmol) and 2-methoxyethanol (3 mL) was heated under reflux under nitrogen for 2 h, cooled and diluted with water (20 mL). After filtering, 1M aqueous hydrochloric acid (0.5 mL) was added slowly to the filtrate, then the solid filtered, washed with water and dried to leave the title compound (0.025 g, 78%) as a white powder. 1H NMR (400 MHz, DMSO-$d_6$) δ ppm 4.02 (d, J=5.56 Hz, 2H) 7.40-7.47 (m, 3H) 7.74-7.80 (m, 2H) 10.45 (s, 1H) 12.94 (s, 1H).

Example 5

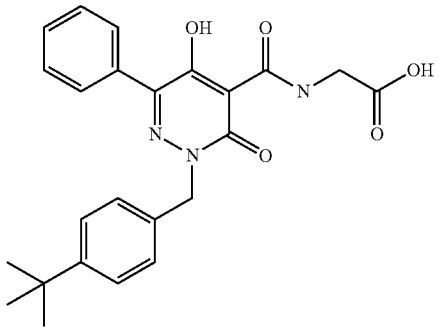

N-[(2-{[4-(1,1-Dimethylethyl)phenyl]methyl}-5-hydroxy-3-oxo-6-phenyl-2,3-dihydro-4-pyridazinyl)carbonyl]glycine 5a) Ethyl 2-{[4-(1,1-dimethylethyl)phenyl]methyl}-5-hydroxy-3-oxo-6-phenyl-2,3-dihydro-4-pyridazinecarboxylate. Sodium hydride (0.020 g of a 60% oil suspension, 0.500 mmol) was added to a stirred solution of the compound from example 4(b) (0.052 g, 0.200 mmol) in dimethylformamide (1 mL) under nitrogen. After 15 min stirring at room temperature, 4-t-butylbenzyl bromide (0.037 mL, 0.200 mmol) was injected and the mixture stirred for 2 h, then partitioned between 1M aqueous hydrochloric acid and ethyl acetate. The extracts were washed with water and brine, then dried ($MgSO_4$), evaporated under reduced pressure and the residue chromatographed (silica gel, 0-5% methanol/dichloromethane) to give the title compound (0.053 g, 65%) as a gum. 1H NMR (400 MHz, DMSO-$d_6$) δ ppm 1.25 (s, 9H) 1.28 (t, J=7.20 Hz, 3H) 4.29 (q, J=7.07 Hz, 2H) 5.20 (s, 2H) 7.25-7.29 (m, 2H) 7.34-7.41 (m, 2H) 7.44-7.50 (m, 3H) 7.67-7.72 (m, 2H).

5b) N-[(2-{[4-(1,1-Dimethylethyl)phenyl]methyl}-5-hydroxy-3-oxo-6-phenyl-2,3-dihydro-4-pyridazinyl)carbonyl]glycine. A stirred mixture of the compound from example 5(a) (0.052 g, 0.128 mmol), anhydrous glycine, sodium salt (0.050 g, 0.515 mmol) and 2-methoxyethanol (3 mL) was heated under reflux under nitrogen for 2 h, cooled and diluted with water (20 mL). After filtering, 1M aqueous hydrochloric acid was added slowly to the filtrate until the pH had dropped to 2, then the solid filtered, washed with water and dried to leave the title compound (0.047 g, 84%) as a pale pink powder. 1H NMR (400 MHz, DMSO-$d_6$) δ ppm 1.25 (s, 9H) 4.13 (d, J=5.56 Hz, 2H) 5.32 (s, 2H) 7.28-7.34 (m, 2H) 7.34-7.40 (m, 2H) 7.48-7.51 (m, 3H) 7.76-7.82 (m, 2H) 10.27 (t, J=5.18 Hz, 1H) 12.99 (s, 1H) 16.32 (s, 1H).

Example 6

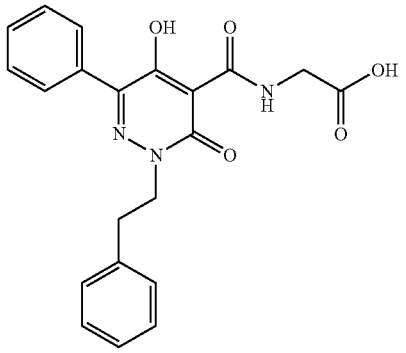

N-{[5-Hydroxy-3-oxo-6-phenyl-2-(2-phenylethyl)-2,3-dihydropyridazin-4-yl]carbonyl}glycine 6a) Ethyl 5-hydroxy-3-oxo-6-phenyl-2-(2-phenylethyl)-2,3-dihydro-4-pyridazinecarboxylate. Sodium hydride (0.040 g of a 60% oil suspension, 1.00 mmol) was added to a stirred solution of ethyl 5-hydroxy-3-oxo-6-phenyl-2,3-dihydro-4-pyridazinecarboxylate (example 4(b), 0.100 g, 0.384 mmol) in dimethylformamide (1.5 mL) under nitrogen. After 15 min stirring at room temperature, the mixture was cooled in an ice bath and (2-iodoethyl)benzene (0.056 mL, 0.384 mmol) injected. The mixture was stirred for 18 h while warming to room temperature, then poured into 0.1M aqueous hydrochloric acid (50 mL) and extracted with ethyl acetate. The extracts were washed with water and brine, then dried ($MgSO_4$), evaporated under reduced pressure and the residue chromatographed (silica gel, 1-5% methanol dichloromethane) to give the title compound (0.077 g, 55%) as a colourless gum. 1H NMR (400 MHz, DMSO-$d_6$) δ ppm 1.30 (t, J=7.07 Hz, 3H) 3.04 (t, J=7.33 Hz, 2H) 4.30 (t, J=7.32 Hz, 2H) 4.32 (q, J=7.07 Hz, 2H) 7.20-7.26 (m, 3H) 7.28-7.35 (m, 2H) 7.40-7.47 (m, 3H) 7.50-7.56 (m, 2H) 12.45 (br. s., 1 H).

6b) N-{[5-Hydroxy-3-oxo-6-phenyl-2-(2-phenylethyl)-2,3-dihydropyridazin-4-yl]carbonyl}glycine. A stirred mixture of ethyl 5-hydroxy-3-oxo-6-phenyl-2-(2-phenylethyl)-2,3-dihydro-4-pyridazinecarboxylate (0.075 g, 0.206 mmol), anhydrous glycine, sodium salt (0.050 g, 0.515 mmol) and 2-methoxyethanol (3 mL) was heated under reflux under nitrogen for 2 h, then cooled and diluted with water (30 mL).

After filtering, 1M aqueous hydrochloric acid was added slowly to the filtrate until the pH had dropped to 2, then the solid filtered, washed with water and dried to leave the title compound (0.073 g, 90%) as an off-white powder. 1H NMR (400 MHz, DMSO-$d_6$) δ ppm 3.09 (t, J=7.33 Hz, 2H) 4.12 (d, J=5.31 Hz, 2H) 4.40 (t, J=7.33 Hz, 2H) 7.20-7.27 (m, 3H) 7.28-7.35 (m, 2H) 7.41-7.50 (m, 3H) 7.59-7.66 (m, 2H) 10.35 (t, J=5.31 Hz, 1 H).

Example 7

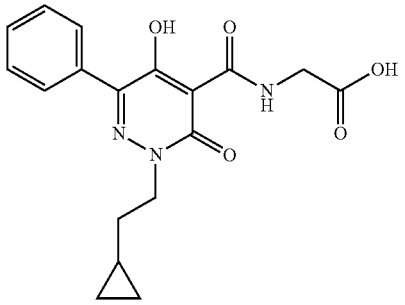

N-{[2-(2-Cyclopropylethyl)-5-hydroxy-3-oxo-6-phenyl-2,3-dihydro-4-pyridazinyl]carbonyl}glycine 7a) (2-Bromoethyl)cyclopropane. N-Bromosuccinimide (1.60 g, 8.99 mmol) was added in portions to an ice-cooled, stirred solution of 2-cyclopropylethanol (0.760 g, 8.82 mmol) and triphenylphosphine (2.36 g, 9.00 mmol) in dichloromethane (10 mL) under nitrogen. The mixture was stirred for 2 h while warming to room temperature, then diluted with hexane (90 mL) and filtered through a short silica gel column. The column was washed with 10% ethyl acetate/hexane and the combined filtrates evaporated under reduced pressure at room temperature to give the title compound (0.179 g, 14%) as a colourless liquid. 1H NMR (400 MHz, CHLOROFORM-d) δ ppm 0.10-0.17 (m, 2H) 0.47-0.56 (m, 2H) 0.79-0.90 (m, 1H) 1.79 (q, J=6.91 Hz, 2H) 3.47 (t, J=7.07 Hz, 2H).

7b) Ethyl 2-(2-cyclopropylethyl)-5-hydroxy-3-oxo-6-phenyl-2,3-dihydro-4-pyridazinecarboxylate. Sodium hydride (0.040 g of a 60% oil suspension, 1.00 mmol) was added to a stirred solution of ethyl 5-hydroxy-3-oxo-6-phenyl-2,3-dihydro-4-pyridazinecarboxylate (example 4(b), 0.100 g, 0.384 mmol) in dimethylformamide (1.5 mL) under nitrogen. After 15 min stirring at room temperature, the mixture was cooled in an ice bath and (2-bromoethyl)cyclopropane (0.057 g, 0.384 mmol) added. The mixture was stirred for 18 h while warming to room temperature, then poured into 0.1M aqueous hydrochloric acid (50 mL) and extracted with ethyl acetate. The extracts were washed with water and brine, then dried ($MgSO_4$), evaporated under reduced pressure and the residue chromatographed (silica gel, 1-5% methanol/dichloromethane) to give the title compound (0.067 g, 53%) as a colourless gum. 1H NMR (400 MHz, DMSO-$d_6$) δ ppm −0.05-0.06 (m, 2H) 0.34-0.45 (m, 2H) 0.64-0.78 (m, 1H) 1.29 (t, J=7.07 Hz, 3H) 1.62 (q, J=7.07 Hz, 2H) 4.14 (t, J=7.20 Hz, 2H) 4.31 (q, J=7.07 Hz, 2H) 7.41-7.52 (m, 3H) 7.63-7.71 (m, 2H) 12.42 (br. s., 1H).

7c) N-{[2-(2-Cyclopropylethyl)-5-hydroxy-3-oxo-6-phenyl-2,3-dihydro-4-pyridazinyl]carbonyl}glycine. A stirred mixture of ethyl 2-(2-cyclopropylethyl)-5-hydroxy-3-oxo-6-phenyl-2,3-dihydro-4-pyridazinecarboxylate (0.065 g, 0.198 mmol), anhydrous glycine, sodium salt (0.050 g, 0.515 mmol) and 2-methoxyethanol (3 mL) was heated under reflux under nitrogen for 2 h, then cooled and diluted with water (30 mL). After filtering, 1M aqueous hydrochloric acid was added slowly to the filtrate until the pH had dropped to 2, then the solid filtered, washed with water and dried to leave the title compound (0.062 g, 87%) as an off-white powder. 1H NMR (400 MHz, DMSO-$d_6$) δ ppm −0.05-0.09 (m, 2H) 0.35-0.47 (m, 2H) 0.66-0.79 (m, 1H) 1.68 (q, J=7.07 Hz, 2H) 4.15 (d, J=5.56 Hz, 2H) 4.26 (t, J=7.07 Hz, 2H) 7.41-7.56 (m, 3H) 7.69-7.84 (m, 2H) 10.35 (br t, J=5.05 Hz, 1H) 13.00 (br. s., 1H) 16.25 (s, 1H).

Example 8

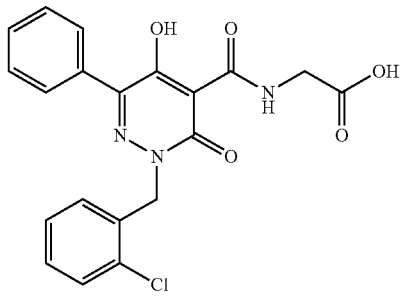

N-{[2-(2-Chlorobenzyl)-5-hydroxy-3-oxo-6-phenyl-2,3-dihydropyridazin-4-yl]carbonyl}glycine 8a) Ethyl 2-[(2-chlorophenyl)methyl]-5-hydroxy-3-oxo-6-phenyl-2,3-dihydro-4-pyridazinecarboxylate. Sodium hydride (0.040 g of a 60% oil suspension, 1.00 mmol) was added to a stirred solution of ethyl 5-hydroxy-3-oxo-6-phenyl-2,3-dihydro-4-pyridazinecarboxylate (example 4(b), 0.100 g, 0.384 mmol) in dimethylformamide (1.5 mL) under nitrogen. After 15 min stirring at room temperature, the mixture was cooled in an ice bath and 2-chlorobenzyl bromide (0.051 mL, 0.384 mmol) injected. The mixture was stirred for 18 h while warming to room temperature, then poured into 0.1M aqueous hydrochloric acid (50 mL) and extracted with ethyl acetate. The extracts were washed with water and brine, then dried ($MgSO_4$), evaporated under reduced pressure and the residue chromatographed (silica gel, 1-5% methanol/dichloromethane) to give the title compound (0.098 g, 66%) as a colourless gum. 1H NMR (400 MHz, CHLOROFORM-d) δ ppm 1.50 (t, J=7.20 Hz, 3H) 4.55 (q, J=7.07 Hz, 2H) 5.54 (s, 2 H) 7.20-7.28 (m, 3H) 7.35-7.52 (m, 4H) 7.75-7.84 (m, 2H) 13.83 (s, 1H).

8b) N-{[2-(2-Chlorobenzyl)-5-hydroxy-3-oxo-6-phenyl-2,3-dihydropyridazin-4-yl]carbonyl}glycine. A stirred mixture of ethyl 2-[(2-chlorophenyl)methyl]-5-hydroxy-3-oxo-6-phenyl-2,3-dihydro-4-pyridazinecarboxylate (0.098 g, 0.255 mmol), anhydrous glycine, sodium salt (0.050 g, 0.515 mmol) and 2-methoxyethanol (3 mL) was heated under reflux under nitrogen for 2 h, then cooled and diluted with water (30 mL). After filtering, 1M aqueous hydrochloric acid was added slowly to the filtrate until the pH had dropped to 2, then the solid filtered, washed with water and dried to leave the title compound (0.099 g, 93%) as an off-white powder. 1H NMR (400 MHz, DMSO-$d_6$) δ ppm 4.14 (d, J=5.81 Hz, 2H) 5.46 (s, 2H) 7.23-7.26 (m, 1H) 7.29-7.40 (m, 2H) 7.44-7.49

(m, 3H) 7.52 (dd, J=7.45, 1.64 Hz, 1H) 7.71-7.79 (m, 2H) 10.21 (br t, J=4.80 Hz, 1H) 12.98 (br. s., 1H) 16.41 (br. s., 1H).

Example 9

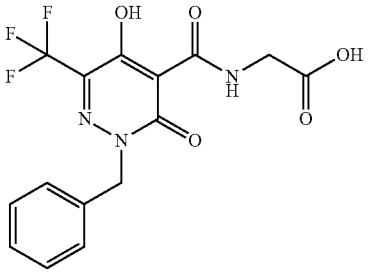

N-{[5-Hydroxy-3-oxo-2-(phenylmethyl)-6-(trifluoromethyl)-2,3-dihydro-4-pyridazinyl]carbonyl}glycine 9a) Ethyl 5-hydroxy-3-oxo-6-(trifluoromethyl)-2,3-dihydro-4-pyridazinecarboxylate. A mixture of ethyl 3-hydrazino-3-oxopropionate (0.438 g, 3.00 mmol), ethyl 3,3,3-trifluoro-2-oxopropionate (0.510 g, 3.00 mmol), p-toluenesulfonic acid monohydrate acid (0.057 g, 0.300 mmol) and toluene (10 mL) was refluxed using a Dean and Stark trap to remove water for 3 h, then cooled. Magnesium sulfate was added and the mixture filtered through a short silica gel column. The column was washed with 50% ethyl acetate/hexane and the combined filtrates evaporated under reduced pressure. The residue was chromatographed (silica gel, 10-40% ethyl acetate/hexane) to give the intermediate hydrazone. Diazabicyclo[5.4.0]undec-7-ene (0.083 mL, 0.558 mmol) was added to a solution of the hydrazone in dioxane (5 mL) and the mixture refluxed under nitrogen for 1 h. After cooling, 0.1M aqueous hydrochloric acid (50 mL) was added and the mixture extracted with ethyl acetate. The extracts were dried ($MgSO_4$) and evaporated under reduced pressure to give the title compound (0.085 g, 12%) as a light brown powder. 1H NMR (400 MHz, DMSO-$d_6$) δ ppm 1.26 (t, J=7.07 Hz, 3H) 4.25 (q, J=7.07 Hz, 2H) 13.30 (s, 1H).

9b) Ethyl 5-hydroxy-3-oxo-2-(phenylmethyl)-6-(trifluoromethyl)-2,3-dihydro-4-pyridazinecarboxylate. Sodium hydride (0.040 g of a 60% oil suspension, 1.00 mmol) was added to a stirred solution of ethyl 5-hydroxy-3-oxo-6-(trifluoromethyl)-2,3-dihydro-4-pyridazinecarboxylate (0.083 g, 0.329 mmol) in dimethylformamide (1.5 mL) under nitrogen. After 10 min stirring at room temperature, the mixture was cooled in an ice bath and benzyl bromide (0.043 mL, 0.362 mmol) injected. The mixture was stirred for 3 h at 0° C. 0.1M aqueous hydrochloric acid (50 mL) was added and the mixture extracted with ethyl acetate. The extracts were washed with water and brine, then dried ($MgSO_4$), evaporated under reduced pressure and the residue chromatographed (silica gel, 5-10% methanol dichloromethane) to give the title compound (0.050 g, 44%). 1H NMR (400 MHz, DMSO-$d_6$) δ ppm 1.23 (t, J=6.95 Hz, 3H) 4.17 (q, J=7.07 Hz, 2H) 5.14 (s, 2H) 7.12-7.44 (m, 5H).

9c) N-{[5-Hydroxy-3-oxo-2-(phenylmethyl)-6-(trifluoromethyl)-2,3-dihydro-4-pyridazinyl]carbonyl}glycine. A stirred mixture of ethyl 5-hydroxy-3-oxo-2-(phenylmethyl)-6-(trifluoromethyl)-2,3-dihydro-4-pyridazinecarboxylate (0.048 g, 0.140 mmol), anhydrous glycine, sodium salt (0.050 g, 0.515 mmol) and 2-methoxyethanol (3 mL) was heated under reflux under nitrogen for 2 h, then cooled and diluted with water (30 mL). After filtering, 1M aqueous hydrochloric acid was added slowly to the filtrate until the pH had dropped to 2. The mixture was extracted with ethyl acetate and the extracts dried ($MgSO_4$), then evaporated under reduced pressure. The residue was purified by HPLC (ODS, 10-90% acetonitrile/water+0.1% trifluoroacetic acid). The product was reprecipitated from 1M aqueous sodium hydroxide with 1M aqueous hydrochloric acid and the solid filtered, washed with water and dried to give the title compound (0.014 g, 27%) as a white solid. 1H NMR (400 MHz, DMSO-$d_6$) δ ppm 4.12 (d, J=5.81 Hz, 2H) 5.34 (s, 2H) 7.27-7.41 (m, 5H) 9.96 (t, J=5.43 Hz, 1H) 13.02 (br. s., 1H).

Example 10

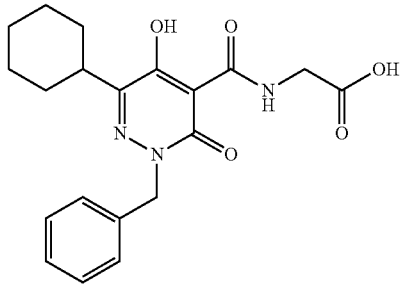

N-{[6-Cyclohexyl-5-hydroxy-3-oxo-2-(phenylmethyl)-2,3-dihydro-4-pyridazinyl]carbonyl}glycine 10a) Ethyl 6-cyclohexyl-5-hydroxy-3-oxo-2,3-dihydro-4-pyridazinecarboxylate. A mixture of ethyl 3-hydrazino-3-oxopropionate (0.450 g, 3.08 mmol), ethyl cyclohexyl(oxo)acetate (0.600 g, 3.26 mmol), p-toluenesulfonic acid monohydrate acid (0.060 g, 0.315 mmol) and toluene (15 mL) was refluxed using a Dean and Stark trap to remove water for 1 h, then cooled and chromatographed (silica gel, 10-40% ethyl acetate/hexane) to give the intermediate hydrazone. Diazabicyclo[5.4.0]undec-7-ene (0.540 mL, 3.61 mmol) was added to a solution of the hydrazone, pre-dried by azeotroping with toluene, in dioxane (10 mL) and the mixture refluxed under nitrogen for 19 h. After cooling, 0.1M aqueous hydrochloric acid (50 mL) was added and the mixture extracted with ethyl acetate. The extracts were washed with brine, dried ($MgSO_4$) and evaporated under reduced pressure. The residue was chromatographed (silica gel, 1-5% methanol/dichloromethane) to give the title compound (0.404 g, 52%) as a cream solid. 1H NMR (400 MHz, DMSO-$d_6$) δ ppm 1.12-1.23 (m, 1H) 1.27 (t, J=7.07 Hz, 3H) 1.29-1.38 (m, 4H) 1.64-1.71 (m, 1H) 1.72-1.90 (m, 4H) 2.74-2.86 (m, 1H) 4.28 (q, J=7.16 Hz, 2H) 12.30 (br. s., 1H) 12.62 (s, 1H).

10b) Ethyl 6-cyclohexyl-5-hydroxy-3-oxo-2-(phenylmethyl)-2,3-dihydro-4-pyridazinecarboxylate. Sodium hydride (0.040 g of a 60% oil suspension, 1.00 mmol) was added to a stirred suspension of ethyl 6-cyclohexyl-5-hydroxy-3-oxo-2,3-dihydro-4-pyridazinecarboxylate (0.100 g, 0.376 mmol) in dimethylformamide (1.5 mL) under nitrogen. After 10 min stirring at room temperature, the mixture was cooled in an ice bath and benzyl bromide (0.045 mL, 0.378 mmol) injected. The mixture was stirred for 0.5 h at 0° C. and 0.5 h at room temperature. 0.1M aqueous hydrochloric acid (50 mL) was added and the mixture extracted with ethyl acetate. The extracts were washed with water and brine, then dried ($MgSO_4$), evaporated under reduced pressure and the residue chromatographed (silica gel, 0-4% methanol/dichloromethane) to give the title compound (0.095 g, 71%) as a colourless oil. LCMS ($ES^+$) m/z 357 ($MH^+$).

10c) N-{[6-Cyclohexyl-5-hydroxy-3-oxo-2-(phenylmethyl)-2,3-dihydro-4-pyridazinyl]carbonyl}glycine. A stirred mixture of ethyl 6-cyclohexyl-5-hydroxy-3-oxo-2-(phenylmethyl)-2,3-dihydro-4-pyridazinecarboxylate (0.095 g, 0.267 mmol), anhydrous glycine, sodium salt (0.053 g, 0.544 mmol) and 2-methoxyethanol (3 mL) was heated under reflux under nitrogen for 2 h, then cooled and diluted with water (30 mL). 1M aqueous hydrochloric acid was added slowly until the pH had dropped to 2. After 60 h, the solid was filtered, washed with water and dried to leave the title compound (0.095 g, 92%) as a white solid. 1H NMR (400 MHz, DMSO-$d_6$) δ ppm 1.12-1.28 (m, 1H) 1.28-1.49 (m, 4H) 1.63-1.72 (m, 1H) 1.74-1.81 (m, 2 H) 1.83-1.91 (m, 2H) 2.82-2.94 (m, 1H) 4.09 (d, J=5.56 Hz, 2H) 5.25 (s, 2H) 7.25-7.31 (m, 3 H) 7.31-7.38 (m, 2H) 10.19 (t, J=5.18 Hz, 1H) 12.97 (br. s., 1H) 15.86 (br. s., 1H).

Example 11

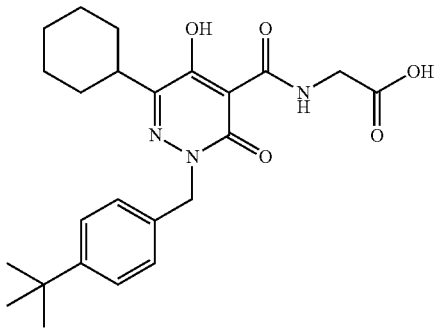

N-[(6-Cyclohexyl-2-{[4-(1,1-dimethylethyl)phenyl]methyl}-5-hydroxy-3-oxo-2,3-dihydro-4-pyridazinyl)carbonyl]glycine 11a) Ethyl 6-cyclohexyl-2-{[4-(1,1-dimethylethyl)phenyl]methyl}-5-hydroxy-3-oxo-2,3-dihydro-4-pyridazinecarboxylate. Sodium hydride (0.040 g of a 60% oil suspension, 1.00 mmol) was added to a stirred suspension of ethyl 6-cyclohexyl-5-hydroxy-3-oxo-2,3-dihydro-4-pyridazinecarboxylate (example 10(a), 0.100 g, 0.376 mmol) in dimethylformamide (2.0 mL) under nitrogen. After 15 min stirring at room temperature, the mixture was cooled in an ice bath and 4-tert-butylbenzyl bromide (0.071 mL, 0.384 mmol) injected. The mixture was stirred for 0.5 h at 0° C. and 3 h at room temperature. 0.1M aqueous hydrochloric acid (50 mL) was added and the mixture extracted with ethyl acetate. The extracts were washed with dilute aqueous sodium chloride, then dried ($MgSO_4$), evaporated under reduced pressure and the residue chromatographed (silica gel, 0-6% methanol/dichloromethane) to give the title compound (0.087 g, 56%) as a gum. LCMS ($ES^+$) m/z 413 ($MH^+$).

11b) N-[(6-Cyclohexyl-2-{[4-(1,1-dimethylethyl)phenyl]methyl}-5-hydroxy-3-oxo-2,3-dihydro-4-pyridazinyl)carbonyl]glycine. A stirred mixture of ethyl 6-cyclohexyl-2-{[4-(1,1-dimethylethyl)phenyl]methyl}-5-hydroxy-3-oxo-2,3-dihydro-4-pyridazinecarboxylate (0.087 g, 0.211 mmol), anhydrous glycine, sodium salt (0.050 g, 0.515 mmol) and 2-methoxyethanol (3 mL) was heated under reflux under nitrogen for 2 h, then cooled and diluted with water (30 mL). The mixture was filtered and 1M aqueous hydrochloric acid added slowly until the pH had dropped to 2. After 18 h, the solid was filtered, washed with water, dried and chromatographed (silica gel, 10% methanol/dichloromethane). The product was precipitated from methanol with water, and the solid collected, washed with water, then dried to leave the title compound (0.057 g, 61%) as a solid. 1H NMR (400 MHz, DMSO-$d_6$) δ ppm 1.18-1.24 (m, 1H) 1.25 (s, 9H) 1.29-1.50 (m, 4 H) 1.64-1.73 (m, 1H) 1.76-1.81 (m, 2H) 1.83-1.92 (m, 2H) 2.79-2.97 (m, 1H) 4.09 (d, J=5.81 Hz, 2H) 5.20 (s, 2H) 7.23 (d, J=8.34 Hz, 2H) 7.36 (d, J=8.34 Hz, 2H) 10.19 (t, J=5.56 Hz, 1H) 12.94 (br. s., 1H) 15.83 (s, 1H).

Example 12

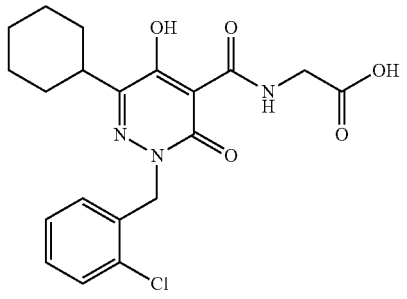

N-({2-[(2-Chlorophenyl)methyl]-6-cyclohexyl-5-hydroxy-3-oxo-2,3-dihydro-4-pyridazinyl}carbonyl)glycine 12a) Ethyl 2-[(2-chlorophenyl)methyl]-6-cyclohexyl-5-hydroxy-3-oxo-2,3-dihydro-4-pyridazinecarboxylate. Sodium hydride (0.040 g of a 60% oil suspension, 1.00 mmol) was added to a stirred suspension of ethyl 6-cyclohexyl-5-hydroxy-3-oxo-2,3-dihydro-4-pyridazinecarboxylate (example 10(a), 0.100 g, 0.376 mmol) in dimethylformamide (2.0 mL) under nitrogen. After 15 min stirring at room temperature, the mixture was cooled in an ice bath and 2-chlorobenzyl bromide (0.051 mL, 0.384 mmol) injected. The mixture was stirred for 0.5 h at 0° C. and 3 h at room temperature. 0.1M aqueous hydrochloric acid (50 mL) was added and the mixture extracted with ethyl acetate. The extracts were washed with dilute aqueous sodium chloride, then dried ($MgSO_4$), evaporated under reduced pressure and the residue chromatographed (silica gel, 0-6% methanol/dichloromethane) to give the title compound (0.093 g, 63%) as a gum. LCMS ($ES^+$) m/z 391 ($MH^+$).

12b) N-({2-[(2-Chlorophenyl)methyl]-6-cyclohexyl-5-hydroxy-3-oxo-2,3-dihydro-4-pyridazinyl}carbonyl)glycine. A stirred mixture of ethyl 2-[(2-chlorophenyl)methyl]-6-cyclohexyl-5-hydroxy-3-oxo-2,3-dihydro-4-pyridazinecarboxylate (0.093 g, 0.238 mmol), anhydrous glycine, sodium salt (0.050 g, 0.515 mmol) and 2-methoxyethanol (3 mL) was heated under reflux under nitrogen for 2 h, then cooled and diluted with water (30 mL). The mixture was filtered and 1M aqueous hydrochloric acid added slowly until the pH had dropped to 2. After 18 h, the solid was filtered, washed with water, dried and chromatographed (silica gel, 10% methanol/dichloromethane). The product was precipitated from methanol with water, and the solid collected, washed with water, then dried to leave the title compound (0.041 g, 41%) as a solid. LCMS ($ES^+$) m/z 420 ($MH^+$).

Example 13

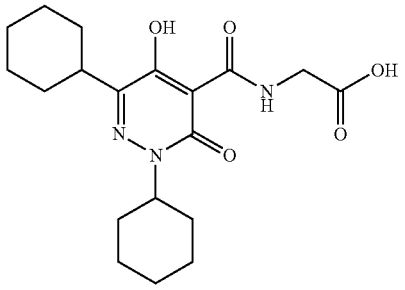

N-[(2,6-Dicyclohexyl-5-hydroxy-3-oxo-2,3-dihydro-4-pyridazinyl)carbonyl]glycine

13a) Ethyl 2,6-dicyclohexyl-5-hydroxy-3-oxo-2,3-dihydro-4-pyridazinecarboxylate. A mixture of cyclohexylhydrazine hydrochloride (0.451 g, 3.00 mmol), ethyl cyclohexyl (oxo)acetate (0.500 g, 2.71 mmol), anhydrous sodium acetate (0.246 g, 0.300 mmol) and dichloromethane (5 mL) was stirred at room temperature for 18 h, then diluted with water and extracted with dichloromethane. The extracts were dried ($MgSO_4$), evaporated under reduced pressure and the residue chromatographed (silica gel, 5-30% ethyl acetate/hexane) to give the intermediate hydrazone. Diazabicyclo[5.4.0]undec-7-ene (0.260 mL, 1.74 mmol) was added to a solution of the hydrazone in tetrahydrofuran (10 mL) under nitrogen. The mixture was cooled in ice and ethyl 3-chloro-3-oxopropionate (0.223 mL, 1.74 mmol) injected dropwise. The mixture was stirred at room temperature for 2 h, then more diazabicyclo[5.4.0]undec-7-ene (0.520 mL, 3.48 mmol) added and the mixture refluxed under nitrogen for 2 h. After cooling, 0.1M aqueous hydrochloric acid (100 mL) was added and the mixture extracted with ethyl acetate. The extracts were dried ($MgSO_4$), evaporated under reduced pressure and the residue chromatographed (silica gel, 2-5%, then 50% ethyl acetate/hexane) to give the title compound (0.184 g, 19%) as a white solid. 1H NMR (400 MHz, DMSO-$d_6$) δ ppm 1.13-1.21 (m, 2H) 1.26 (t, J=7.07 Hz, 3H) 1.31-1.45 (m, 6H) 1.53-1.91 (m, 12H) 2.74-2.90 (m, 1H) 4.26 (q, J=7.07 Hz, 2H) 4.58-4.72 (m, 1 H) 12.02 (br. s., 1 H).

13b) N-[(2,6-Dicyclohexyl-5-hydroxy-3-oxo-2,3-dihydro-4-pyridazinyl)carbonyl]glycine. A stirred mixture of ethyl 2,6-dicyclohexyl-5-hydroxy-3-oxo-2,3-dihydro-4-pyridazinecarboxylate (0.182 g, 0.522 mmol), anhydrous glycine, sodium salt (0.102 g, 1.05 mmol) and 2-methoxyethanol (5 mL) was heated under reflux under nitrogen for 2 h, then cooled and diluted with water (50 mL). 1M aqueous hydrochloric acid was added slowly until the pH had dropped to 2. The solid was filtered, washed with water and dried to leave the title compound (0.156 g. 79%) as a cream powder. 1H NMR (400 MHz, DMSO-$d_6$) δ ppm 1.12-1.28 (m, 2H) 1.29-1.49 (m, 6H) 1.55-1.97 (m, 12H) 2.80-2.91 (m, 1H) 4.09 (d, J=5.56 Hz, 2H) 4.64-4.85 (m, 1H) 10.35 (t, J=5.31 Hz, 1H) 15.76 (br. s., 1H).

Example 14

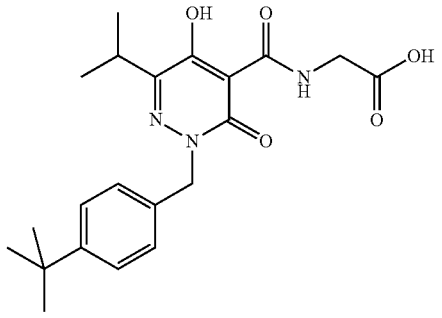

N-{[2-{[4-(1,1-Dimethylethyl)phenyl]methyl}-5-hydroxy-6-(1-methylethyl)-3-oxo-2,3-dihydro-4-pyridazinyl]carbonyl}glycine 14a) Ethyl 5-hydroxy-6-(1-methylethyl)-3-oxo-2,3-dihydro-4-pyridazinecarboxylate. In 3 separate microwave tubes was added Ethyl-3-methyl-2-oxobutyrate (5 g, 34.7 mmol) and Ethyl-malonyl hydrazide (6.08 g, 41.6 mmol) in Ethanol (10 ml) and Acetic Acid (0.5 ml). The reactions were irridatiated at 150° C. for 20 minutes. The crude reaction mixture was evaporated down to give a yellow oil. The 3 crude oils were separately resuspended in 1,4-Dioxane (12 ml) and DBU (7.84 ml, 52.0 mmol) was added. The solution was divided into 2 microwave tubes and the reactions were irridatiated at 150° C. for 20 minutes. The fractions were combined, diluted with water (80 ml) and acidified slowly (over 15 minutes) with 6N HCl to cause a precipitate. The precipitate was collected by filtration and dried to give the product as an off white solid (11.12 g, 46.7 mmol, 44.9% yield). 1H NMR (400 MHz, DMSO-$d_6$) d ppm 12.64 (s, 1H), 12.31 (s, 1 H), 4.28 (q, J=7.16 Hz, 2H), 3.13 (sept, J=6.82 Hz, 1H), 1.27 (t, J=7.07 Hz, 3 H), 1.14 (d, J=6.82 Hz, 6H). MS (ES+) m/e 227 [M+H]+.

14b) Ethyl 2-{[4-(1,1-dimethylethyl)phenyl]methyl}-5-hydroxy-6-(1-methylethyl)-3-oxo-2,3-dihydro-4-pyridazinecarboxylate. Sodium hydride (49 mg, 1.22 mmol) was added to a solution of the compound from example 14a) (110 mg, 0.49 mmol) in N,N-Dimethylformamide (DMF) at 0° C. The reaction was brought to room temperature and stirred for 40 minutes. The temperature was then reduced to 0° C. and 4-tert-butylbenzyl bromide (0.09 mL, 0.49 mmol) was added. The reaction was brought to room temperature and stirred for 3 hours. The solution was diluted with EtOAc and $H_2O$ and the layers separated. 1N HCl was added to the aqueous layer and it was backextracted with EtOAc several times. The combined organic layers were washed with Brine, dried ($MgSO_4$), filtered and concentrated. The product was purified by column chromatography ($SiO_2$, 25-40% EtOAc/Hexanes) to give the title compound (111 mg, 61%). 1H NMR (400 MHz, CHLOROFORM-d) δ ppm 13.29 (s, 1H) 7.31-7.43 (m, 4H) 5.24 (s, 2H) 4.49 (q, J=7.07 Hz, 2 H) 3.25 (sept, J=6.82 Hz, 1H) 1.46 (t, J=7.20 Hz, 3H) 1.31 (s, 9H) 1.27 (d, J=6.82 Hz, 6H).

14c) N-{[2-{[4-(1,1-Dimethylethyl)phenyl]methyl}-5-hydroxy-6-(1-methylethyl)-3-oxo-2,3-dihydro-4-pyridazinyl]carbonyl}glycine. Glycine, sodium salt (38 mg, 0.39 mmol) was added to a solution of the compound from example 14b) (73 mg, 0.20 mmol) in 2-methoxyethanol at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (80 mg, 29%). 1H NMR (400 MHz, CHLOROFORM-d) δ ppm 15.08 (s, 1H) 10.50 (t, J=6.06 Hz, 1H) 7.36 (d, J=1.52 Hz, 4H) 5.27 (s, 2H) 4.24 (d, J=5.81 Hz, 2H) 3.27 (sept, J=6.86 Hz, 1H) 1.31 (s, 9H) 1.28 (d, J=6.82 Hz, 6H).

Example 15

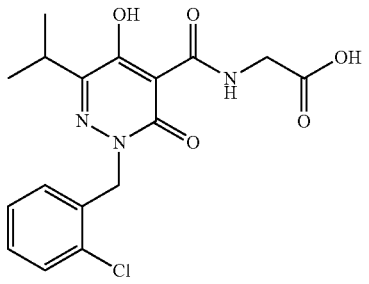

N-{[2-[(2-Chlorophenyl)methyl]-5-hydroxy-6-(1-methylethyl)-3-oxo-2,3-dihydro-4-pyridazinyl] carbonyl}glycine 15a) Ethyl 2-[(2-chlorophenyl)methyl]-5-hydroxy-6-(1-methylethyl)-3-oxo-2,3-dihydro-4-pyridazinecarboxylate. Sodium hydride (37 mg, 0.93 mmol) was added to a solution of the compound from example 14a) (84 mg, 0.37 mmol) in N,N-Dimethylformamide (DMF) (1.5 mL) at 0° C. The reaction was brought to room temperature and stirred for 40 minutes. The temperature was then reduced to 0° C. and 2-chlorobenzyl bromide (48 μL, 0.37 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 30-45% EtOAc/Hexanes) to give the title compound (71 mg, 55%). 1H NMR (400 MHz, CHLOROFORM-d) δ ppm 13.38 (s, 1H) 7.35-7.42 (m, 1H) 7.13-7.26 (m, 3 H) 5.42 (s, 2H) 4.50 (q, J=7.07 Hz, 2H) 3.24 (sept, J=6.82 Hz, 1H) 1.47 (t, J=7.07 Hz, 3H) 1.21 (d, J=6.82 Hz, 6H).

15b) N-{[2-[(2-Chlorophenyl)methyl]-5-hydroxy-6-(1-methylethyl)-3-oxo-2,3-dihydro-4-pyridazinyl]carbonyl}. Glycine, sodium salt (35 mg, 0.36 mmol) was added to a solution of the compound from example 15a) (64 mg, 0.18 mmol) in 2-methoxyethanol at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $CH_2Cl_2$/Hexanes to give the title compound (39 mg, 57%). 1H NMR (400 MHz, CHLOROFORM-d) δ ppm 15.22 (s, 1H) 10.42 (t, J=5.43 Hz, 1H) 7.38-7.45 (m, 1H) 7.19-7.27 (m, 2H) 7.08-7.13 (m, 1H) 5.45 (s, 2H) 4.25 (d, J=5.81 Hz, 2H) 3.27 (sept, J=6.82 Hz, 1 H) 1.22 (d, J=6.82 Hz, 6H).

Example 16

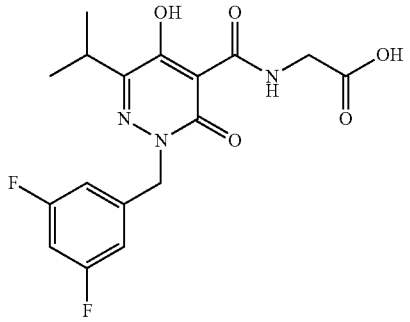

N-{[2-[(3,5-Difluorophenyl)methyl]-5-hydroxy-6-(1-methylethyl)-3-oxo-2,3-dihydro-4-pyridazinyl] carbonyl}glycine 16a) Ethyl-2-[(3,5-difluorophenyl)methyl]-5-hydroxy-6-(1-methylethyl)-3-oxo-2,3-dihydro-4-pyridazinecarboxylate. Sodium hydride (32 mg, 0.80 mmol) was added to a solution of the compound from example 14a) (72 mg, 0.32 mmol) in N,N-Dimethylformamide (DMF) (1.5 mL) at 0° C. The reaction was brought to room temperature and stirred for 40 minutes. The temperature was then reduced to 0° C. and 3,5-difluorobenzyl bromide (0.04 mL, 0.32 mmol) was added. The reaction was brought to room temperature and stirred overnight. Little conversion to product was observed so the reaction was cooled back to 0° C. and additional NaH (10 mg, 0.25) and 3,5-difluorobenzyl bromide (0.01 mL, 0.08 mmol) were added. After several hours, the reaction was quenched with 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 30-45% EtOAc/Hexanes) to give the title compound (34 mg, 30%). 1H NMR (400 MHz, CHLOROFORM-d) δ ppm 13.40 (s, 1H) 6.94 (ddd, J=14.46, 6.63, 2.15 Hz, 2H) 6.73 (tt, J=8.97, 2.27 Hz, 1H) 5.22 (s, 2H) 4.51 (q, J=7.16 Hz, 2H) 3.27 (sept, J=6.86 Hz, 1H) 1.47 (t, J=7.20 Hz, 3H) 1.27 (d, J=6.82 Hz, 6H).

16b) N-{[2-[(3,5-Difluorophenyl)methyl]-5-hydroxy-6-(1-methylethyl)-3-oxo-2,3-dihydro-4-pyridazinyl] carbonyl}glycine. Glycine, sodium salt (18 mg, 0.18 mmol) was added to a solution of the compound from example 16a) (32 mg, 0.09 mmol) in 2-methoxyethanol (0.9 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The solid was redissolved in hot MeOH and filtered. The solvent was removed under reduced pressure to give the title compound as a white solid (26 mg, 75%). 1H NMR (400 MHz, DMSO-$d_6$) δ ppm 15.92 (s, 1H) 12.96 (s, 1H) 10.13 (t, J=5.31 Hz, 1H) 7.17 (m, 1H)

6.95-7.05 (m, 2H) 5.27 (s, 2H) 4.09 (d, J=5.56 Hz, 2H) 3.19 (sept, J=6.78 Hz, 1H) 1.19 (d, J=6.82 Hz, 6H).

Example 17

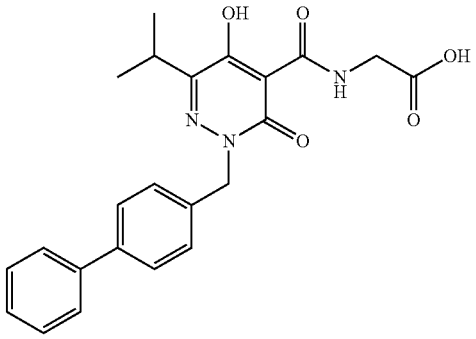

N-{[2-(4-Biphenylylmethyl)-5-hydroxy-6-(1-methylethyl)-3-oxo-2,3-dihydro-4-pyridazinyl]carbonyl}glycine 17a) Ethyl-(4-biphenylylmethyl)-5-hydroxy-6-(1-methylethyl)-3-oxo-2,3-dihydro-4-pyridazinecarboxylate. Sodium hydride (40 mg, 0.99 mmol) was added to a solution of the compound from example 14a) (90 mg, 0.40 mmol) in N,N-Dimethylformamide (DMF) (2.2 mL) at 0° C. The reaction was brought to room temperature and stirred for 45 minutes. The temperature was then reduced to 0° C. and 4-(bromomethyl)-biphenyl (98 mg, 0.40 mmol) was added. The reaction was brought to room temperature and stirred for 3 h. The reaction was quenched with 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 25-45% EtOAc/Hexanes) to give the title compound (130 mg, 83%). 1H NMR (400 MHz, CHLOROFORM-d) δ ppm 13.33 (s, 1H) 7.50-7.61 (m, 6H) 7.41-7.48 (m, 2 H) 7.35 (tt, J=7.33, 1.26 Hz, 1H) 5.31 (s, 2H) 4.50 (q, J=7.07 Hz, 2H) 3.27 (sept, J=6.82 Hz, 1 H) 1.46 (t, J=7.07 Hz, 3H) 1.28 (d, J=6.82 Hz, 6H).

17b) N-{[2-(4-biphenylylmethyl)-5-hydroxy-6-(1-methylethyl)-3-oxo-2,3-dihydro-4-pyridazinyl]carbonyl}glycine. Glycine, sodium salt (18 mg, 0.18 mmol) was added to a solution of the compound from example 17a) (32 mg, 0.09 mmol) in 2-methoxyethanol (0.9 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The solid was redissolved in hot MeOH and filtered. The solvent was removed under reduced pressure to give the title compound as a white solid (26 mg, 75%). 1H NMR (400 MHz, DMSO-$d_6$) δ ppm 15.89 (s, 1H) 12.98 (s, 1H) 10.20 (t, J=4.93 Hz, 1H) 7.64 (d, J=7.83 Hz, 4H) 7.30-7.51 (m, 5H) 5.30 (s, 2H) 4.10 (d, J=5.56 Hz, 2H) 3.13-3.27 (m, 1H) 1.22 (d, J=7.07 Hz, 6 H).

Example 18

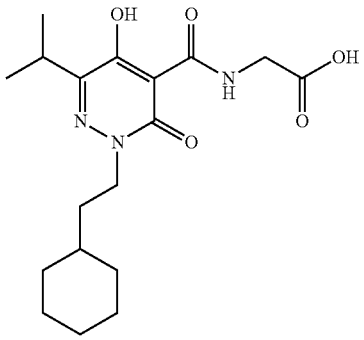

N-{[2-(2-Cyclohexylethyl)-5-hydroxy-6-(1-methylethyl)-3-oxo-2,3-dihydro-4-pyridazinyl]carbonyl}

18a) Ethyl 2-(2-cyclohexylethyl)-5-hydroxy-6-(1-methylethyl)-3-oxo-2,3-dihydro-4-pyridazinecarboxylate. Sodium hydride (40 mg, 0.99 mmol) was added to a solution of the compound from example 14a) (90 mg, 0.40 mmol) in N,N-Dimethylformamide (DMF) (2.2 mL) at 0° C. The reaction was brought to room temperature and stirred for 45 minutes. The temperature was then reduced to 0° C. and 2-cyclohexyl ethyl bromide (0.09 mL, 0.40 mmol) was added. The reaction was brought to room temperature and stirred for 4 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 25-45% EtOAc/Hexanes) to give the title compound (82 mg, 61%). LCMS ($ES^+$) m/z 337.0 ($MH^+$).

18b) N-{[2-(2-Cyclohexylethyl)-5-hydroxy-6-(1-methylethyl)-3-oxo-2,3-dihydro-4-pyridazinyl]carbonyl}. Glycine, sodium salt (47 mg, 0.49 mmol) was added to a solution of the compound from example 18a) (82 mg, 0.24 mmol) in 2-methoxyethanol (1.2 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $Et_2O$/Hexanes to give the title compound as a white solid (40 mg, 45%). 1H NMR (400 MHz, DMSO-$d_6$) δ ppm 15.77 (s, 1H) 12.98 (s, 1H) 10.28 (t, J=5.31 Hz, 1H) 4.04-4.16 (m, 4H) 3.18 (sept, J=6.78 Hz, 1H) 1.47-1.82 (m, 7H) 1.20-1.29 (m, 1H) 1.19 (d, J=6.82 Hz, 6H) 1.06-1.17 (m, 3H) 0.82-0.99 (m, 2H).

Example 19

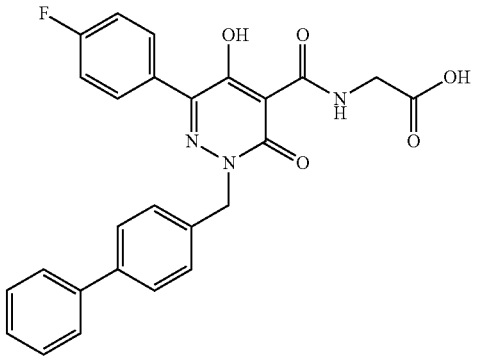

N-{[2-(4-Biphenylylmethyl)-6-(4-fluorophenyl)-5-hydroxy-3-oxo-2,3-dihydro-4-pyridazinyl] carbonyl}glycine 19a) Ethyl (4-fluorophenyl)(oxo)acetate. A solution of diethyl oxylate (1.4 mL, 10.3 mmol) in THF (40 mL) and $Et_2O$ (40 mmol) was cooled to −78° C. 4-Fluorophenyl magnesium bromide (2.0M solution in $Et_2O$, 6.2 mL, 12.4.0 mmol) was dropwise added and the solution stirred under a nitrogen atmosphere for 1.5 h at −78° C. The reaction was brought to 0° C. and quenched with 6N HCl. Additional $Et_2O$ and $H_2O$ were added and the layers separated. The aqueous phase was backextracted with $Et_2O$ several times. The combined organic layers were washed with Brine, dried ($MgSO_4$), filtered and concentrated. The product was purified by column chromatography ($SiO_2$, 5-10% EtOAc/Hexanes) to give the title compound as a pale yellow oil (1.74 g, 86%). 1H NMR (400 MHz, CHLOROFORM-d) δ ppm 8.05-8.15 (m, 2H) 7.16-7.25 (m, 2H) 4.47 (q, J=7.16 Hz, 2H) 1.45 (t, J=7.07 Hz, 3H).

19b) Ethyl 3-{(2Z)-2-[2-(ethyloxy)-1-(4-fluorophenyl)-2-oxoethylidene]hydrazino}-3-oxopropanoate. Ethyl-3-hydrazino-3-oxopropionate (1.31 g, 8.99 mmol) and catalytic AcOH (0.09 mL, 1.50 mmol) were added to a solution of the compound from example 19a) in EtOH (15 mL). The reaction was heated to reflux and stirred overnight. A few spatula tips of MgSO4 were added and the reaction continued to stir for 3 h. The reaction was then cooled to room temperature and filtered. The filtrate was concentrated and azeotroped with Toluene several times. The product was purified by column chromatography ($SiO_2$, 15-45% EtOAc/Hexanes) to give the title compound (1.77 g, 73%). 1H NMR (400 MHz, DMSO-$d_6$) δ ppm 10.63-11.68 (m, 1H) 7.22-7.74 (m, 4H) 4.00-4.49 (m, 4H) 3.40-3.80 (m, 2H) 1.04-1.38 (m, 6H). 19c) Ethyl 6-(4-fluorophenyl)-5-hydroxy-3-oxo-2,3-dihydro-4-pyridazinecarboxylate. KHMDS (1.60 g, 8.02 mmol) was added in several portions to a solution of the compound from example 19b) (1.75 g, 5.35 mmol) in 1,4-dioxane (13 mL) at room temperature. The reaction was heated to reflux and stirred for 2.5 h. The reaction was cooled to room temperature and 1N HCl was added to precipitate the product. The solid was filtered and washed with $H_2O$ and Hexanes to give the title compound (787 mg, 53%). 1H NMR (400 MHz, DMSO-$d_6$) δ ppm 13.03 (s, 1H) 7.72 (dd, J=8.59, 5.81 Hz, 2H) 7.29 (t, J=8.84 Hz, 2H) 4.31 (q, J=7.07 Hz, 2H) 1.29 (t, J=7.07 Hz, 3H).

19d) Ethyl 2-(4-biphenylylmethyl)-6-(4-fluorophenyl)-5-hydroxy-3-oxo-2,3-dihydro-4-pyridazinecarboxylate. Sodium hydride (50 mg, 1.25 mmol) was added to a solution of the compound from example 19c) (139 mg, 0.50 mmol) in N,N-Dimethylformamide (DMF) (2.5 mL) at 0° C. The reaction was brought to room temperature and stirred for 45 minutes. The temperature was then reduced to 0° C. and 4-(bromomethyl)-biphenyl (124 mg, 0.50 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 25-45% EtOAc/Hexanes) give the title compound (69 mg, 31%). LCMS ($ES^+$) m/z 445.2 ($MH^+$).

19e) N-{[2-(4-Biphenylylmethyl)-6-(4-fluorophenyl)-5-hydroxy-3-oxo-2,3-dihydro-4-pyridazinyl] carbonyl}glycine. Glycine, sodium salt (28 mg, 0.29 mmol) was added to a solution of the compound from example 19d) (65 mg, 0.15 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (19 mg, 28%). 1H NMR (400 MHz, DMSO-$d_6$) δ ppm 13.02 (s, 1H) 10.26 (t, J=4.93 Hz, 1H) 7.87 (dd, J=8.72, 5.68 Hz, 2H) 7.60-7.69 (m, 4H) 7.42-7.51 (m, 4H) 7.29-7.40 (m, 3 H) 5.41 (s, 2H) 4.14 (d, J=5.81 Hz, 2H).

Example 20

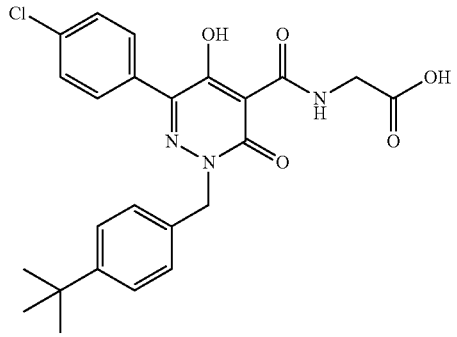

N-[(6-(4-Chlorophenyl)-2-{[4-(1,1-dimethylethyl) phenyl]methyl}-5-hydroxy-3-oxo-2,3-dihydro-4-pyridazinyl)carbonyl]glycine 20a) Ethyl 3-{2-[1-(4-chlorophenyl)-2-(ethyloxy)-2-oxoethylidene]hydrazino}-3-oxopropanoate. A solution of diethyl oxylate (3.4 mL, 25.0 mmol) in THF (50 mL) and $Et_2O$ (50 mmol) was cooled to −78° C. 4-chlorophenyl magnesium bromide (1.0M solution in $Et_2O$, 30 mL, 30.0 mmol) was dropwise added and the solution stirred under a nitrogen atmosphere for 2 h at −78° C. The reaction was brought to 0° C. and quenched with 6N HCl. Additional $Et_2O$ and $H_2O$ were added and the layers separated. The aqueous phase was backextracted with $Et_2O$ several times. The combined organic layers were washed with Brine, dried ($MgSO_4$), filtered and concentrated. The resulting oil was dissolved in EtOH. Ethyl-3-hydrazino-3-oxopropionate (4.27 g, 29.2 mmol) and catalytic AcOH (0.3 mL, 4.87 mmol) were added along with several spatula tips of $MgSO_4$. The reaction was heated to reflux and stirred overnight. The reaction was cooled and solvent removed under reduced pressure. The residue was azeotroped with Toluene several times. The product was purified by column chromatography ($SiO_2$, 15-45% EtOAc/Hexanes) to give the title compound (6.29 g, 76% over 2 steps). 1H NMR (400 MHz. DMSO-$d_6$) δ ppm 10.60-11.75 (m, 1H) 7.21-7.72 (m, 4H) 3.96-4.50 (m, 4H) 3.40-3.82 (m, 2H) 1.02-1.38 (m, 6H).

20b) Ethyl 6-(4-chlorophenyl)-5-hydroxy-3-oxo-2,3-dihydro-4-pyridazinecarboxylate. KHMDS (1.80 g, 9.0 mmol) was added in several portions to a solution of the compound from example 20a) (2.04 g, 6.0 mmol) in 1,4-dioxane at room temperature. The reaction was heated to reflux and stirred for 5 h. The reaction was cooled back to room temperature and 1N HCl was added to precipitate the product. $CH_2Cl_2$ and $H_2O$ were added and the layers separated. The aqueous phase was backextracted with $CH_2Cl_2$ several times. The combined organic layers were washed with Brine, dried ($MgSO_4$), filtered and concentrated to give a pale yellow solid. The flask was cooled and $Et_2O$ added. The product was filtered to give the title compound as a white solid (1.07 g, 60%). LCMS ($ES^+$) m/z 294.8 ($MH^+$).

20c) Ethyl 6-(4-chlorophenyl)-2-{[4-(1,1-dimethylethyl) phenyl]methyl}-5-hydroxy-3-oxo-2,3-dihydro-4-pyridazinecarboxylate. Sodium hydride (50 mg, 1.25 mmol) was added to a solution of the compound from example 20b) (147 mg, 0.50 mmol) in N,N-Dimethylformamide (DMF) at 0° C. The reaction was brought to room temperature and stirred for 45 minutes. The temperature was then reduced to 0° C. and 4-tert-butylbenzyl bromide (0.09 mL, 0.50 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) then triturating with cold $Et_2O$ to give the title compound as a white foam (132 mg, 60%). LCMS ($ES^+$) m/z 441.1 ($MH^+$).

20d) N-[(6-(4-Chlorophenyl)-2-{[4-(1,1-dimethylethyl) phenyl]methyl}-5-hydroxy-3-oxo-2,3-dihydro-4-pyridazinyl)carbonyl]glycine. Glycine, sodium salt (55 mg, 0.57 mmol) was added to a solution of the compound from example 20c) (125 mg, 0.28 mmol) in 2-methoxyethanol at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $CH_2Cl_2$/Hexanes to give the title compound as a white solid (69 mg, 52%). 1H NMR (400 MHz, DMSO-$d_6$) δ ppm 10.24 (t, J=6.06 Hz, 1H) 7.84 (d, J=8.59 Hz, 2 H) 7.57 (d, J=8.59 Hz, 2H) 7.33-7.41 (m, 2H) 7.26-7.33 (m, 2H) 5.32 (s, 2H) 4.12 (d, J=5.81 Hz, 2H) 1.25 (s, 9H).

Example 21

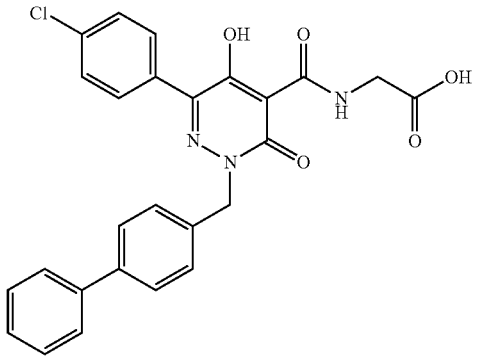

N-{[2-(4-Biphenylylmethyl)-6-(4-chlorophenyl)-5-hydroxy-3-oxo-2,3-dihydro-4-pyridazinyl] carbonyl}glycine 21a) Ethyl 2-(4-biphenylylmethyl)-6-(4-chlorophenyl)-5-hydroxy-3-oxo-2,3-dihydro-4-pyridazinecarboxylate.

Sodium hydride (50 mg, 1.25 mmol) was added to a solution of the compound from example 20b) (147 mg, 0.50 mmol) in N,N-Dimethylformamide (DMF) (2.5 mL) at 0° C. The reaction was brought to room temperature and stirred for 45 minutes. The temperature was then reduced to 0° C. and 4-(bromomethyl)-biphenyl (124 mg, 0.50 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) give the title compound (135 mg, 59%). 1H NMR (400 MHz, DMSO-$d_6$) δ ppm 7.74 (ddd, J=8.91, 2.53, 2.21 Hz, 2H) 7.60-7.67 (m, 4H) 7.55 (ddd, J=9.09, 2.53, 2.27 Hz, 2H) 7.40-7.50 (m, 4H) 7.36 (tt, J=7.33, 1.26 Hz, 1H) 5.30 (s, 2H) 4.30 (q, J=7.07 Hz, 2H) 1.28 (t, J=7.20 Hz, 3H).

21b) N-{[2-(4-Biphenylylmethyl)-6-(4-chlorophenyl)-5-hydroxy-3-oxo-2,3-dihydro-4-pyridazinyl] carbonyl}glycine. Glycine, sodium salt (53 mg, 0.55 mmol) was added to a solution of the compound from example 21a) (126 mg, 0.27 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $CH_2Cl_2$/Hexanes to give the title compound (90 mg, 67%). 1H NMR (400 MHz, DMSO-$d_6$) δ ppm 13.03 (s, 1H) 10.25 (t, J=5.43 Hz, 1H) 7.80-7.89 (m, 2H) 7.65

(ddd, J=6.88, 3.09, 1.64 Hz, 4H) 7.58 (ddd, J=9.09, 2.53, 2.27 Hz, 2H) 7.42-7.50 (m, 4H) 7.32-7.40 (m, 1H) 5.41 (s, 2H) 4.14 (d, J=5.56 Hz, 2H).

Example 22

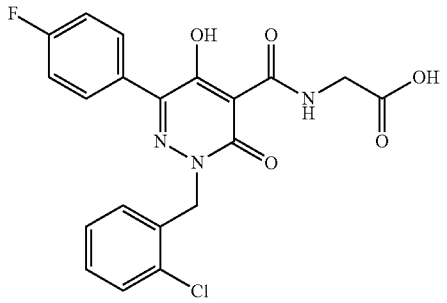

N-{[2-[(2-Chlorophenyl)methyl]-6-(4-fluorophenyl)-5-hydroxy-3-oxo-2,3-dihydro-4-pyridazinyl] carbonyl}glycine 22a) Ethyl 2-[(2-chlorophenyl)methyl]-6-(4-fluorophenyl)-5-hydroxy-3-oxo-2,3-dihydro-4-pyridazinecarboxylate. Sodium hydride (83 mg, 2.08 mmol) was added to a solution of the compound from example 19c) (232 mg, 0.83 mmol) in N,N-Dimethylformamide (DMF) (4 mL) at 0° C. The reaction was brought to room temperature and stirred for 45 minutes. The temperature was then reduced to 0° C. and 2-chlorobenzyl bromide (0.11 mL, 0.83 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) to give the title compound (165 mg, 49%). 1H NMR (400 MHz, DMSO-$d_6$) δ ppm 12.72 (br. s., 1H) 7.66-7.76 (m, 2H) 7.44-7.54 (m, 1H) 7.22-7.39 (m, 4H) 7.18 (dd, J=6.82, 2.27 Hz, 1H) 5.34 (s, 2H) 4.31 (q, J=7.07 Hz, 2H) 1.28 (t, J=7.07 Hz, 3H).

22b) N-{[2-[(2-Chlorophenyl)methyl]-6-(4-fluorophenyl)-5-hydroxy-3-oxo-2,3-dihydro-4-pyridazinyl] carbonyl}glycine. Glycine, sodium salt (71 mg, 0.73 mmol) was added to a solution of the compound from example 22a) (147 mg, 0.37 mmol) in 2-methoxyethanol (2 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was redissolved in hot $CH_2Cl_2$, dried ($MgSO_4$) and filtered. The solution was cooled to 0° C. and Hexanes added to precipitate the product. The product was filtered to give the title compound as a pale pink solid (107 mg, 68%). 1H NMR (400 MHz, DMSO-$d_6$) δ ppm 13.03 (s, 1H) 10.20 (t, J=4.29 Hz, 1H) 7.76-7.86 (m, 2H) 7.52 (dd, J=7.58, 1.52 Hz, 1H) 7.27-7.41 (m, 4H) 7.20-7.27 (m, 1H) 5.45 (s, 2H) 4.14 (d, J=5.56 Hz, 2H).

Example 23

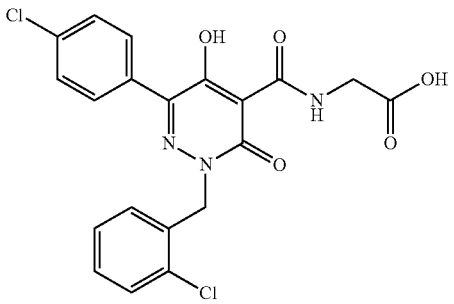

N-({6-(4-Chlorophenyl)-2-[(2-chlorophenyl)methyl]-5-hydroxy-3-oxo-2,3-dihydro-4-pyridazinyl}carbonyl)glycine 23a) Ethyl 6-(4-chlorophenyl)-2-[(2-chlorophenyl)methyl]-5-hydroxy-3-oxo-2,3-dihydro-4-pyridazinecarboxylate. Sodium hydride (85 mg, 2.14 mmol) was added to a solution of the compound from example 20b) (250 mg, 0.85 mmol) in N,N-Dimethylformamide (DMF) (4 mL) at 0° C. The reaction was brought to room temperature and stirred for 45 minutes. The temperature was then reduced to 0° C. and 2-chlorobenzyl bromide (0.11 mL, 0.85 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) then triturating with cold $Et_2O$ to give the title compound as a white solid (187 mg, 53%). 1H NMR (400 MHz, DMSO-$d_6$) δ ppm 7.70 (ddd, J=9.09, 2.53, 2.27 Hz, 2H) 7.47-7.55 (m, 3H) 7.28-7.38 (m, 2H) 7.14-7.20 (m, 1H) 5.34 (s, 2 H) 4.30 (q, J=7.16 Hz, 2H) 1.28 (t, J=7.07 Hz, 3H).

23b) N-({6-(4-Chlorophenyl)-2-[(2-chlorophenyl)methyl]-5-hydroxy-3-oxo-2,3-dihydro-4-pyridazinyl}carbonyl)glycine. Glycine, sodium salt (83 mg, 0.85 mmol) was added to a solution of the compound from example 23a) (179 mg, 0.43 mmol) in 2-methoxyethanol at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (153 mg, 80%). 1H NMR (400 MHz, DMSO-$d_6$) δ ppm 13.03 (s, 1H) 10.19 (t, J=4.80 Hz, 1H) 7.74-7.83 (m, 2H) 7.55 (ddd, J=8.91, 2.53, 2.21 Hz, 2H) 7.52 (dd, J=7.71, 1.39 Hz, 1H) 7.28-7.39 (m, 2H) 7.21-7.26 (m, 1H) 5.45 (s, 2H) 4.13 (d, J=5.81 Hz, 2H).

Example 24

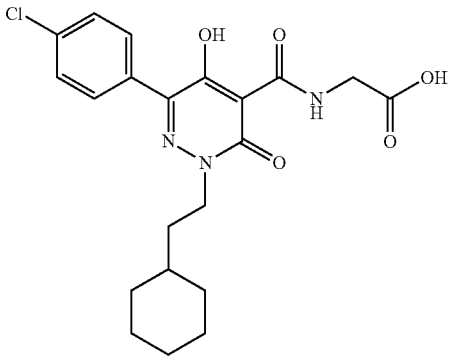

N-{[6-(4-Chlorophenyl)-2-(2-cyclohexylethyl)-5-hydroxy-3-oxo-2,3-dihydro-4-pyridazinyl] carbonyl}glycine 24a) Ethyl 6-(4-chlorophenyl)-2-(2-cyclohexylethyl)-5-hydroxy-3-oxo-2,3-dihydro-4-pyridazinecarboxylate.

Sodium hydride (85 mg, 2.14 mmol) was added to a solution of the compound from example 20b) (250 mg, 0.85 mmol) in N,N-Dimethylformamide (DMF) (4 mL) at 0° C. The reaction was brought to room temperature and stirred for 45 minutes. The temperature was then reduced to 0° C. and 2-cyclohexyl ethyl bromide (0.13 mL, 0.85 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) then dried under high vacuum to give the title compound as a pale yellow solid (187 mg, 54%). LCMS ($ES^+$) m/z 405.0 ($MH^+$).

24b) N-{[6-(4-Chlorophenyl)-2-(2-cyclohexylethyl)-5-hydroxy-3-oxo-2,3-dihydro-4-pyridazinyl] carbonyl}glycine. Glycine, sodium salt (85 mg, 0.87 mmol) was added to a solution of the compound from example 24a) (177 mg, 0.44 mmol) in 2-methoxyethanol (2 mL) at room temperature. The reaction was heated to reflux and stirred for 3 h. The reaction was cooled back to room temperature and $H_2O$ was added. The solution was filtered and 1N HCl was added to precipitate the product. The solid was filtered and washed with $H_2O$ and Hexanes to give the title compound (117 mg, 62%). 1H NMR (400 MHz, DMSO-$d_6$) δ ppm 13.02 (s, 1H) 10.32 (t, J=4.93 Hz, 1H) 7.82 (d, J=8.59 Hz, 2H) 7.57 (ddd, J=8.84, 2.53, 2.27 Hz, 2H) 4.16-4.23 (m, 2H) 4.15 (d, J=5.81 Hz, 2H) 1.55-1.81 (m, 7H) 1.10-1.41 (m, 4H) 0.84-1.02 (m, 2 H).

Example 25

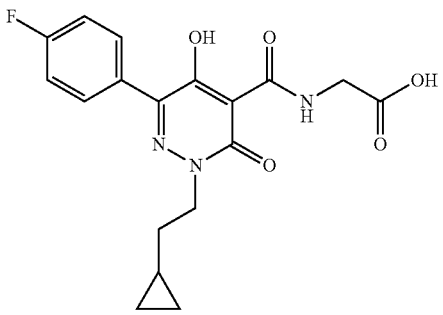

N-{[2-(2-Cyclopropylethyl)-6-(4-fluorophenyl)-5-hydroxy-3-oxo-2,3-dihydro-4-pyridazinyl] carbonyl}glycine 25a) Ethyl 2-(2-cyclopropylethyl)-6-(4-fluorophenyl)-5-hydroxy-3 -oxo-2,3-dihydro-4-pyridazinecarboxylate.

Sodium hydride (40 mg, 1.00 mmol) was added to a solution of the compound from example 19c) (139 mg, 0.50 mmol) in N,N-Dimethylformamide (DMF) (2.5 mL) at 0° C. The reaction was brought to room temperature and stirred for 45 minutes. The temperature was then reduced to 0° C. and cyclopropylethyl iodide (119 mg, 0.50 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) to give the title compound (47 mg, 27%). LCMS ($ES^+$) m/z 346.8 ($MH^+$).

25b) N-{[2-(2-Cyclopropylethyl)-6-(4-fluorophenyl)-5-hydroxy-3-oxo-2,3-dihydro-4-pyridazinyl] carbonyl}glycine. Glycine, sodium salt (26 mg, 0.27 mmol) was added to a solution of the compound from example 25a) (47 mg, 0.14 mmol) in 2-methoxyethanol (0.8 mL) at room temperature. The reaction was heated to reflux and stirred for 3 h. The reaction was cooled back to room temperature and 1N HCl was added to precipitate the product. The solid was filtered and washed with Hexanes and $Et_2O$ to give the title compound as a pale pink solid (21 mg, 40%). 1H NMR (400 MHz, DMSO-$d_6$) δ ppm 13.02 (s, 1H) 10.28-10.39 (m, 1H) 7.79-7.88 (m, 2H) 7.29-7.38 (m, 2H) 4.25 (t, J=7.07 Hz, 2H)

4.15 (d, J=5.56 Hz, 2H) 1.68 (q, J=7.07 Hz, 2H) 0.65-0.79 (m, 1H) 0.40 (ddd, J=7.89, 5.75, 4.04 Hz, 2H) 0.02 (td, J=5.24, 4.17 Hz, 2H).

Example 26

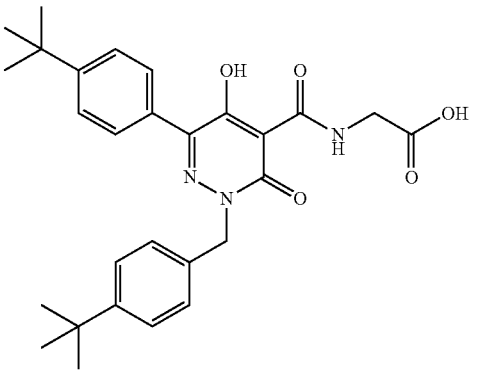

N-[(6-[4-(1,1-Dimethylethyl)phenyl]-2-{[4-(1,1-dimethylethyl)phenyl]methyl}-5-hydroxy-3-oxo-2,3-dihydro-4-pyridazinyl)carbonyl]glycine 26a) Ethyl[4-(1,1-dimethylethyl)phenyl](oxo)acetate. To a solution of 4-bromo-tert-butylbenzene (0.70 mL, 5.0 mmol) in THF (20 mL) was dropwise added n-BuLi (2.87 M solution in Hexanes, 1.74 mL, 5.0 mmol) at −78° C. under a nitrogen atmosphere. After stirring for 1 h diethyl oxylate (0.68 mL, 5.0 mmol) was added. The reaction stirred for 1 h at −78° C. and then 1 N HCl was added. The solution was diluted with $H_2O$ and EtOAc and the layers separated. The aqueous phase was backextracted with EtOAc several times. The combined organic layers were washed with Brine, dried ($MgSO_4$), filtered and concentrated. The product was purified by column chromatography ($SiO_2$, 5-10% EtOAc/Hexanes) to give the title compound (334 mg, 29%). 1H NMR (400 MHz, CHLOROFORM-d) δ ppm 7.97 (dt, J=8.65, 2.12 Hz, 2H) 7.55 (dt, J=8.84, 2.02 Hz, 2H) 4.47 (q, J=7.07 Hz, 2H) 1.45 (t, J=7.20 Hz, 3H) 1.37 (s, 9H).

26b) Ethyl 3-{2-[1-[4-(1,1-dimethylethyl)phenyl]-2-(ethyloxy)-2-oxoethylidene]hydrazino}-3-oxopropanoate. Ethyl-3-hydrazino-3-oxopropionate (419 mg, 2.87 mmol) and catalytic AcOH (0.03 mL, 0.48 mmol) were added to a solution of the compound from example 26a) (560 mg, 2.39 mmol) in EtOH (10 mL). Several spatula tips of $MgSO_4$ were added and the reaction stirred at reflux overnight. The reaction was then cooled to room temperature and filtered. The filtrate was concentrated and azeotroped with Toluene several times. The product was purified by column chromatography ($SiO_2$, 10-45% EtOAc/Hexanes) to give the title compound (581 mg, 67%). 1H NMR (400 MHz, DMSO-$d_6$) δ ppm 10.39-11.61 (m, 1H) 7.17-7.59 (m, 4H) 3.97-4.48 (m, 4 H) 50 3.45-3.76 (m, 2H) 1.11-1.36 (m, 15H).

26c) Ethyl 6-[4-(1,1-dimethylethyl)phenyl]-5-hydroxy-3-oxo-2,3-dihydro-4-pyridazinecarboxylate. KHMDS (466 mg, 2.33 mmol) was added in several portions to a solution of the compound from example 26b) (564 mg, 1.56 mmol) in 1,4-dioxane (4 mL) at room temperature. The reaction was heated to reflux and stirred for 3 h. The reaction was cooled to room temperature and solvent removed under reduced pressure. 1N HCl was added to precipitate the product. The solid was filtered and washed with $H_2O$, Hexanes and $Et_2O$ to give the title compound (220 mg, 45%). 1H NMR (400 MHz, DMSO-$d_6$) δ ppm 13.03 (s, 1H) 12.59 (br. s., 1H) 7.57-7.62 (m, 2H) 7.47 (dt, J=8.59, 2.02 Hz, 2H) 4.32 (q, J=7.07 Hz, 2H) 1.31 (s, 9H) 1.26-1.34 (m, 3H).

26d) Ethyl 6-[4-(1,1-dimethylethyl)phenyl]-2-{[4-(1,1-dimethylethyl)phenyl]methyl}-5-hydroxy-3-oxo-2,3-dihydro-4-pyridazinecarboxylate. Sodium hydride (32 mg, 0.79 mmol) was added to a solution of the compound from example 26c) (100 mg, 0.32 mmol) in N,N-Dimethylformamide (DMF) at 0° C. The reaction was brought to room temperature and stirred for 45 minutes. The temperature was then reduced to 0° C. and 4-tert-butylbenzyl bromide (0.06 mL, 0.32 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-45% EtOAc/Hexanes) give the title compound as a white foam (110 mg, 75%). LCMS ($ES^+$) m/z 463.2 ($MH^+$).

26e) N-[(6-[4-(1,1-Dimethylethyl)phenyl]-2-{[4-(1,1-dimethylethyl)phenyl]methyl}-5-hydroxy-3-oxo-2,3-dihydro-4 -pyridazinyl)carbonyl]glycine. Glycine, sodium salt (43 mg, 0.44 mmol) was added to a solution of the compound from example 26d) (102 mg, 0.22 mmol) in 2-methoxyethanol (1.4 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes which partially dissolved the product. EtOAc was added and the layers separated. The aqueous layer was backextracted with EtOAc several times. The combined organic layers were washed with Brine, dried ($MgSO_4$), filtered and concentrated to give the title compound as a tan solid (57 mg, 53%). 1H NMR (400 MHz, DMSO-$d_6$) δ ppm 16.29 (s, 1H) 13.00 (s, 1H) 10.27 (t, J=5.56 Hz, 1H) 7.72 (d, J=8.59 Hz, 2H) 7.51 (d, J=8.59 Hz, 2H) 7.34-7.41 (m, 2 H) 7.27-7.33 (m, 2 H) 5.31 (s, 2H) 4.13 (d, J=5.81 Hz, 2H) 1.32 (s, 9H) 1.25 (s, 9H).

Example 27

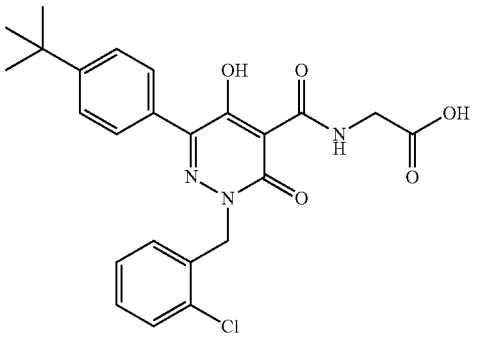

N-({2-[(2-Chlorophenyl)methyl]-6-[4-(1,1-dimethylethyl)phenyl]-5-hydroxy-3-oxo-2,3-dihydro-4-pyridazinyl}carbonyl)glycine 27a) Ethyl 2-[(2-chlorophenyl)methyl]-6-[4-(1,1-dimethylethyl)phenyl]-5-hydroxy-3-oxo-2,3-dihydro-4-pyridazinecarboxylate. Sodium hydride (37 mg, 0.92 mmol) was added to a solution of the compound from example 26c) (117 mg, 0.37 mmol) in N,N-Dimethylformamide (DMF) (1.5 mL) at 0° C. The reaction was brought to room temperature and stirred for 45 minutes. The temperature was then reduced to 0° C. and 2-chlorobenzyl bromide (0.05 mL, 0.37 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 0-4% MeOH/$CH_2Cl_2$) then dried under high vacuum give the title compound as a white foam (125 mg, 77%). 1H NMR (400 MHz, DMSO-$d_6$) δ ppm 12.64 (br. s., 1H) 7.59 (ddd, J=8.72, 2.15, 2.02 Hz, 2H) 7.43-7.52 (m, 3H) 7.28-7.38 (m, 2 H) 7.13-7.21 (m, 1H) 5.34 (s, 2H) 4.31 (q, J=7.07 Hz, 2H) 1.30 (s, 9H) 1.24-1.32 (m, 3H).

27b) N-({2-[(2-Chlorophenyl)methyl]-6-[4-(1,1-dimethylethyl)phenyl]-5-hydroxy-3-oxo-2,3-dihydro-4-pyridazinyl}carbonyl)glycine. Glycine, sodium salt (52 mg, 0.54 mmol) was added to a solution of the compound from example 27a) (118 mg, 0.27 mmol) in 2-methoxyethanol at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $CH_2Cl_2$/Hexanes to give the title compound as a white solid (100 mg, 79%). 1H NMR (400 MHz, DMSO-$d_6$) δ ppm 13.01 (s, 1H) 10.22 (t, J=5.18 Hz, 1H) 7.64-7.71 (m, 2H) 7.46-7.54 (m, 3H) 7.28-7.40 (m, 2H) 7.20-7.26 (m, 1H) 5.45 (s, 2H) 4.14 (d, J=5.56 Hz, 2H) 1.30 (s, 9H).

Example 28

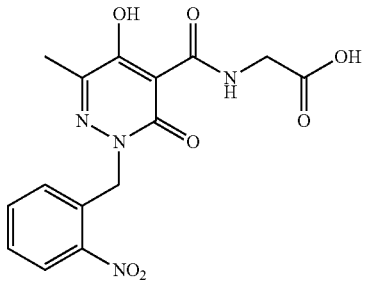

N-({5-Hydroxy-6-methyl-2-[(2-nitrophenyl)methyl]-3-oxo-2,3-dihydro-4-pyridazinyl}carbonyl)glycine 28a) Ethyl 3-{(2Z)-2-[2-(ethyloxy)-1-methyl-2-oxoethylidene]hydrazino}-3-oxopropanoate. Ethyl-3-hydrazino-3-oxopropionate (0.73 g, 5.00 mmol) and catalytic AcOH (0.06 mL, 1.05 mmol) were added to a solution of ethyl pyruvate (0.55 mL, 5.00 mmol) in $CH_2Cl_2$ (20 mL). The reaction stirred overnight at room temperature. The solvent was removed under reduced pressure and the resulting solid was azeotroped with Toluene several times. The product was purified by column chromatography ($SiO_2$, 1-5% MeOH/$CH_2Cl_2$) to give the title compound as a white solid (1.29 g, 63%). 1H NMR (400 MHz, DMSO-$d_6$) δ ppm 10.64-11.20 (m, 1H) 4.03-4.28 (m, 4 H) 3.47-3.68 (m, 2H) 1.96-2.11 (m, 3H) 1.12-1.32 (m, 6H).

28b) Ethyl 5-hydroxy-6-methyl-3-oxo-2,3-dihydro-4-pyridazinecarboxylate. DBU (1.6 mL, 10.73 mmol) was dropwise added to a solution of the compound from example 28a) (1.31 g, 5.36 mmol) in 1,4-dioxane (12 mL) at room temperature. The reaction was heated to reflux and stirred overnight. The reaction was cooled to room temperature and solvent removed under reduced pressure. The product was purified by pushing through a silica plug with MeOH to give the title compound (348 mg, 33%). 1H NMR (400 MHz, DMSO-$d_6$) δ ppm 1.27 (t, J=7.20 Hz, 3H) 2.17 (s, 3H) 4.27 (q, J=7.24 Hz, 2H) 12.13 (br. s., 1H) 12.59 (s, 1H).

28c) Ethyl 5-hydroxy-6-methyl-2-[(2-nitrophenyl)methyl]-3-oxo-2,3-dihydro-4-pyridazinecarboxylate. Sodium hydride (50 mg, 1.26 mmol) was added to a solution of the compound from example 28b) (100 mg, 0.50 mmol) in N,N-Dimethylformamide (DMF) (2 mL) at 0° C. The reaction was brought to room temperature and stirred for 45 minutes. The temperature was then reduced to 0° C. and 2-nitrobenzyl bromide (109 mg, 0.50 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 0-6% MeOH/$CH_2Cl_2$) to give the title compound as an orange oil (83 mg, 50%). 1H NMR (400 MHz, DMSO-$d_6$) δ ppm 12.28 (s, 1H) 8.08 (dd, J=8.08, 1.26 Hz, 1H) 7.70 (td, J=7.64, 1.39 Hz, 1H) 7.53-7.61 (m, 1H) 7.18 (dd, J=7.71, 0.88 Hz, 1H) 5.45 (s, 2H) 4.26 (q, J=7.24 Hz, 2H) 2.20 (s, 3H) 1.25 (t, J=7.07 Hz, 3H).

28d) N-({5-Hydroxy-6-methyl-2-[(2-nitrophenyl)methyl]-3-oxo-2,3-dihydro-4-pyridazinyl}carbonyl)glycine. Glycine, sodium salt (43 mg, 0.45 mmol) was added to a solution of the compound from example 28c) (75 mg, 0.23 mmol) in 2-methoxyethanol at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $CH_2Cl_2$/Hexanes to give the title compound as a brown solid (20 mg, 24%). 1H NMR (400 MHz, DMSO-$d_6$) δ ppm 15.75 (s, 1H) 12.99 (s, 1H) 10.03 (t, J=5.18 Hz, 1H) 8.11 (dd, J=8.08, 1.26 Hz, 1H) 7.69 (td, J=7.64, 1.39 Hz, 1H) 7.59 (td, J=7.71, 1.26 Hz, 1H) 7.23 (dd, J=7.83, 1.01 Hz, 1H) 5.56 (s, 2H) 4.09 (d, J=5.81 Hz, 2H) 2.24 (s, 3H).

Example 29

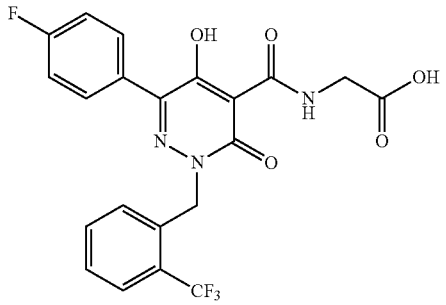

N-[(6-(4-Fluorophenyl)-5-hydroxy-3-oxo-2-{[2-(trifluoromethyl)phenyl]methyl}-2,3-dihydro-4-pyridazinyl)carbonyl]glycine 29a) Ethyl 6-(4-fluorophenyl)-5-hydroxy-3-oxo-2-{[2-(trifluoromethyl)phenyl]methyl}-2,3-dihydro-4-pyridazinecarboxylate. Sodium hydride (40 mg, 1.01 mmol) was added to a solution of the compound from example 19c) (112 mg, 0.40 mmol) in N,N-Dimethylformamide (DMF) at 0° C. The reaction was brought to room temperature and stirred for 45 minutes. The temperature was then reduced to 0° C. and 2-(trifluoromethyl)-benzyl bromide (96 mg, 0.40 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$) to give the title compound (170 mg, 97%). LCMS ($ES^+$) m/z 437.0 ($MH^+$).

29b) N-[(6-(4-Fluorophenyl)-5-hydroxy-3-oxo-2-{[2-(trifluoromethyl)phenyl]methyl}-2,3-dihydro-4-pyridazinyl) carbonyl]glycine. Glycine, sodium salt (68 mg, 0.70 mmol) was added to a solution of the compound from example 29a) (153 mg, 0.35 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$, Hexanes and $Et_2O$ to give the title compound as a pale pink solid (71 mg, 44%). 1H NMR (400 MHz, DMSO-$d_6$) δ ppm 15.75 (s, 1H) 12.99 (s, 1H) 10.03 (t, J=5.18 Hz, 1H) 8.11 (dd, J=8.08, 1.26 Hz, 1H) 7.69 (td, J=7.64, 1.39 Hz, 1H) 7.59 (td, J=7.71, 1.26 Hz, 1H) 7.23 (dd, J=7.83, 1.01 Hz, 1H) 5.56 (s, 2 H) 4.09 (d, J=5.81 Hz, 2H) 2.24 (s, 3H).

Example 30

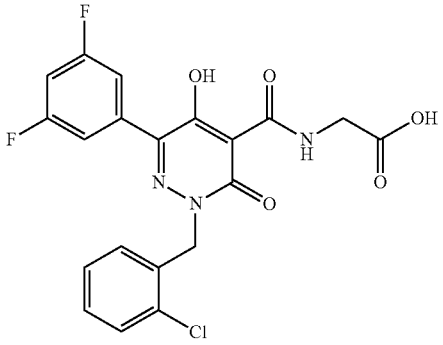

N-{[2-[(2-Chlorophenyl)methyl]-6-(3,5-difluorophenyl)-5-hydroxy-3-oxo-2,3-dihydro-4-pyridazinyl] carbonyl}glycine 30a) Ethyl 3-{2-[1-(3,5-difluorophenyl)-2-(ethyloxy)-2-oxoethylidene]hydrazino}-3-oxopropanoate. A solution of diethyl oxylate (2.0 mL, 15.0 mmol) in THF (30 mL) and $Et_2O$ (30 mmol) was cooled to −78° C. 3,5-difluorophenyl magnesium bromide (0.5 M solution in THF, 36 mL, 18.0 mmol) was dropwise added and the solution stirred under a nitrogen atmosphere for 1.5 h at −78° C. The reaction was brought to 0° C. and quenched with 6N HCl. Additional $Et_2O$ and $H_2O$ were added and the layers separated. The aqueous phase was backextracted with $Et_2O$ several times. The combined organic layers were washed with Brine, dried ($MgSO_4$), filtered and concentrated. The product was purified by column chromatography ($SiO_2$, 15-45% EtOAc/Hexanes). The crude oil was redissolved in EtOH (40 mL). Ethyl-3-hydrazino-3-oxopropionate (2.63 g, 18.0 mmol) and catalytic AcOH (0.2 mL, 3.00 mmol) were added along with a few spatula tips of $MgSO_4$. The reaction was heated to reflux and stirred overnight. The reaction was then cooled to room temperature and filtered. The filtrate was concentrated and azeotroped with Toluene several times. The product was purified by column chromatography ($SiO_2$, 10-40% EtOAc/Hexanes) to give the title compound (1.01 g, 20% over 2 steps). 1H NMR (400 MHz, DMSO-$d_6$) δ ppm 10.62-11.95 (m, 1H) 6.85-7.50 (m, 3H) 3.99-4.51 (m, 4H) 3.42-3.86 (m, 2H) 0.95-1.41 (m, 6H).

30b) Ethyl 6-(3,5-difluorophenyl)-5-hydroxy-3-oxo-2,3-dihydro-4-pyridazinecarboxylate. KHMDS (0.80 g, 4.01 mmol) was added in several portions to a solution of the compound from example 30a) (0.915 g, 2.67 mmol) in 1,4-dioxane (15 mL) at room temperature. The reaction was heated to reflux and stirred for 1.5 h. The reaction was cooled to room temperature and diluted with EtOAc and $H_2O$. 1N HCl was added to neutralize the solution. The layers were separated and the aqueous phase was backextracted with EtOAc several times. The combined organic layers were washed with Brine, dried ($MgSO_4$), filtered and concentrated to give a pale yellow residue. The flask was cooled and $Et_2O$ was added. The product was filtered to give the title compound as a white solid (332 mg, 42%). 1H NMR (400 MHz, DMSO-$d_6$) δ ppm 13.19 (s, 1H) 7.31-7.45 (m, 3H) 4.31 (q, J=7.07 Hz, 2H) 1.29 (t, J=7.07 Hz, 3H).

30c) Ethyl 2-[(2-chlorophenyl)methyl]-6-(3,5-difluorophenyl)-5-hydroxy-3-oxo-2,3-dihydro-4-pyridazinecarboxylate. Sodium hydride (38 mg, 0.95 mmol) was added to a solution of the compound from example 30b) (113 mg, 0.38 mmol) in N,N-Dimethylformamide (DMF) (1.8 mL) at 0° C. The reaction was brought to room temperature and stirred for 45 minutes. The temperature was then reduced to 0° C. and 2-chlorobenzyl bromide (0.05 mL, 0.38 mmol) was added. The reaction was brought to room temperature and stirred for 3 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 40-65% EtOAc/Hexanes) give the title compound (124 mg, 78%). 1H NMR (400 MHz, DMSO-$d_6$) δ ppm 7.47-7.55 (m, 1H) 7.28-7.45 (m, 5H) 7.16-7.24 (m, 1H) 5.36 (s, 2H) 4.30 (q, J=7.24 Hz, 2H) 1.28 (t, J=7.07 Hz, 3H).

30d) N-{[2-[(2-Chlorophenyl)methyl]-6-(3,5-difluorophenyl)-5-hydroxy-3-oxo-2,3-dihydro-4-pyridazinyl] carbonyl}glycine. Glycine, sodium salt (48 mg, 0.50 mmol) was added to a solution of the compound from example 30c) (105 mg, 0.25 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (81 mg, 72%). 1H NMR (400 MHz, DMSO-$d_6$) δ ppm 13.03 (s, 1H) 10.13-10.21 (m, 1H) 7.47-7.55 (m, 3H) 7.37-7.44 (m, 1H) 7.34 (ddd, J=14.78, 7.45, 1.77 Hz, 2 H) 7.23-7.29 (m, 1H) 5.47 (s, 2H) 4.13 (d, J=5.56 Hz, 2H).

Example 31

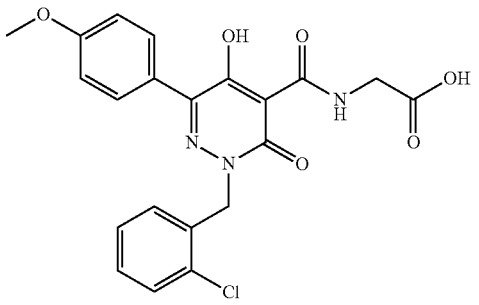

N-({2-[(2-Chlorophenyl)methyl]-5-hydroxy-6-[4-(methyloxy)phenyl]-3-oxo-2,3-dihydro-4-pyridazinyl}carbonyl)glycine 31a) Ethyl[4-(methyloxy)phenyl](oxo)acetate. A solution of diethyl oxylate (2.0 mL, 15.0 mmol) in THF (40 mL) and $Et_2O$ (40 mmol) was cooled to −78° C. 4-methoxyphenyl magnesium bromide (0.5 M solution in THF, 36 mL, 18.0 mmol) was dropwise added and the solution stirred under a nitrogen atmosphere for 1.5 h at −78° C. The reaction was brought to 0° C. and quenched with 6N HCl. Additional $Et_2O$ and $H_2O$ were added and the layers separated. The aqueous phase was backextracted with $Et_2O$ several times. The combined organic layers were washed with Brine, dried ($MgSO_4$), filtered and concentrated. The product was purified by column chromatography ($SiO_2$, 10-20% EtOAc/Hexanes) to give the title compound as a pale yellow oil (2.68 g, 84%). 1H NMR (400 MHz, CHLOROFORM-d) δ ppm 8.02 (ddd, J=9.47, 2.78, 2.40 Hz, 2H) 7.00 (ddd, J=9.47, 2.78, 2.40 Hz, 2H) 4.46 (q, J=7.24 Hz, 2H) 3.92 (s, 3H) 1.44 (t, J=7.07 Hz, 3H).

31b) Ethyl 3-(2-{2-(ethyloxy)-1-[4-(methyloxy)phenyl]-2-oxoethylidene}hydrazino)-3-oxopropanoate. Ethyl-3-hydrazino-3-oxopropionate (1.24 g, 8.49 mmol) and catalytic AcOH (0.1 mL, 1.70 mmol) were added to a solution of the compound from example 31a) (2.38 g. 11.43 mmol) in EtOH (20 mL). The reaction was heated to reflux and stirred overnight. A few spatula tips of $MgSO_4$ were added and the reaction continued to stir for 3 h. The reaction was then cooled to room temperature and filtered. The filtrate was concentrated and azeotroped with Toluene several times. The product was purified by column chromatography ($SiO_2$, 15-45% EtOAc/Hexanes) to give the title compound (2.24 g, 78%). 1H NMR (400 MHz, DMSO-$d_6$) δ ppm 10.48-11.47 (m, 1H) 7.19-7.61 (m, 2H) 6.94-7.12 (m, 2H) 4.02-4.48 (m, 4H) 3.42-3.86 (m, 5H) 1.09-1.36 (m, 6H).

31c) Ethyl 5-hydroxy-6-[4-(methyloxy)phenyl]-3-oxo-2,3-dihydro-4-pyridazinecarboxylate. KHMDS (1.82 g, 9.14 mmol) was added in several portions to a solution of the compound from example 31b) (2.05 g, 6.10 mmol) in 1,4-dioxane (15 mL) at room temperature. The reaction was heated to reflux and stirred for 3 h. The reaction was cooled to room temperature and 1N HCl was added to precipitate the product. $CH_2Cl_2$ and $H_2O$ were added and the layers separated. The aqueous phase was backextracted with $CH_2Cl_2$ several times. The combined organic layers were washed with Brine, dried ($MgSO_4$), filtered and concentrated. $Et_2O$ was added and the product filtered to give the title compound as a pale yellow solid (1.14 g, 64%). 1H NMR (400 MHz, DMSO-$d_6$) δ ppm 12.99 (s, 1H) 12.62 (br. s., 1H) 7.55-7.65 (m, 2H) 6.93-7.06 (m, 2H) 4.32 (q, J=7.07 Hz, 2H) 3.80 (s, 3H) 1.29 (t, J=7.20 Hz, 3H).

31d) Ethyl 2-[(2-chlorophenyl)methyl]-5-hydroxy-6-[4-(methyloxy)phenyl]-3-oxo-2,3-dihydro-4-pyridazinecarboxylate. Sodium hydride (50 mg, 1.25 mmol) was added to a solution of the compound from example 31c) (145 mg, 0.50 mmol) in N,N-Dimethylformamide (DMF) (2 mL) at 0° C. The reaction was brought to room temperature and stirred for 45 minutes. The temperature was then reduced to 0° C. and 2-chlorobenzyl bromide (0.06 mL, 0.50 mmol) was added. The reaction was brought to room temperature and stirred for 2.5 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 1-5% MeOH/$CH_2Cl_2$ then 40-80% EtOAc/Hexanes) give the title compound (106 mg, 51%). 1H NMR (400 MHz, MeOD) δ ppm 7.69-7.77 (m, 2H) 7.42-7.47 (m, 1H) 7.25-7.34 (m, 2H) 7.18-7.24 (m, 1H) 6.92-7.00 (m, 2H) 5.49 (s, 2H) 4.49 (q, J=7.07 Hz, 2H) 3.84 (s, 3 H) 1.43 (t, J=7.07 Hz, 3H).

31e) N-({2-[(2-Chlorophenyl)methyl]-5-hydroxy-6-[4-(methyloxy)phenyl]-3-oxo-2,3-dihydro-4-pyridazinyl}carbonyl)glycine. Glycine, sodium salt (40 mg, 0.41 mmol) was added to a solution of the compound from example 31d) (85 mg, 0.21 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by precipitation from $CH_2Cl_2$/Hexanes to give the title compound (59 mg, 65%). 1H NMR (400 MHz, DMSO-$d_6$) δ ppm 13.03 (s, 1H) 10.24 (t, J=4.93 Hz, 1H) 7.67-7.77 (m, 2H) 7.51 (dd, J=7.71, 1.64 Hz, 1H) 7.28-7.39 (m, 2H) 7.23 (dd, J=7.45, 1.89 Hz, 1H) 7.03 (ddd, J=9.41, 2.78, 2.46 Hz, 2H) 5.44 (s, 2H) 4.13 (d, J=5.56 Hz, 2H) 3.80 (s, 3H).

Example 32

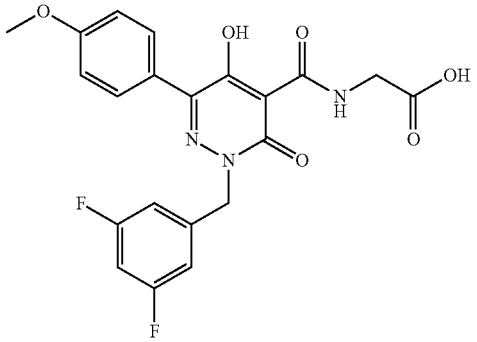

N-({2-[(3,5-Difluorophenyl)methyl]-5-hydroxy-6-[4-(methyloxy)phenyl]-3-oxo-2,3-dihydro-4-pyridazinyl}carbonyl)glycine 32a) Ethyl 2-[(3,5-difluorophenyl)methyl]-5-hydroxy-6-[4-(methyloxy)phenyl]-3-oxo-2,3-dihydro-4-pyridazinecarboxylate. Sodium hydride (91 mg, 2.28 mmol) was added to a solution of the compound from example 31c) (265 mg, 0.91 mmol) in N,N-Dimethylformamide (DMF) (3.5 mL) at 0° C. The reaction was brought to room temperature and stirred for 45 minutes. The temperature was then reduced to 0° C. and 3,5-difluorobenzyl bromide (0.13 mL, 1.00 mmol) was added. The reaction was brought to room temperature and stirred for 3.5 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 40-65% EtOAc/Hexanes) give the title compound (247 mg, 65%). 1H NMR (400 MHz, DMSO-$d_6$) δ ppm 12.65 (br. s., 1H) 7.64 (ddd, J=9.35, 2.78, 2.53 Hz, 2H) 7.18 (tt, J=9.44, 2.31 Hz, 1H) 6.98-7.08 (m, 4H) 5.26 (s, 2H) 4.31 (q, J=7.24 Hz, 2H) 3.80 (s, 3 H) 1.29 (t, J=7.07 Hz, 3H).

32b) N-({2-[(3,5-Difluorophenyl)methyl]-5-hydroxy-6-[4-(methyloxy)phenyl]-3-oxo-2,3-dihydro-4-pyridazinyl}carbonyl)glycine. Glycine, sodium salt (112 mg, 1.16 mmol) was added to a solution of the compound from example 32a) (241 mg, 0.58 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (220 mg, 85%). 1H NMR (400 MHz, DMSO-$d_6$) δ ppm 13.08 (br. s., 1H) 10.23 (t, J=5.43 Hz, 1H) 7.72-7.78 (m, 2H) 7.18 (tt, J=9.38, 2.37 Hz, 1H) 7.01-7.12 (m, 4H) 5.37 (s, 2H) 4.13 (d, J=5.56 Hz, 2H) 3.81 (s, 3H).

Example 33

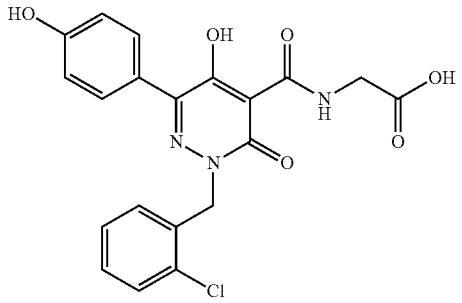

N-{[2-[(2-Chlorophenyl)methyl]-5-hydroxy-6-(4-hydroxyphenyl)-3-oxo-2,3-dihydro-4-pyridazinyl]carbonyl}glycine A solution of the compound from example 31e) in glacial acetic acid (1.6 mL) was heated to reflux followed by the addition of 48% aqueous HBr (0.4 mL). After stirring for 6.5 h at reflux, the reaction was cooled to room temperature and $H_2O$ was added. The precipitate was filtered to give the title compound as a tan solid (35 mg, 54%). 1H NMR (400 MHz, DMSO-$d_6$) δ ppm 16.41 (s, 1H) 13.00 (s, 1H) 10.24 (t, J=5.56 Hz, 1H) 9.85 (s, 1H) 7.62 (d, J=8.59 Hz, 2H) 7.51 (dd, J=7.71, 1.64 Hz, 1H) 7.26-7.39 (m, 2H) 7.20 (dd, J=7.45, 1.89 Hz, 1H) 6.80-6.87 (m, 2H) 5.43 (s, 2H) 4.13 (d, J=5.56 Hz, 2H).

Example 34

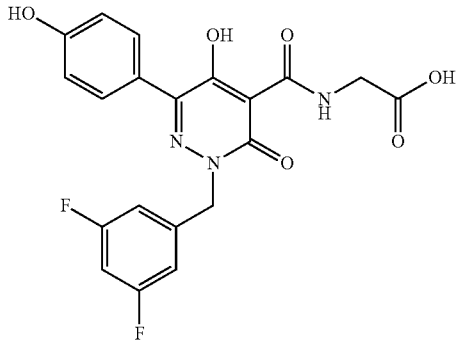

N-{[2-[(3,5-Difluorophenyl)methyl]-5-hydroxy-6-(4-hydroxyphenyl)-3-oxo-2,3-dihydro-4-pyridazinyl]carbonyl}glycine A solution of the compound from example 32b) in glacial acetic acid (2.6 mL) was heated to reflux followed by the addition of 48% aqueous HBr (0.6 mL). After stirring overnight at reflux, the reaction was cooled to room temperature and $H_2O$ was added. The precipitate was filtered and washed with $H_2O$ and Hexanes to give the title compound (70 mg, 78%). 1H NMR (400 MHz, DMSO-$d_6$) δ ppm 16.37 (s, 1H) 13.00 (s, 1H) 10.23 (t, J=5.56 Hz, 1 H) 9.86 (s, 1H) 7.65 (d, J=8.59 Hz, 2H) 7.18 (tt, J=9.44, 2.31 Hz, 1H) 7.07 (ddd, J=14.84, 6.63, 2.27 Hz, 2H) 6.85 (ddd, J=9.22, 2.78, 2.40 Hz, 2H) 5.36 (s, 2H) 4.13 (d, J=5.81 Hz, 2H).

Example 35

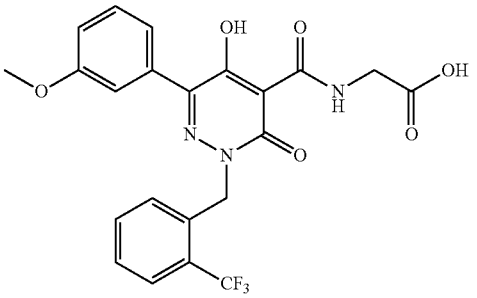

N-[(5-Hydroxy-6-[3-(methyloxy)phenyl]-3-oxo-2-{[2-(trifluoromethyl)phenyl]methyl}-2,3-dihydro-4-pyridazinyl)carbonyl]glycine 35a) Ethyl 3-(2-{2-(ethyloxy)-1-[3-(methyloxy)phenyl]-2-oxoethylidene}hydrazino)-3-oxopropanoate. A solution of diethyl oxylate (2.0 mL, 15.0 mmol) in THF (30 mL) and $Et_2O$ (30 mmol) was cooled to −78° C. 3-methoxyphenyl magnesium bromide (1.0 M solution in THF, 18 mL, 18.0 mmol) was dropwise added and the solution stirred under a nitrogen atmosphere for 2 h at −78° C. The reaction was brought to 0° C. and quenched with 6N HCl. Additional $Et_2O$ and $H_2O$ were added and the layers separated. The aqueous phase was backextracted with $Et_2O$ several times. The combined organic layers were washed with Brine, dried ($MgSO_4$), filtered and concentrated. The resulting residue was dissolved in EtOH (40 mL). Ethyl-3-hydrazino-3-oxopropionate (2.63 g, 18.0 mmol) and catalytic AcOH (0.2 mL, 3.49 mmol) were added along with a few spatula tips of MgSO4. The reaction was heated to reflux and stirred overnight. The reaction was cooled to room temperature and filtered. The filtrate was concentrated and azeotroped with Toluene several times. The product was purified by column chromatography ($SiO_2$, 15-45% EtOAc/Hexanes) to give the title compound (3.56 g, 70% over 2 steps). 1H NMR (400 MHz, DMSO-$d_6$) δ ppm 10.53-11.65 (m, 1H) 7.27-7.49 (m, 1H) 6.67-7.21 (m, 3H) 4.00-4.50 (m, 4H) 3.45-3.85 (m, 5H) 1.08-1.38 (m, 6H).

35b) Ethyl 5-hydroxy-6-[3-(methyloxy)phenyl]-3-oxo-2,3-dihydro-4-pyridazinecarboxylate. KHMDS (2.67 g, 13.38 mmol) was added in several portions to a solution of the compound from example 35a) (3.00 g, 8.92 mmol) in 1,4-dioxane (20 mL) at room temperature. The reaction was heated to reflux and stirred for 3.5 h. The reaction was cooled to room temperature and 1N HCl was added to precipitate the product. The product was filtered and washed with $H_2O$ and Hexanes to give the title compound (1.28 g, 49%). LCMS ($ES^+$) m/z 290.9 ($MH^+$).

35c) Ethyl 5-hydroxy-6-[3-(methyloxy)phenyl]-3-oxo-2-{[2-(trifluoromethyl)phenyl]methyl}-2,3-dihydro-4-pyridazinecarboxylate. Sodium hydride (103 mg, 2.58 mmol) was added to a solution of the compound from example 35b) (300 mg, 1.03 mmol) in N,N-Dimethylformamide (DMF) (2.5 mL) at 0° C. The reaction was brought to room temperature and stirred for 45 minutes. The temperature was then reduced to 0° C. and 2-(trifluoromethyl)-benzyl bromide (247 mg, 1.03 mmol) was added. The reaction was brought to room temperature and stirred for 2.5 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 35-60% EtOAc/Hexanes) give the title compound as a white solid (329 mg, 71%).1H NMR (400 MHz, DMSO-$d_6$) δ ppm 12.71 (br. s., 1H) 7.79 (d, J=7.83 Hz, 1H) 7.65 (t, J=7.45 Hz, 1H) 7.52 (t, J=7.58 Hz, 1H) 7.36 (t, J=7.96 Hz, 1H) 7.15-7.27 (m, 3H) 7.02 (ddd, J=8.27, 2.59, 1.01 Hz, 1H) 5.45 (s, 2H) 4.32 (q, J=7.07 Hz, 2H) 3.76 (s, 3H) 1.29 (t, J=7.20 Hz, 3H).

35d) N-[(5-Hydroxy-6-[3-(methyloxy)phenyl]-3-oxo-2-{[2-(trifluoromethyl)phenyl]methyl}-2,3-dihydro-4-pyridazinyl)carbonyl]glycine. Glycine, sodium salt (137 mg, 1.41 mmol) was added to a solution of the compound from example 35c) (316 mg, 0.71 mmol) in 2-methoxyethanol (2.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (266 mg, 79%). 1H NMR (400 MHz, DMSO-$d_6$) δ ppm 13.00 (s, 1H) 10.18 (t J=5.31 Hz, 1H) 7.80 (d, J=7.83 Hz, 1H) 7.64 (t, J=7.45 Hz, 1H) 7.53 (t, J=7.71 Hz, 1H) 7.23-7.45 (m, 4H) 6.99-7.11 (m, 1H) 5.55 (s, 2H) 4.13 (d, J=5.81 Hz, 2H) 3.77 (s, 3H).

Example 36

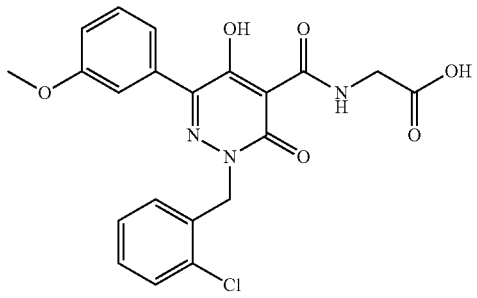

N-({2-[(2-Chlorophenyl)methyl]-5-hydroxy-6-[3-(methyloxy)phenyl]-3-oxo-2,3-dihydro-4-pyridazinyl}carbonyl)glycine 36a) Ethyl 2-[(2-chlorophenyl)methyl]-5-hydroxy-6-[3-(methyloxy)phenyl]-3-oxo-2,3-dihydro-4-pyridazinecarboxylate. Sodium hydride (103 mg, 2.58 mmol) was added to a solution of the compound from example 35b) (300 mg, 1.03 mmol) in N,N-Dimethylformamide (DMF) (2.5 mL) at 0° C. The reaction was brought to room temperature and stirred for 45 minutes. The temperature was then reduced to 0° C. and 2-chlorobenzyl bromide (0.13 mL, 1.03 mmol) was added. The reaction was brought to room temperature and stirred for 2.5 hours followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 40-65% EtOAc/Hexanes) give the title compound as a white solid (294 mg, 69%). 1H NMR (400 MHz, DMSO-$d_6$) δ ppm 12.67 (s, 1H) 7.50 (td, J=3.60, 2.15 Hz, 1H) 7.29-7.40 (m, 3H) 7.15-7.27 (m, 3H) 7.02 (ddd, J=8.27, 2.59, 1.01 Hz, 1H) 5.35 (s, 2 H) 4.31 (q, J=7.07 Hz, 2H) 3.76 (s, 3H) 1.29 (t, J=7.07 Hz, 3H).

36b) N-({2-[(2-Chlorophenyl)methyl]-5-hydroxy-6-[3-(methyloxy)phenyl]-3-oxo-2,3-dihydro-4-pyridazinyl}carbonyl)glycine. Glycine, sodium salt (129 mg, 1.33 mmol) was added to a solution of the compound from example 36a) (275 mg, 0.66 mmol) in 2-methoxyethanol (2.5 mL) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes to give the title compound (232 mg, 79%). 1H NMR (400 MHz, DMSO-$d_6$) δ ppm 13.02 (s, 1H) 10.21 (t, J=4.29 Hz, 1H) 7.48-7.57 (m, 1H) 7.24-7.42 (m, 6H) 7.02-7.08 (m, 1H) 5.46 (s, 2H) 4.14 (d, J=5.56 Hz, 2H) 3.77 (s, 3H).

Example 37

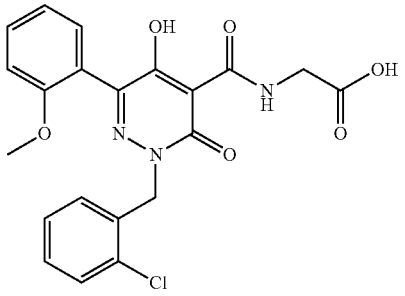

N-({2-[(2-Chlorophenyl)methyl]-5-hydroxy-6-[2-(methyloxy)phenyl]-3-oxo-2,3-dihydro-4-pyridazinyl}carbonyl)glycine 37a) Ethyl 3-(2-{2-(ethyloxy)-1-[2-(methyloxy)phenyl]-2-oxoethylidene}hydrazino)-3-oxopropanoate. A solution of diethyl oxylate (2.7 mL, 20.0 mmol) in THF (40 mL) and $Et_2O$ (40 mmol) was cooled to −78° C. 2-methoxyphenyl magnesium bromide (1.0 M solution in $Et_2O$, 24 mL, 24.0 mmol) was dropwise added and the solution stirred under a nitrogen atmosphere for 2 h at −78° C. The reaction was brought to 0° C. and quenched with 6N HCl. Additional $Et_2O$ and $H_2O$ were added and the layers separated. The aqueous phase was backextracted with $Et_2O$ several times. The combined organic layers were washed with Brine, dried ($MgSO_4$), filtered and concentrated. The resulting residue was dissolved in EtOH (40 mL). Ethyl-3-hydrazino-3-oxopropionate (3.22 g, 22.0 mmol) and catalytic AcOH (0.2 mL, 3.49 mmol) were added along with a few spatula tips of $MgSO_4$. The reaction was heated to reflux and stirred overnight. The reaction was cooled to room temperature and filtered. The filtrate was concentrated and azeotroped with Toluene several times. The product was purified by column chromatography ($SiO_2$, 20-45% EtOAc/Hexanes) to give the title compound (3.98 g, 59% over 2 steps). 1H NMR (400 MHz, DMSO-$d_6$) δ ppm 10.41-11.75 (m, 1H) 7.31-7.56 (m, 2H) 6.88-7.26 (m, 2H) 3.98-4.37 (m, 4H) 3.23-3.82 (m, 5H) 0.95-1.30 (m, 6H).

37b) Ethyl 5-hydroxy-6-[2-(methyloxy)phenyl]-3-oxo-2,3-dihydro-4-pyridazinecarboxylate. KHMDS (1.78 g, 8.92 mmol) was added in several portions to a solution of the compound from example 37a) (2.00 g, 5.95 mmol) in 1,4-dioxane (13 mL) at room temperature. The reaction was heated to reflux and stirred for 1 h. Additional KHMDS (595 mg, 2.98 mmol) was added and the reaction stirred 3 h. The reaction was cooled to room temperature and 1N HCl was added to precipitate the product. The product was purified by column chromatography ($SiO_2$, 0-4% MeOH/$CH_2Cl_2$) then precipitation from $CH_2Cl_2$/Hexanes to give the title compound (384 mg, 22%). 1H NMR (400 MHz, DMSO-$d_6$) δ ppm 12.94 (s, 1H) 11.96 (s, 1H) 7.40-7.49 (m, 1H) 7.24 (dd, J=7.33, 1.77 Hz, 1H) 7.10 (d, J=7.83 Hz, 1H) 7.02 (td, J=7.39, 0.88 Hz, 1H) 4.29 (q, J=7.07 Hz, 2H) 3.75 (s, 3H) 1.28 (t, J=7.07 Hz, 3H).

37c) Ethyl 2-[(2-chlorophenyl)methyl]-5-hydroxy-6-[2-(methyloxy)phenyl]-3-oxo-2,3-dihydro-4-pyridazinecarboxylate. Sodium hydride (70 mg, 1.75 mmol) was added to a solution of the compound from example 37b) (203 mg, 0.70 mmol) in N,N-Dimethylformamide (DMF) (2.5 mL) at 0° C. The reaction was brought to room temperature and stirred for 45 minutes. The temperature was then reduced to 0° C. and 2-chlorobenzyl bromide (0.13 mL, 1.03 mmol) was added. The reaction was brought to room temperature and stirred for 4 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 30-55% EtOAc/Hexanes) give the title compound (79 mg, 27%). LCMS ($ES^+$) m/z 415.1 ($MH^+$).

37d) N-({2-[(2-Chlorophenyl)methyl]-5-hydroxy-6-[2-(methyloxy)phenyl]-3-oxo-2,3-dihydro-4-pyridazinyl}carbonyl)glycine. Glycine, sodium salt (35 mg, 0.36 mmol) was added to a solution of the compound from example 37c) (75 mg, 0.18 mmol) in 2-methoxyethanol (1.5 mL) at room temperature. The reaction was heated to reflux and stirred for 1.5 h. The reaction was cooled back to room temperature and $H_2O$ was added. The solution was filtered and 1N HCl was added to precipitate the product. The product was filtered then redissolved in MeOH. The solution was concentrated and $Et_2O$ added. The product was filtered to give the title compound as an off-white solid (38 mg, 48%). 1H NMR (400 MHz, DMSO-$d_6$) δ ppm 15.76 (s, 1H) 12.98 (s, 1H) 10.12 (t, J=5.68 Hz, 1H) 7.41-7.56 (m, 2H) 7.30-7.40 (m, 2H) 7.29 (dd, J=7.33, 1.77 Hz, 1H) 7.09-7.22 (m, 2H) 7.04 (td, J=7.45, 0.76 Hz, 1H) 5.42 (s, 2H) 4.11 (d, J=5.81 Hz, 2H) 3.76 (s, 3H).

Example 38

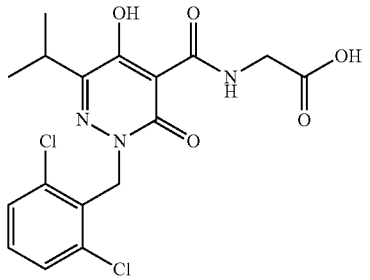

N-{[2-[(2,6-Dichlorophenyl)methyl]-5-hydroxy-6-(1-methylethyl)-3-oxo-2,3-dihydro-4-pyridazinyl]carbonyl}glycine 38a) Ethyl 2-[(2,6-dichlorophenyl)methyl]-5-hydroxy-6-(1-methylethyl)-3-oxo-2,3-dihydro-4-pyridazinecarboxylate. Sodium hydride (66 mg, 1.66 mmol) was added to a solution of the compound from example 14a) (150 mg, 0.66 mmol) in N,N-Dimethylformamide (DMF) (2.5 mL) at 0° C. The reaction was brought to room temperature and stirred for 30 minutes. The temperature was then reduced to 0° C. and 2,6-dichlorobenzyl bromide (159 mg, 0.66 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) give the title compound (157 mg, 62%). 1H NMR (400 MHz, DMSO-$d_6$) δ ppm 7.47-7.55 (m, 2H) 7.36-7.44 (m, 1H) 5.35 (s, 2H) 4.29 (q, J=7.16 Hz, 2H) 3.02 (sept, J=6.74 Hz, 1H) 1.28 (t, J=7.07 Hz, 3H) 0.89 (d, J=6.82 Hz, 6H).

38b) N-{[2-[(2,6-Dichlorophenyl)methyl]-5-hydroxy-6-(1-methylethyl)-3-oxo-2,3-dihydro-4-pyridazinyl]carbonyl}glycine. Glycine, sodium salt (74 mg, 0.76 mmol) was added to a solution of the compound from example 38a) (146 mg, 0.38 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (124 mg, 79%). 1H NMR (400 MHz, DMSO-$d_6$) δ ppm 15.83 (s, 1H) 13.09 (s, 1H) 10.21 (t, J=5.56 Hz, 1H) 7.49-7.57 (m, 2H) 7.36-7.47 (m, 1H) 5.47 (s, 2H) 4.11 (d, J=5.56 Hz, 2H) 3.04 (sept, J=6.78 Hz, 1H) 0.93 (d, J=6.82 Hz, 6H).

Example 39

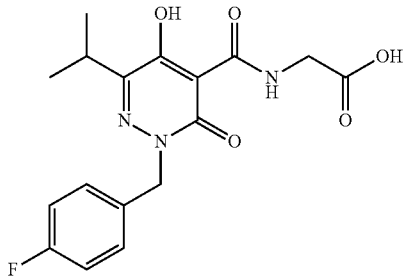

N-{[2-[(4-Fluorophenyl)methyl]-5-hydroxy-6-(1-methylethyl)-3-oxo-2,3-dihydro-4-pyridazinyl]carbonyl}glycine 39a) Ethyl 2-[(4-fluorophenyl)methyl]-5-hydroxy-6-(1-methylethyl)-3-oxo-2,3-dihydro-4-pyridazinecarboxylate. Sodium hydride (66 mg, 1.66 mmol) was added to a solution of the compound from example 14a) (150 mg, 0.66 mmol) in N,N-Dimethylformamide (DMF) (2.5 mL) at 0° C. The reaction was brought to room temperature and stirred for 30 minutes. The temperature was then reduced to 0° C. and 4-fluorobenzyl bromide (0.08 mL, 0.66 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) give the title compound (106 mg, 48%). 1H NMR (400 MHz, DMSO-$d_6$) δ ppm 12.26 (s, 1H) 7.33 (ddd, J=12.00, 5.43, 3.03 Hz, 2H) 7.11-7.22 (m, 2H) 5.12 (s, 2H) 4.26 (q, J=7.24 Hz, 2H) 3.15 (sept, J=6.82 Hz, 1H) 1.25 (t, J=7.07 Hz, 3H) 1.16 (d, J=6.82 Hz, 6H).

39b) N-{[2-[(4-Fluorophenyl)methyl]-5-hydroxy-6-(1-methylethyl)-3-oxo-2,3-dihydro-4-pyridazinyl]carbonyl}glycine. Glycine, sodium salt (57 mg, 0.59 mmol) was added to a solution of the compound from example 39a) (98 mg, 0.29 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (86 mg, 82%). 1H NMR (400 MHz, DMSO-$d_6$) δ ppm 15.87 (s, 1H) 12.98 (s, 1H) 10.18 (t, J=5.18 Hz, 1H) 7.36 (ddd, J=11.87, 5.31, 2.78 Hz, 2H) 7.10-7.24 (m, 2H) 5.23 (s, 2 H) 4.10 (d, J=5.81 Hz, 2H) 3.18 (sept, J=6.82 Hz, 1H) 1.20 (d, J=6.82 Hz, 6 H).

Example 40

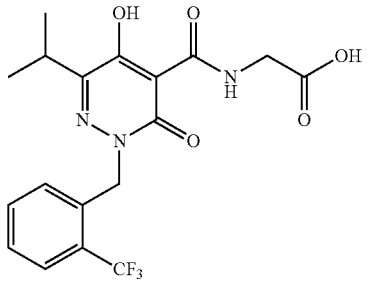

N-[(5-Hydroxy-6-(1-methylethyl)-3-oxo-2-{[2-(trifluoromethyl)phenyl]methyl}-2,3-dihydro-4-pyridazinyl)carbonyl]glycine 40a) Ethyl 5-hydroxy-6-(1-methylethyl)-3-oxo-2-{[2-(trifluoromethyl)phenyl]methyl}-2,3-dihydro-4-pyridazinecarboxylate. Sodium hydride (53 mg, 1.33 mmol) was added to a solution of the compound from example 14a) (120 mg, 0.53 mmol) in N,N-Dimethylformamide (DMF) (2.5 mL) at 0° C. The reaction was brought to room temperature and stirred for 30 minutes. The temperature was then reduced to 0° C. and 2-(trifluoromethyl)-benzyl bromide (127 mg, 0.53 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) give the title compound (144 mg, 71%). 1H NMR (400 MHz, DMSO-$d_6$) δ ppm 12.40 (s, 1H) 7.77 (d, J=7.58 Hz, 1H) 7.64 (t, J=7.58 Hz, 1H) 7.51 (t, J=7.71 Hz, 1H) 7.10 (d, J=7.58 Hz, 1H) 5.34 (s, 2H) 4.28 (q, J=7.07 Hz, 2H) 3.16 (sept, J=6.78 Hz, 1H) 1.26 (t, J=7.07 Hz, 3H) 1.10 (d, J=6.82 Hz, 6H).

40b) N-[(5-Hydroxy-6-(1-methylethyl)-3-oxo-2-{[2-(trifluoromethyl)phenyl]methyl}-2,3-dihydro-4-pyridazinyl) carbonyl]glycine. Glycine, sodium salt (69 mg, 0.71 mmol) was added to a solution of the compound from example 40a) (137 mg, 0.36 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (136 mg, 91%). 1H NMR (400 MHz, DMSO-$d_6$) δ ppm 10.19 (t, J=3.92 Hz, 1H) 7.78 (d, J=7.83 Hz, 1H) 7.62 (t, J=7.33 Hz, 1H) 7.51 (t, J=7.58 Hz, 1H) 7.13 (d, J=7.83 Hz, 1H) 5.42 (s, 2H) 4.04 (d, J=5.56 Hz, 2H) 3.19 (sept, J=7.07 Hz, 1H) 1.13 (d, J=6.82 Hz, 6 H).

Example 41

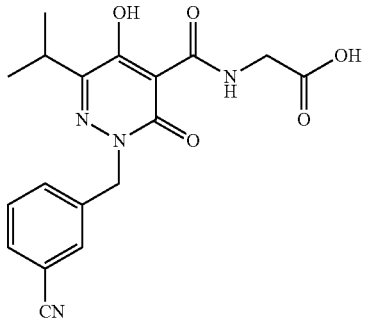

N-{[2-[(3-Cyanophenyl)methyl]-5-hydroxy-6-(1-methylethyl)-3-oxo-2,3-dihydro-4-pyridazinyl] carbonyl}glycine 41a) Ethyl 2-[(3-cyanophenyl)methyl]-5-hydroxy-6-(1-methylethyl)-3-oxo-2,3-dihydro-4-pyridazinecarboxylate. Sodium hydride (53 mg, 1.33 mmol) was added to a solution of the compound from example 14a) (120 mg, 0.53 mmol) in N,N-Dimethylformamide (DMF) (2.5 mL) at 0° C. The reaction was brought to room temperature and stirred for 30 minutes. The temperature was then reduced to 0° C. and α-bromo-m-tolunitrile (104 mg, 0.53 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 30-60% EtOAc/Hexanes) to give the title compound (95 mg, 52%). 1H NMR (400 MHz, DMSO-$d_6$) δ ppm 12.35 (s, 1H) 7.78 (dt, J=6.88, 1.74 Hz, 1H) 7.72 (s, 1H) 7.52-7.63 (m, 2H) 5.20 (s, 2H) 4.27 (q, J=7.16 Hz, 2H) 3.16 (sept, J=6.82 Hz, 1H) 1.26 (t, J=7.07 Hz, 3H) 1.16 (d, J=6.82 Hz, 6H).

41b) N-{[2-[(3-Cyanophenyl)methyl]-5-hydroxy-6-(1-methylethyl)-3-oxo-2,3-dihydro-4-pyridazinyl] carbonyl}glycine. Glycine, sodium salt (54 mg, 0.56 mmol) was added to a solution of the compound from example 41a) (95 mg, 0.28 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (49 mg, 47%). 1H NMR (400 MHz, DMSO-$d_6$) δ ppm 15.92 (s, 1H) 12.97 (s, 1H) 10.13 (t, J=5.31 Hz, 1H) 7.73-7.82 (m, 2H) 7.52-7.66 (m, 2H) 5.31 (s, 2H) 4.09 (d, J=5.56 Hz, 2H) 3.18 (sept, J=6.95 Hz, 1H) 1.19 (d, J=6.82 Hz, 6H).

Example 42

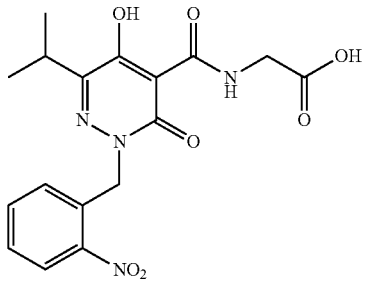

N-({5-Hydroxy-6-(1-methylethyl)-2-[(2-nitrophenyl) methyl]-3-oxo-2,3-dihydro-4-pyridazinyl}carbonyl) glycine 42a) Ethyl 5-hydroxy-6-(1-methylethyl)-2-[(2-nitrophenyl)methyl]-3-oxo-2,3-dihydro-4-pyridazinecarboxylate. Sodium hydride (88 mg, 2.21 mmol) was added to a solution of the compound from example 14a) (200 mg, 0.88 mmol) in N,N-Dimethylformamide (DMF) (3.5 mL) at 0° C. The reaction was brought to room temperature and stirred for 30 minutes. The temperature was then reduced to 0° C. and 2-nitrobenzyl bromide (191 mg, 0.88 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 30-60% EtOAc/Hexanes) to give the title compound (206 mg, 65%). 1H NMR (400 MHz, DMSO-$d_6$) δ ppm 12.37 (s, 1H) 8.07 (dd, J=8.21, 1.14 Hz, 1H) 7.72 (td, J=7.58, 1.26 Hz, 1H) 7.54-7.62 (m, 1H) 7.29 (dd, J=7.71, 1.14 Hz, 1H) 5.46 (s, 2H) 4.27 (q, J=7.07 Hz, 2H) 3.13 (sept, J=6.78 Hz, 1H) 1.25 (t, J=7.20 Hz, 3H) 1.09 (d, J=6.82 Hz, 6H).

42b) N-({5-Hydroxy-6-(1-methylethyl)-2-[(2-nitrophenyl)methyl]-3-oxo-2,3-dihydro-4-pyridazinyl}carbonyl)glycine. Glycine, sodium salt (107 mg, 1.10 mmol) was added to a solution of the compound from example 42a) (200 mg, 0.55 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (157 mg, 73%). 1H NMR (400 MHz, DMSO-$d_6$) δ ppm 15.94 (s, 1H) 12.98 (s, 1H) 10.08 (t, J=5.43 Hz, 1H) 8.10 (dd, J=8.08, 1.26 Hz, 1H) 7.72 (td, J=7.58, 1.26 Hz, 1H) 7.55-7.64 (m, 1H) 7.31

(dd, J=7.58, 1.01 Hz, 1H) 5.57 (s, 2H) 4.10 (d, J=5.56 Hz, 2H) 3.16 (sept, J=6.78 Hz, 1H) 1.13 (d, J=6.82 Hz, 6H).

Example 43

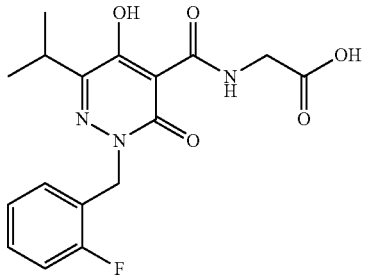

N-{[2-[(2-Fluorophenyl)methyl]-5-hydroxy-6-(1-methylethyl)-3-oxo-2,3-dihydro-4-pyridazinyl] carbonyl}glycine 43a) Ethyl 2-[(2-fluorophenyl)methyl]-5-hydroxy-6-(1-methylethyl)-3-oxo-2,3-dihydro-4-pyridazinecarboxylate. Sodium hydride (53 mg, 1.33 mmol) was added to a solution of the compound from example 14a) (120 mg, 0.53 mmol) in N,N-Dimethylformamide (DMF) (2.5 mL) at 0° C. The reaction was brought to room temperature and stirred for 30 minutes. The temperature was then reduced to 0° C. and 2-fluorobenzyl bromide (0.06 mL, 0.53 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) give the title compound (110 mg, 62%). 1H NMR (400 MHz, DMSO-$d_6$) δ ppm 12.30 (s, 1H) 7.30-7.39 (m, 1H) 7.10-7.26 (m, 3H) 5.20 (s, 2H) 4.27 (q, J=7.07 Hz, 2H) 3.15 (sept, J=6.82 Hz, 1H) 1.26 (t, J=7.07 Hz, 3H) 1.13 (d, J=6.82 Hz, 6H).

43b) N-{[2-[(2-Fluorophenyl)methyl]-5-hydroxy-6-(1-methylethyl)-3-oxo-2,3-dihydro-4-pyridazinyl] carbonyl}glycine. Glycine, sodium salt (64 mg, 0.66 mmol) was added to a solution of the compound from example 43a) (110 mg, 0.33 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (108 mg, 90%). 1H NMR (400 MHz, DMSO-$d_6$) δ ppm 15.90 (s, 1H) 12.96 (s, 1H) 10.15 (t, J=5.56 Hz, 1H) 7.32-7.41 (m, 1H) 7.13-7.30 (m, 3H) 5.31 (s, 2H) 4.10 (d, J=5.56 Hz, 2H) 3.17 (sept, J=6.86 Hz, 1H) 1.17 (d, J=6.82 Hz, 6H).

Example 44

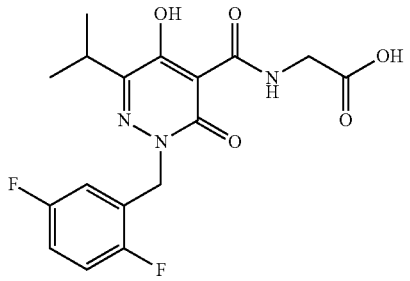

N-{[2-[(2,5-Difluorophenyl)methyl]-5-hydroxy-6-(1-methylethyl)-3-oxo-2,3-dihydro-4-pyridazinyl] carbonyl}glycine 44a) Ethyl 2-[(2,5-difluorophenyl)methyl]-5-hydroxy-6-(1-methylethyl)-3-oxo-2,3-dihydro-4-pyridazinecarboxylate. Sodium hydride (53 mg, 1.33 mmol) was added to a solution of the compound from example 14a) (120 mg, 0.53 mmol) in N,N-Dimethylformamide (DMF) (2.5 mL) at 0° C. The reaction was brought to room temperature and stirred for 30 minutes. The temperature was then reduced to 0° C. and 2,5-difluorobenzyl bromide (0.07 mL, 0.53 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 15-30% EtOAc/Hexanes) give the title compound (133 mg, 71%). 1H NMR (400 MHz, DMSO-$d_6$) δ ppm 12.35 (s, 1H) 7.28 (td, J=9.22, 4.55 Hz, 1H) 7.15-7.25 (m, 1 H) 7.05 (ddd, J=8.84, 5.68, 3.16 Hz, 1H) 5.18 (s, 2H) 4.27 (q, J=7.07 Hz, 2H) 3.15 (sept, J=6.82 Hz, 1H) 1.26 (t, J=7.07 Hz, 3H) 1.13 (d, J=6.82 Hz, 6H).

44b) N-{[2-[(2,5-Difluorophenyl)methyl]-5-hydroxy-6-(1-methylethyl)-3-oxo-2,3-dihydro-4-pyridazinyl] carbonyl}glycine. Glycine, sodium salt (69 mg, 0.71 mmol) was added to a solution of the compound from example 44a) (125 mg, 0.35 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (112 mg, 84%). 1H NMR (400 MHz, DMSO-$d_6$) δ ppm 15.92 (s, 1H) 12.97 (s, 1H) 10.12 (t J=5.56 Hz, 1H) 7.29 (td, J=9.22, 4.55 Hz, 1H) 7.17-7.25 (m, 1H) 7.12 (ddd, J=8.91, 5.62, 3.16

Hz, 1H) 5.29 (s, 2H) 4.10 (d, J=5.81 Hz, 2H) 3.17 (sept, J=6.86 Hz, 1H) 1.16 (d, J=6.82 Hz, 6H).

Example 45

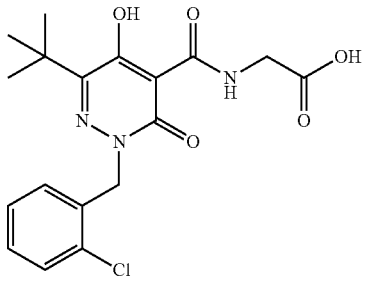

N-{[2-[(2-Chlorophenyl)methyl]-6-(1,1-dimethylethyl)-5-hydroxy-3-oxo-2,3-dihydro-4-pyridazinyl]carbonyl}glycine 45a) Ethyl 3,3-dimethyl-2-oxobutanoate. DBU (2.1 mL, 14.0 mmol) was slowly added to a suspension of trimethyl pyruvic acid (60% aqueous solution, 2.17 g, 10.0 mmol) in MTBE (15 mL). Bromoethane (1.8 mL, 24.0 mmol) was then added. The reaction was heated in the microwave at 100° C. for 30 minutes. The reaction was cooled and 10% $NaHCO_3$ (aq) solution was added. The layers were separated and the organic layer was washed again with 10% $NaHCO_3$ (aq). The aqueous phase was backextraced with $Et_2O$ several times. The combined organic layers were washed with Brine, dried ($MgSO_4$), filtered and concentrated to give the title compound as a pale yellow oil (1.44 g, 91%). 1H NMR (400 MHz, CHLOROFORM-d) δ ppm 4.34 (q, J=7.07 Hz, 4 H) 1.38 (t, J=7.20 Hz, 3H) 1.28 (s, 9H).

45b) Ethyl-2-{[3-(ethyloxy)-3-oxopropanoyl]hydrazono}-3,3-dimethylbutanoate. Ethyl-3-hydrazino-3-oxopropionate (2.38 g, 16.31 mmol) and catalytic AcOH (0.15 mL, 2.62 mmol) were added to a solution of the compound from example 45a) (2.15 g. 13.59 mmol) in EtOH (20 mL). The reaction was heated in the microwave at 150° C. for 30 minutes. The reaction was then cooled to room temperature and solvent removed under reduced pressure. The product was purified by column chromatography ($SiO_2$, 15-30% EtOAc/Hexanes) to give the title compound (1.66 g, 43%). 1H NMR (400 MHz, DMSO-$d_6$) δ ppm 10.76-11.13 (m, 1H) 4.01-4.38 (m, 4H) 3.39-3.61 (m, 2H) 1.07-1.33 (m, 15H).

45c) Ethyl 6-(1,1-dimethylethyl)-5-hydroxy-3-oxo-2,3-dihydro-4-pyridazinecarboxylate. KOtBu (1M solution in t-BuOH, 9.4 mL, 9.38 mmol) was added to the compound from example 45b) (1.79 g, 6.25 mmol). The reaction was heated in the microwave at 150° C. for 20 minutes. The reaction was cooled and $H_2O$ was added followed by 1N HCl to precipitate the product. The solid was filtered to give the title compound (1.04 g, 69%). 1H NMR (400 MHz, DMSO-$d_6$) δ ppm 12.73 (s, 1H) 12.64 (s, 1H) 4.30 (q, J=7.07 Hz, 2H) 1.30 (s, 9H) 1.28 (t, J=7.20 Hz, 3H).

45d) Ethyl 2-[(2-chlorophenyl)methyl]-6-(1,1-dimethylethyl)-5-hydroxy-3-oxo-2,3-dihydro-4-pyridazinecarboxylate. Sodium hydride (42 mg, 1.00 mmol) was added to a solution of the compound from example 45c) (10 mg, 0.42 mmol) in N,N-Dimethylformamide (DMF) (2 mL) at 0° C. The reaction was brought to room temperature and stirred for 30 minutes. The temperature was then reduced to 0° C. and 2-chlorobenzyl bromide (0.05 mL, 0.42 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) give the title compound (106 mg, 69%). 1H NMR (400 MHz, DMSO-$d_6$) δ ppm 12.67 (s, 1H) 7.48 (ddd, J=7.14, 5.75, 3.54 Hz, 1H) 7.28-7.37 (m, 2H) 7.11-7.19 (m, 1H) 5.23 (s, 2H) 4.29 (q, J=7.24 Hz, 2H) 1.23-1.30 (m, 12H).

45e) N-{[2-[(2-Chlorophenyl)methyl]-6-(1,1-dimethylethyl)-5-hydroxy-3-oxo-2,3-dihydro-4-pyridazinyl]carbonyl}glycine. Glycine, sodium salt (49 mg, 0.51 mmol) was added to a solution of the compound from example 45d) (93 mg, 0.25 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (79 mg, 81%). 1H NMR (400 MHz, DMSO-$d_6$) δ ppm 16.43 (s, 1H) 12.99 (s, 1H) 10.26 (t, J=5.56 Hz, 1H) 7.44-7.53 (m, 1H) 7.28-7.39 (m, 2H) 7.18-7.24 (m, 1H) 5.34 (s, 2H) 4.11 (d, J=5.56 Hz, 2H) 1.28 (s, 9H).

Example 46

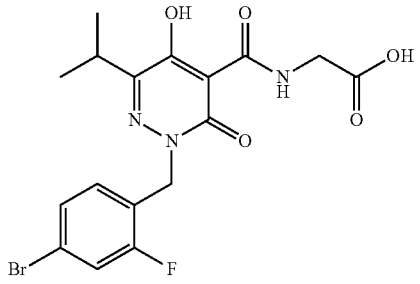

N-{[2-[(4-Bromo-2-fluorophenyl)methyl]-5-hydroxy-6-(1-methylethyl)-3-oxo-2,3-dihydro-4-pyridazinyl]carbonyl}glycine 46a) Ethyl 2-[(4-bromo-2-fluorophenyl)methyl]-5-hydroxy-6-(1-methylethyl)-3-oxo-2,3-dihydro-4-pyridazinecarboxylate. To a solution of ethyl 5-hydroxy-6-(1-methylethyl)-3-oxo-2,3-dihydro-4-pyridazinecarboxylate (9.5 g, 42.0 mmol) in N,N-Dimethylformamide (DMF) (250 ml) at 0° C. was added sodium hydride (60% in oil, 2.52 g, 63.0 mmol) in portions. The reaction mixture was stirred at room temperature for 45 minutes and then cooled back to 0° C. and 4-bromo-2-fluorobenzyl bromide (12.38 g, 46.2 mmol) was added portionwise. The mixture was stirred at ambient temperature for 2.5 hours then quenched with 1N HCl (10 ml) and diluted with water (30 ml). The aqueous solution was extracted with ethyl acetate (2×100 ml), the organic layers combined and washed with water (100 ml) and brine (100 ml), dried over Magnesium sulfate, filtered and solvents removed with rotary evaporation. The crude oil was purified by flash column chromatography (10-100% ethyl acetate in hexanes) to provide the crude product (8 g, ~75% pure, 35% yield) as a pale yellow solid. The material was purified by reverse phase HPLC (C18, 75-90% acetonitrile/0.3 M aqueous ammonium formate) to give the title compound as a white powder. 1H NMR (400 MHz, DMSO-$d_6$) δ ppm 1.13 (d, J=6.82 Hz, 6H) 1.26 (t, J=7.20 Hz, 3H) 3.09-3.17 (m, 1H) 4.26 (q, J=7.07 Hz, 2H) 5.16 (s, 2H) 7.21 (t, J=8.08 Hz, 1H) 7.40 (dd, J=8.34, 1.77 Hz, 1H) 7.57 (dd, J=9.73,1.89 Hz, 1H) 12.31 (s, 1H). MS (ES+) m/e 413 [M+H]+.

46b) N-{[2-[(4-Bromo-2-fluorophenyl)methyl]-5-hydroxy-6-(1-methylethyl)-3-oxo-2,3-dihydro-4-pyridazinyl]carbonyl}glycine. To a 500 mL round bottom was added ethyl 2-[(4-bromo-2-fluorophenyl)methyl]-5-hydroxy-6-(1 -methylethyl)-3-oxo-2,3-dihydro-4-pyridazinecarboxylate (9 g, 21.78 mmol) and glycine sodium salt (5.28 g, 54.4 mmol) in 2-methoxyethanol (150 ml) and the mixture was refluxed at 135° C. for 2 hours. The reaction mixture was diluted with water (50 ml) and acidified with 1N HCl to give a off-white precipitate that was collected by filtration and washed with water, hexanes and ether to give N-{[2-[(4-bromo-2-fluorophenyl)methyl]-5-hydroxy-6-(1-methylethyl)-3-oxo-2,3-dihydro-4-pyridazinyl]carbonyl}glycine (7.20 g, 16.20 mmol, 74.4% yield). The 98% pure material was recrystallized in ethanol to yield 7.0 g of white crystalline powder. 1H NMR (400 MHz, DMSO-$d_6$) d ppm 15.91 (s, 1H), 12.97 (s, 1H), 10.11 (t, J=5.56 Hz, 1H), 7.58 (dd, J=9.60, 2.02 Hz, 1H), 7.40 (dd, J=8.21, 1.64 Hz, 1H), 7.25 (t, J=8.21 Hz, 1 H), 5.26 (s, 2H), 4.10 (d, J=5.56 Hz, 2H), 3.16 (sept, J=6.85, 6.69 Hz, 1H), 1.16 (d, J=6.82 Hz, 6 H). MS (ES+) m/e 444 [M+H]+.

Example 47

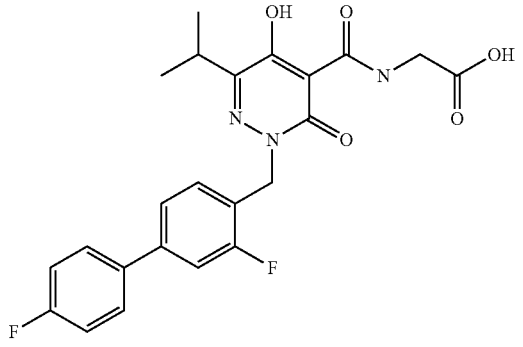

N-{[2-[(3,4'-Difluoro-4-biphenylyl)methyl]-5-hydroxy-6-(1 -methylethyl)-3-oxo-2,3-dihydro-4-pyridazinyl]carbonyl}glycine To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 40 mg, 0.09 mmol), 4-fluorobenzeneboronic acid (15.2 mg, 0.11 mmol), potassium carbonate (38 mg, 0.272 mmol), tetrakis(triphenylphosphine)palladium (0) (3 mg, 2.7 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 25-95% acetonitrile/water (0.1% TFA)) to afford the title compound (23.5 mg, 0.051 mmol, 57% yield) as a white powder. 1H NMR (400 MHz, DMSO-$d_6$) d ppm 15.91 (s, 1H), 12.96 (s, 1H), 10.15 (t, J=5.31 Hz, 1H), 7.69-7.80 (m, 2H), 7.55 (dd, J=11.62, 1.77 Hz, 1H), 7.48 (dd, J=8.08, 1.77 Hz, 1H), 7.23-7.38 (m, 3H), 5.34 (s, 2H), 4.10 (d, J=5.56 Hz, 2H), 3.19 (m, 1H), 1.19 (d, J=6.82 Hz, 6H). MS (ES+) m/e 458 [M+H]+.

Example 48

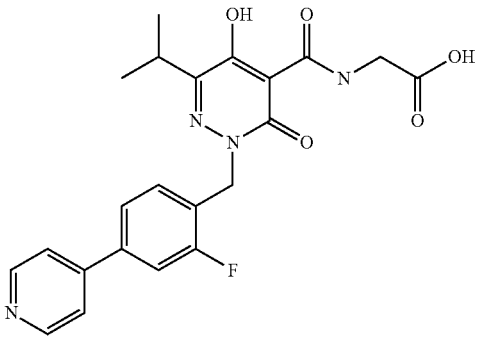

N-{[2-{[2-Fluoro-4-(4-pyridinyl)phenyl]methyl}-5-hydroxy-6-(1-methylethyl)-3-oxo-2,3-dihydro-4-pyridazinyl]carbonyl}glycine To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 40 mg, 0.09 mmol), (4-nitrophenyl)boronic acid (18.1 mg, 0.11 mmol), potassium carbonate (38 mg, 0.272 mmol), tetrakis(triphenylphosphine)palladium (0) (3 mg, 2.7 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 15-95% acetonitrile/water (0.1% TFA)) to afford the title compound (10 mg, 0.023 mmol, 25% yield) as a white powder. 1H NMR (400 MHz, DMSO-$d_6$) d ppm 15.93 (s, 1H), 12.99 (s, 1H), 10.13 (t, J=5.43 Hz, 1H), 8.73 (d, J=5.81 Hz, 2H), 7.91 (d, J=5.56 Hz, 2H), 7.81 (dd, J=11.37, 1.52 Hz, 1 H), 7.70 (dd, J=8.08, 1.52

Hz, 1H), 7.43 (t, J=8.08 Hz, 1H), 5.38 (s, 2H), 4.10 (d, J=5.56 Hz, 2 H), 3.19 (m, 1H), 1.19 (d, J=6.82 Hz, 6H). MS (ES+) m/e 441 [M+H]+.

Example 49

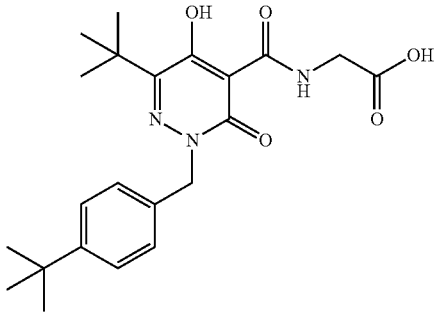

N-[(6-(1,1-Dimethylethyl)-2-{[4-(1,1-dimethylethyl) phenyl]methyl}-5-hydroxy-3-oxo-2,3-dihydro-4-pyridazinyl)carbonyl]glycine 49a) Ethyl 6-(1,1-dimethylethyl)-2-{[4-(1,1-dimethylethyl)phenyl]methyl}-5-hydroxy-3-oxo-2,3-dihydro-4-pyridazinecarboxylate. Sodium hydride (42 mg, 1.00 mmol) was added to a solution of the compound from example 45c) (100 mg, 0.42 mmol) in N,N-Dimethylformamide (DMF) (2 mL) at 0° C. The reaction was brought to room temperature and stirred for 30 minutes. The temperature was then reduced to 0° C. and 4-tert-butylbenzyl bromide (0.08 mL, 0.42 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) give the title compound (116 mg, 72%). 1H NMR (400 MHz, DMSO-$d_6$) δ ppm 12.56 (s, 1H) 7.36 (ddd, J=8.46, 2.15, 2.02 Hz, 2H) 7.23 (d, J=8.59 Hz, 2H) 5.08 (s, 2H) 4.27 (q, J=7.16 Hz, 2H) 1.33 (s, 9H) 1.22-1.29 (m, 12H).

49b) N-[(6-(1,1-Dimethylethyl)-2-{[4-(1,1 -dimethylethyl)phenyl]methyl}-5-hydroxy-3-oxo-2,3-dihydro-4-pyridazinyl)carbonyl]glycine. Glycine, sodium salt (54 mg, 0.55 mmol) was added to a solution of the compound from example 49a) (107 mg, 0.28 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (68 mg, 59%). 1H NMR (400 MHz, DMSO-$d_6$) δ ppm 16.36 (s, 1H) 12.98 (s, 1H) 10.30 (t, J=5.43 Hz, 1H) 7.37 (ddd, J=8.46, 2.15, 2.02 Hz, 2H) 7.25 (d, J=8.34 Hz, 2H) 5.19 (s, 2H) 4.09 (d, J=5.56 Hz, 2H) 1.35 (s, 9H) 1.25 (s, 9H).

Example 50

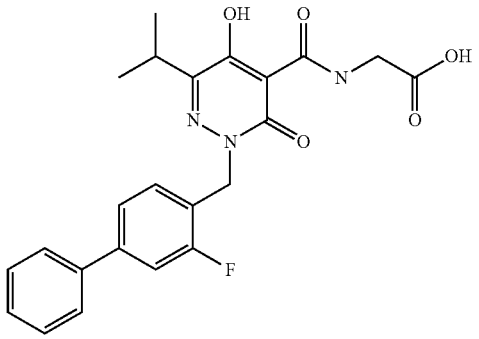

N-{[2-[(3-Fluoro-4-biphenylyl)methyl]-5-hydroxy-6-(1-methylethyl)-3-oxo-2,3-dihydro-4-pyridazinyl] carbonyl}glycine To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 40 mg, 0.09 mmol), phenylboronic acid (13.2 mg, 0.11 mmol), potassium carbonate (38 mg, 0.272 mmol), tetrakis (triphenylphosphine)palladium (0) (3 mg, 2.7 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered. and solvents removed under reduced pressure. The crude residue was purified by HPLC chromatography (ODS silica, gradient 15-95% acetonitrile/water (0.1% TFA)) to afford the title compound (10 mg, 0.023 mmol, 25% yield) as a white powder. 1H NMR (400 MHz, DMSO-$d_6$) d ppm 15.91 (s, 1H), 12.97 (br. s., 1H), 10.16 (t, J=5.56 Hz, 1H), 7.69 (d, J=7.33 Hz, 2H), 7.55 (dd, J=11.62, 1.52 Hz, 1H), 7.51-7.43 (m, 3H), 7.38-7.42 (m, 1H), 7.35 (t, J=7.96 Hz, 1H), 5.34 (s, 2H), 4.10 (d, J=5.81 Hz, 2H), 3.18 (sept, J=6.82 Hz, 1H), 1.19 (d, J=6.82 Hz, 6H). MS (ES+) m/e 440 [M+H]+.

Example 51

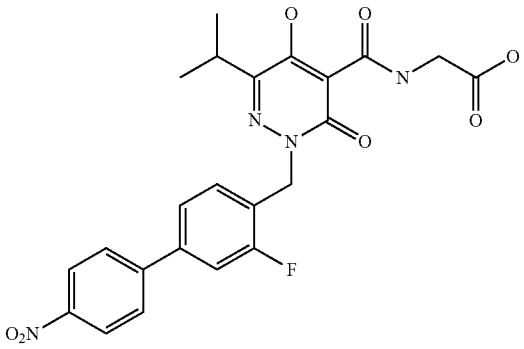

N-{[2-[(3-Fluoro-4'-nitro-4-biphenylyl)methyl]-5-hydroxy-6-(1-methylethyl)-3-oxo-2,3-dihydro-4-pyridazinyl]carbonyl}glycine To a 5 mL microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 1 g, 2.261 mmol), 4-nitrobenzenboronic acid (0.377 g, 2.261 mmol), potassium carbonate (0.938 g, 6.78 mmol), tetrakis(triphenylphosphine)palladium (0) (0.078 g, 0.068 mmol), 1,4-Dioxane (5 ml) and Water (1.667 ml). The mixture was irradiated at 100° C. for 20 minutes. The reaction mixture was diluted with water (10 ml) and acidified with 1N HCl to give a off-white precipitate that was collected by filtration. The mixture of products was purified by HPLC chromatography (ODS silica, gradient 10-100% acetonitrile/water (0.1% TFA)) to afford the title compound (450 mg, 0.920 mmol, 40.7% yield). 1H NMR (400 MHz, DMSO-$d_6$) d ppm 15.93 (s, 1H), 12.97 (br. s., 1H), 10.14 (t, J=5.68 Hz, 1H), 8.30 (td, J=9.16, 2.65, 2.34 Hz, 2H), 8.01 (td, J=9.16, 2.65, 2.34 Hz, 2H), 7.73 (dd, J=11.37, 1.77 Hz, 1H), 7.63 (dd, J=7.96, 1.89 Hz, 1H), 7.41 (t, J=7.96 Hz, 1H), 5.37 (s, 2H), 4.10 (d, J=5.56 Hz, 2H), 3.19 (sept, J=6.86 Hz, 1H), 1.19 (d, J=6.82 Hz, 6H). MS (ES+) m/e 485 [M+H]+.

Example 52

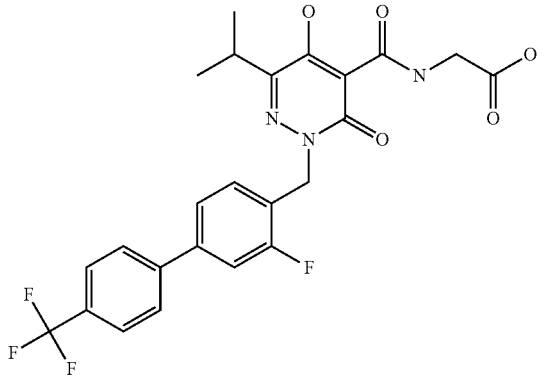

N-{[2-{[3-Fluoro-4'-(trifluoromethyl)-4-biphenylyl]methyl}-5-hydroxy-6-(1-methylethyl)-3-oxo-2,3-dihydro-4-pyridazinyl]carbonyl}glycine To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 40 mg, 0.09 mmol), (4-trifluoromethyl-phenyl)boronic acid (18.1 mg, 0.11 mmol), potassium carbonate (38 mg, 0.272 mmol), and tetrakis(triphenylphosphine)palladium (0) (3 mg, 2.7 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 15-95% acetonitrile/water (0.1% TFA)) to afford the title compound (25 mg, 0.049 mmol, 55% yield) as a white powder. 1H NMR (400 MHz, DMSO-$d_6$) d ppm 15.88 (s, 1H), 12.95 (s, 1H), 10.15 (t, J=6.06 Hz, 1H), 7.93 (d, J=8.08 Hz, 2H), 7.83 (d, J=8.59 Hz, 2H), 7.67 (dd, J=11.37, 1.77 Hz, 1H), 7.58 (dd, J=7.96, 1.89 Hz, 1H), 7.39 (t, J=7.96 Hz, 1 H), 5.36 (s, 2 H), 4.09 (d, J=5.56 Hz, 2H), 3.19 (m, 1H), 1.19 (d, J=6.82 Hz, 6H). MS (ES+) m/e 508 [M+H]+.

Example 53

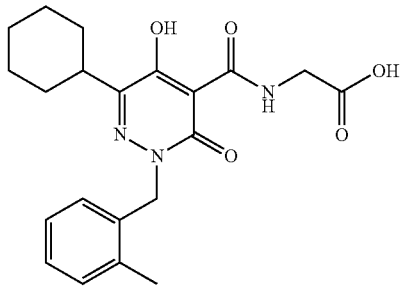

N-({6-Cyclohexyl-5-hydroxy-2-[(2-methylphenyl)methyl]-3-oxo-2,3-dihydro-4-pyridazinyl}carbonyl)glycine 53a) Ethyl 3-{2-[1-cyclohexyl-2-(ethyloxy)-2-oxoethylidene]hydrazino}-3-oxopropanoate. A solution of diethyl oxylate (4.1 mL, 30.0 mmol) in THF (50 mL) was cooled to −78° C. Cyclohexyl magnesium bromide (1.0M solution in THF, 36 mL, 36.0 mmol) was dropwise added and the solution stirred under a nitrogen atmosphere for 1.5 h at −78° C. The reaction was brought to 0° C. and quenched with 6N HCl. $Et_2O$ and $H_2O$ were added and the layers separated. The aqueous phase was backextracted with $Et_2O$ several times. The combined organic layers were washed with Brine, dried ($MgSO_4$), filtered and concentrated. The resulting residue was dissolved in EtOH (20 mL) and partitioned between two microwave vials. Ethyl-3-hydrazino-3-oxopropionate (2.41 g, 18.0 mmol) and catalytic AcOH (0.2 mL, 3.50 mmol) were added to each vial. The reactions were heated in the microwave at 150° C. for 1 h. The reactions were cooled and combined in a round bottom flask. The solvent was removed under reduced pressure and the resulting residue was azeotroped with Toluene several times. The product was purified by column chromatography ($SiO_2$, 10-30% EtOAc/Hexanes) to give the title compound (1.93 g, 21% over 2 steps). 1H NMR (400 MHz, DMSO-$d_6$) δ ppm 11.44-11.78 (m, 1H) 3.99-4.34 (m, 4H) 3.44-3.67 (m, 2H) 2.52-2.63 (m, 1H) 1.52-1.84 (m, 5H) 1.04-1.37 (m, 11H).

53b) Ethyl 6-cyclohexyl-5-hydroxy-3-oxo-2,3-dihydro-4-pyridazinecarboxylate. KHMDS (1.24 g, 6.19 mmol) was added in several portions to a solution of the compound from example 53a) (1.29 g, 4.13 mmol) in 1,4-dioxane at room temperature. The reaction was heated to reflux and stirred for 3 h. The reaction was cooled to room temperature and 6N HCl was added to precipitate the product. The solid was filtered and washed several times with $H_2O$ and Hexanes to give the title compound (795 mg, 72%). 1H NMR (400 MHz, DMSO-$d_6$) δ ppm 12.64 (s, 1H) 12.29 (s, 1H) 4.28 (q, J=7.07 Hz, 2H) 2.69-2.88 (m, 1H) 1.60-1.88 (m, 5H) 1.29-1.41 (m, 4H) 1.27 (t, J=7.07 Hz, 3H) 0.97-1.24 (m, 1H).

53c) Ethyl 6-cyclohexyl-5-hydroxy-2-[(2-methylphenyl)methyl]-3-oxo-2,3-dihydro-4-pyridazinecarboxylate. Sodium hydride (38 mg, 0.94 mmol) was added to a solution of the compound from example 53b) (100 mg, 0.38 mmol) in N,N-Dimethylformamide (DMF) (1.5 mL) at 0° C. The reaction was brought to room temperature and stirred for 30 minutes. The temperature was then reduced to 0° C. and 2-methylbenzyl bromide (0.05 mL, 0.38 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 15-30% EtOAc/Hexanes) to give the title compound (88 mg, 62%). 1H NMR (400 MHz, DMSO-$d_6$) δ ppm 12.22 (s, 1H) 7.06-7.22 (m, 3H) 7.01 (d, J=7.07 Hz, 1H) 5.14 (s, 2H) 4.26 (q, J=7.07 Hz, 2H) 2.77-2.91 (m, 1H) 2.37 (s, 3H) 1.55-1.89 (m, 5H) 1.28-1.42 (m, 4H) 1.25 (t, J=7.20 Hz, 3H) 1.05-1.23 (m, 1H).

53d) N-({6-Cyclohexyl-5-hydroxy-2-[(2-methylphenyl)methyl]-3-oxo-2,3-dihydro-4-pyridazinyl}carbonyl)glycine. Glycine, sodium salt (45 mg, 0.46 mmol) was added to a solution of the compound from example 53c) (86 mg, 0.23 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (43 mg, 47%). 1H NMR (400 MHz, DMSO-$d_6$) δ ppm 15.87 (s, 1H) 12.97 (s, 1H) 10.19 (t, J=5.56 Hz, 1H) 7.08-7.25 (m, 3H) 7.02 (d, J=7.07 Hz, 1H) 5.25 (s, 2H) 4.10 (d, J=5.81 Hz, 2H) 2.80-2.94 (m, 1H) 2.38 (s, 3H) 1.63-1.91 (m, 5H) 1.12-1.45 (m, 5H).

Example 54

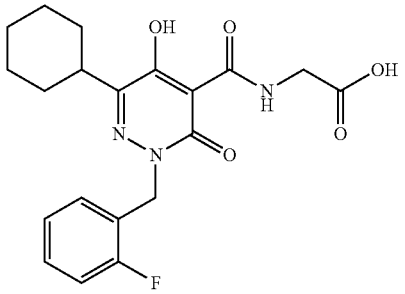

N-({6-Cyclohexyl-2-[(2-fluorophenyl)methyl]-5-hydroxy-3-oxo-2,3-dihydro-4-pyridazinyl}carbonyl) glycine 54a) Ethyl 6-cyclohexyl-2-[(2-fluorophenyl)methyl]-5-hydroxy-3-oxo-2,3-dihydro-4-pyridazinecarboxylate. Sodium hydride (38 mg, 0.94 mmol) was added to a solution of the compound from example 53b) (100 mg, 0.38 mmol) in N,N-Dimethylformamide (DMF) (1.5 mL) at 0° C. The reaction was brought to room temperature and stirred for 30 minutes. The temperature was then reduced to 0° C. and 2-fluorobenzyl bromide (0.05 mL, 0.38 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 15-30% EtOAc/Hexanes) to give the title compound (64 mg, 45%). 1H NMR (400 MHz, DMSO-$d_6$) δ ppm 12.27 (s, 1H) 7.31-7.39 (m, 1H) 7.11-7.24 (m, 3H) 5.20 (s, 2H) 4.26 (q, J=7.07 Hz, 2H) 2.78-2.89 (m, 1H) 1.61-1.87 (m, 5H) 1.28-1.40 (m, 4H) 1.25 (t, J=7.20 Hz, 3 H) 1.08-1.22 (m, 1H).

54b) N-({6-Cyclohexyl-2-[(2-fluorophenyl)methyl]-5-hydroxy-3-oxo-2,3-dihydro-4-pyridazinyl}carbonyl)glycine. Glycine, sodium salt (32 mg, 0.33 mmol) was added to a solution of the compound from example 54a) (61 mg, 0.16 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (30 mg, 46%). 1H NMR (400 MHz, DMSO-$d_6$) δ ppm 15.90 (s, 1H) 12.96 (s, 1H) 10.14 (t, J=5.68 Hz, 1H) 7.31-7.41 (m, 1H) 7.11-7.29 (m, 3H) 5.30 (s, 2H) 4.09 (d, J=5.56 Hz, 2H) 2.78-2.93 (m, 1H) 1.61-1.91 (m, 5H) 1.08-1.44 (m, 5H).

Example 55

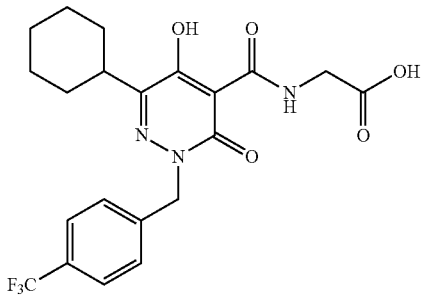

N-[(6-Cyclohexyl-5-hydroxy-3-oxo-2-{[4-(trifluoromethyl)phenyl]methyl}-2,3-dihydro-4-pyridazinyl) carbonyl]glycine 55a) Ethyl 6-cyclohexyl-5-hydroxy-3-oxo-2-{[4-(trifluoromethyl)phenyl]methyl}-2,3-dihydro-4-pyridazinecarboxylate. Sodium hydride (38 mg, 0.94 mmol) was added to a solution of the compound from example 53b) (100 mg, 0.38 mmol) in N,N-Dimethylformamide (DMF) (1.5 mL) at 0° C. The reaction was brought to room temperature and stirred for 30 minutes. The temperature was then reduced to 0° C. and 4-(trifluoromethyl)-benzyl bromide (90 mg, 0.38 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 15-30% EtOAc/Hexanes) to give the title compound (103 mg, 64%). 1H NMR (400 MHz, DMSO-$d_6$) δ ppm 12.30 (s, 1H) 7.72 (d, J=8.08 Hz, 2H) 7.46 (d, J=8.08 Hz, 2 H) 5.23 (s, 2H) 4.26 (q, J=7.07 Hz, 2H) 2.79-2.89 (m, 1H) 1.61-1.90 (m, 5H) 1.29-1.44 (m, 4 H) 1.25 (t, J=7.07 Hz, 3H) 1.12-1.22 (m, 1H).

55b) N-[(6-Cyclohexyl-5-hydroxy-3-oxo-2-{[4-(trifluoromethyl)phenyl]methyl}-2,3-dihydro-4-pyridazinyl)carbonyl]glycine. Glycine, sodium salt (45 mg, 0.47 mmol) was added to a solution of the compound from example 55a) (99 mg, 0.23 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (49 mg, 47%). 1H NMR (400 MHz, DMSO-$d_6$) δ ppm 10.40 (br. s., 1H) 7.70 (d, J=8.08 Hz, 2H) 7.46 (d, J=8.08 Hz, 2H) 5.27 (s, 2H) 3.93 (d, J=5.31 Hz, 2H) 2.81-2.97 (m, 1 H) 1.61-1.90 (m, 5H) 1.12-1.45 (m, 5H).

Example 56

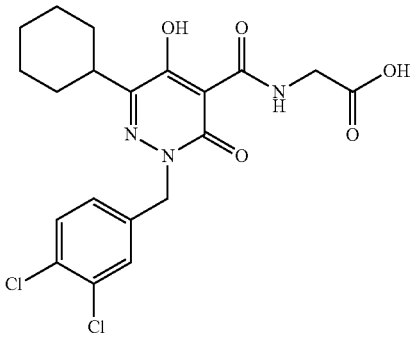

N-({6-cyclohexyl-2-[(3,4-dichlorophenyl)methyl]-5-hydroxy-3-oxo-2,3-dihydro-4-pyridazinyl}carbonyl) glycine 56a) Ethyl 6-cyclohexyl-2-[(3,4-dichlorophenyl)methyl]-5-hydroxy-3-oxo-2,3-dihydro-4-pyridazinecarboxylate. Sodium hydride (38 mg, 0.94 mmol) was added to a solution of the compound from example 53b) (100 mg, 0.38 mmol) in N,N-Dimethylformamide (DMF) (1.5 mL) at 0° C. The reaction was brought to room temperature and stirred for 30 minutes. The temperature was then reduced to 0° C. and 3,4-dichlorobenzyl bromide (0.07 mL, 0.48 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 15-35% EtOAc/Hexanes) to give the title compound (113 mg, 70%). 1H NMR (400 MHz, DMSO-$d_6$) δ ppm 12.32 (s, 1H) 7.62 (d, J=8.34 Hz, 1H) 7.54 (d, J=2.02 Hz, 1 H) 7.23 (dd, J=8.34, 2.02 Hz, 1H) 5.14 (s, 2H) 4.26 (q, J=7.07 Hz, 2H) 2.78-2.91 (m, 1H) 1.62-1.87 (m, 5 H) 1.29-1.44 (m, 4H) 1.25 (t, J=7.07 Hz, 3H) 1.13-1.22 (m, 1H).

56b) N-({6-Cyclohexyl-2-[(3,4-dichlorophenyl)methyl]-5-hydroxy-3-oxo-2,3-dihydro-4-pyridazinyl}carbonyl)glycine. Glycine, sodium salt (44 mg, 0.45 mmol) was added to a solution of the compound from example 56a) (96 mg, 0.23 mmol) in 2-methoxyethanol (1.5 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (77 mg, 74%). 1H NMR (400 MHz, DMSO-$d_6$) δ ppm 15.91 (s, 1H) 12.98 (s, 1H) 10.12 (t, J=5.56 Hz, 1H) 7.62 (d, J=8.08 Hz, 1H) 7.58 (d, J=2.02 Hz, 1H) 7.26 (dd, J=8.34, 2.02 Hz, 1H) 5.25 (s, 2H) 4.09 (d, J=5.81 Hz, 2H) 2.76-2.93 (m, 1H) 1.62-1.93 (m, 5H) 1.10-1.50 (m, 5H).

Example 57

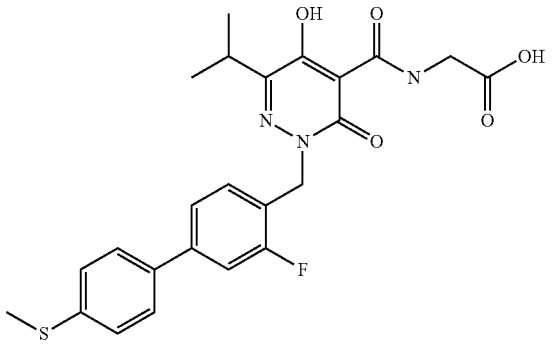

N-{[2-{[3-Fluoro-4'-(methylthio)-4-biphenylyl]methyl}-5-hydroxy-6-(1-methylethyl)-3-oxo-2,3-dihydro-4-pyridazinyl]carbonyl}glycine To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 75 mg, 0.17 mmol), [4-(methylthio)phenyl]boronic acid (34 mg, 0.20 mmol), potassium carbonate (70 mg, 0.51 mmol), and tetrakis(triphenylphosphine)palladium (0) (6 mg, 5 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by low pressure reverse phase c18 (ODS silica, gradient 15-95% acetonitrile/water) to afford the title compound (5 mg, 0.010 mmol, 6% yield) as an off white powder. 1H NMR (400 MHz, DMSO-$d_6$) d ppm 15.92 (s, 1H), 12.95 (s, 1H), 10.16 (t, J=5.43 Hz, 1H), 7.65 (d, J=8.34 Hz, 2H), 7.54 (dd, J=11.62, 1.52 Hz, 1H), 7.48 (dd, J=7.96, 1.64 Hz, 1H), 7.30-7.38 (m, 3H), 5.33 (s, 2H), 4.10 (d, J=5.81 Hz, 2 H), 3.31-3.34 (m, 3H), 3.18 (m, 1H), 1.19 (d, J=6.82 Hz, 6H). MS (ES+) m/e 486 [M+H]+.

Example 58

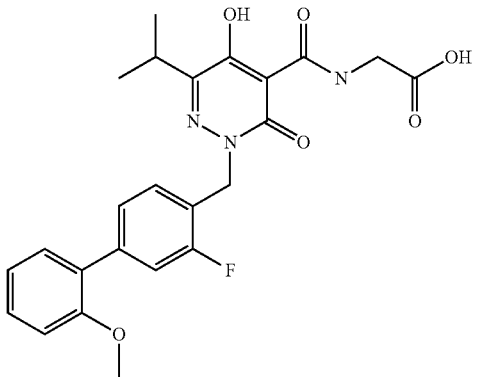

N-{[2-{[3-Fluoro-2'-(methyloxy)-4-biphenylyl]methyl}-5-hydroxy-6-(1-methylethyl)-3-oxo-2,3-dihydro-4-pyridazinyl]carbonyl}glycine To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 75 mg, 0.17 mmol), 2-methoxyphenyl boronic acid (31 mg, 0.20 mmol), potassium carbonate (70 mg, 0.51 mmol), and tetrakis(triphenylphosphine)palladium (0) (6 mg, 5 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified HPLC chromatography (ODS silica, gradient 15-95% acetonitrile/water) to afford the title compound (25 mg, 0.053 mmol, 31% yield) as a white powder. 1H NMR (400 MHz, DMSO-$d_6$) d ppm 15.91 (s, 1H), 12.93 (br. s., 1H), 10.16 (t, J=5.56 Hz, 1H), 7.23-7.41 (m, 5H), 7.12 (d, J=7.83 Hz, 1H), 7.03 (dt, J=7.39, 0.88 Hz, 1H), 5.33 (s, 2H), 4.10 (d, J=5.81 Hz, 2H), 3.77 (s, 3H), 3.19 (sept, J=6.86 Hz, 1H), 1.20 (d, J=6.82 Hz, 6H). MS (ES+) m/e 470 [M+H]+.

Example 59

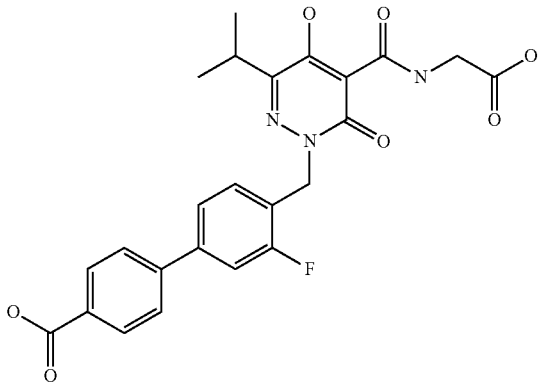

4'-{[5-{[(Carboxymethyl)amino]carbonyl}-4-hydroxy-3-(1-methylethyl)-6-oxo-1(6H)-pyridazinyl]methyl}-3'-fluoro-4-biphenylcarboxylic acid To a 5 ml microwave tube was added N-{[2-[(4-bromo-2-fluorophenyl)methyl]-5-hydroxy-6-(1-methylethyl)-3-oxo-2,3-dihydro-4-pyridazinyl]carbonyl}glycine (example 46(b), 75 mg, 0.17 mmol), 4-carboxybenzeneboronic acid (34 mg, 0.20 mmol), potassium carbonate (70 mg, 0.51 mmol), and tetrakis(triphenylphosphine)palladium (0) (6 mg, 5 μmol), 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (20 mg, 0.041 mmol, 24% yield) as a white powder. 1H NMR (400 MHz, DMSO-$d_6$) d ppm 15.93 (s, 1H), 13.03 (br. s., 2H), 10.15 (t, J=5.43 Hz, 1H), 8.01 (d, J=8.34 Hz, 2H), 7.83 (d, J=8.59 Hz, 2H), 7.64 (dd, J=11.37, 1.77 Hz, 1H), 7.57 (dd, J=7.96, 1.64 Hz, 1H), 7.38 (t, J=7.96 Hz, 1H), 5.35 (s, 2H), 4.10 (d, J=5.81 Hz, 2H), 3.19 (sept, J=6.86 Hz, 1H), 1.19 (d, J=6.82 Hz, 6 H). MS (ES+) m/e 484 [M+H]+.

Example 60

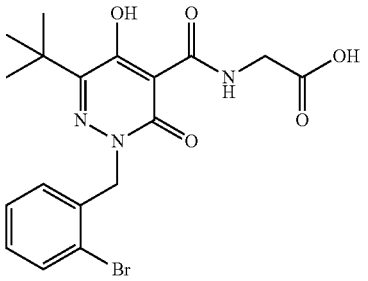

N-{[2-[(2-Bromophenyl)methyl]-6-(1,1-dimethylethyl)-5-hydroxy-3-oxo-2,3-dihydro-4-pyridazinyl]carbonyl}glycine 60a) Ethyl 2-[(2-bromophenyl)methyl]-6-(1,1-dimethylethyl)-5-hydroxy-3-oxo-2,3-dihydro-4-pyridazinecarboxylate. Sodium hydride (37 mg, 0.92 mmol) was added to a solution of the compound from example 45c) (100 mg, 0.42 mmol) in N,N-Dimethylformamide (DMF) (1.5 mL) at 0° C. The reaction was brought to room temperature and stirred for 30 minutes. The temperature was then reduced to 0° C. and 2-bromobenzyl bromide (104 mg, 0.42 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 10-30% EtOAc/Hexanes) to give the title compound (96 mg, 56%). 1H NMR (400 MHz, DMSO-$d_6$) δ ppm 12.68 (s, 1H) 7.65 (dd, J=8.08, 1.26 Hz, 1H) 7.36 (td, J=7.52, 1.14 Hz, 1H) 7.25 (td, J=7.64, 1.64 Hz, 1H) 7.11 (dd, J=7.71, 1.64 Hz, 1H) 5.20 (s, 2H) 4.29 (q, J=7.16 Hz, 2 H) 1.25 (s, 9H) 1.23-1.30 (m, 3H).

60b) N-{[2-[(2-Bromophenyl)methyl]-6-(1,1-dimethylethyl)-5-hydroxy-3-oxo-2,3-dihydro-4-pyridazinyl]carbonyl}glycine. Glycine, sodium salt (44 mg, 0.45 mmol) was added to a solution of the compound from example 60a) (93 mg, 0.23 mmol) in 2-methoxyethanol (2 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes to give the title compound (29 mg, 29%). 1H NMR (400 MHz, DMSO-$d_6$) δ ppm 16.43 (s, 1H) 12.99 (s, 1H) 10.26 (t, J=5.18 Hz, 1H) 7.67 (dd, J=7.96, 1.14 Hz, 1H) 7.37 (td, J=7.58, 1.26 Hz, 1H) 7.27 (td, J=7.71, 1.77 Hz, 1H) 7.16 (dd, J=7.71, 1.64 Hz, 1H) 5.31 (s, 2H) 4.11 (d, J=5.81 Hz, 2H) 1.27 (s, 9H).

Example 61

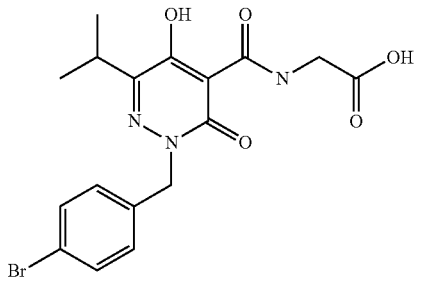

N-{[2-[(4-Bromophenyl)methyl]-5-hydroxy-6-(1-methylethyl)-3-oxo-2,3-dihydro-4-pyridazinyl] carbonyl}glycine To a solution of ethyl 5-hydroxy-6-(1-methylethyl)-3-oxo-2,3-dihydro-4-pyridazinecarboxylate (example 46a, 1.32 g, 5.83 mmol) in N,N-Dimethylformamide (DMF) (30 ml) at 0° C. was added sodium hydride (0.5 g, 14.58 mmol) in portions. The reaction mixture was stirred at room temperature for 30 minutes and then cooled back to 0° C. and 4-bromobenzyl bromide (1.46 g, 5.83 mmol) was added. The mixture was stirred at ambient temperature for 2 hours then quenched with 1N HCl (10 ml). The aqueous solution was extracted with ethyl acetate (2×50 ml), the organic layers combined, dried over Magnesium sulfate, filtered and solvents removed with rotary evaporation. The crude residue was dissolved in 2-methoxyethanol (10 ml), place in a 20 ml microwave tube and glycine sodium salt (0.75 g, 7.7 mmol) was added. The mixture was irradiated at 150° C. for 20 minutes, diluted with water (15 ml) and acidified with 1N HCl to cause a precipitate. The precipitate was collected by filtration and dried to give the product as an off white solid (0.750 g, 1.77 mmol, 30.3%) 1H NMR (400 MHz, DMSO-$d_6$) d ppm 15.89 (s, 1H), 12.97 (s, 1H), 10.16 (t, J=5.31 Hz, 1H), 7.55 (d, J=8.34 Hz, 2H), 7.26 (d, J=8.34 Hz, 2 H), 5.22 (s, 2H), 4.10 (d, J=5.81 Hz, 2H), 3.18 (m, 1H), 1.19 (d, J=6.82 Hz, 6H). MS (ES+) m/e 425 [M+H]+.

Example 62

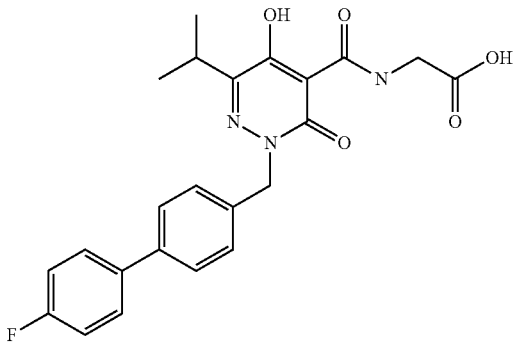

N-{[2-[(4'-Fluoro-4-biphenylyl)methyl]-5-hydroxy-6-(1-methylethyl)-3-oxo-2,3-dihydro-4-pyridazinyl] carbonyl}glycine To a 5 ml microwave tube was added N-{[2-[(4-bromophenyl)methyl]-5-hydroxy-6-(1-methylethyl)-3-oxo-2,3-dihydro-4-pyridazinyl]carbonyl}glycine (example 61, 40 mg, 0.094 mmol), 4-fluorobenzeneboronic acid (14 mg, 0.10 mmol), potassium carbonate (40 mg, 0.290 mmol), and tetrakis(triphenylphosphine)palladium (0) (6 mg, 5 μmol) in 1,4-Dioxane (1.5 ml) and Water (0.500 ml). The mixture was irradiated at 100° C. for 20 minutes, diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (16.6 mg, 0.038 mmol, 40% yield) as a white powder. 1H NMR (400 MHz, DMSO-$d_6$) d ppm 15.88 (s, 1H), 12.99 (br. s., 1H), 10.20 (t, J=5.56 Hz, 1H), 7.65-7.74 (m, 2H), 7.62 (d, J=8.08 Hz, 2H), 7.39 (d, J=8.34 Hz, 2H), 7.23-7.33 (m, 2H), 5.29 (s, 2H), 4.10 (d, J=5.81 Hz, 2H), 3.20 (sept, J=6.78 Hz, 1H), 1.22 (d, J=6.82 Hz, 6H). MS (ES+) m/e 440 [M+H]+.

Example 63

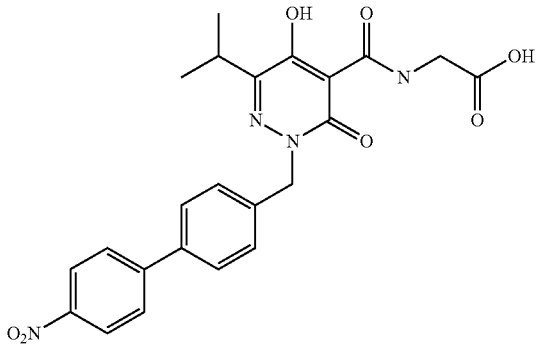

N-({5-Hydroxy-6-(1-methylethyl)-2-[(4'-nitro-4-biphenylyl)methyl]-3-oxo-2,3-dihydro-4-pyridazinyl}carbonyl)glycine To a 5 ml microwave tube was added N-{[2-[(4-bromophenyl)methyl]-5-hydroxy-6-(1-methylethyl)-3-oxo-2,3-dihydro-4-pyridazinyl]carbonyl}glycine (example 61, 40 mg, 0.094 mmol), 4-nitrobenzeneboronic acid (19 mg, 0.10 mmol), potassium carbonate (40 mg, 0.290 mmol), and tetrakis(triphenylphosphine)palladium (0) (6 mg, 5 μmol) in 1,4-Dioxane (1.5 ml) and Water (0.500 ml). The mixture was irradiated at 100° C. for 20 minutes, diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (16.8 mg, 0.036 mmol, 38% yield) as a white powder. 1H NMR (400 MHz, DMSO-$d_6$) d ppm 15.90 (s, 1H), 12.96 (br. s., 1H), 10.19 (t, J=5.05 Hz, 1H), 8.30 (ddd, J=9.09, 2.53, 2.27 Hz, 2H), 7.95 (ddd, J=9.35, 2.53, 2.27 Hz, 2H), 7.78 (d, J=8.34 Hz, 2H), 7.45 (d, J=8.34 Hz, 2H), 5.33 (s, 2H), 4.10 (d, J=5.56 Hz, 2H), 3.20 (qq, J=7.07, 6.87 Hz, 1H), 1.22 (d, J=6.82 Hz, 6H). MS (ES+) m/e 467 [M+H]+.

Example 64

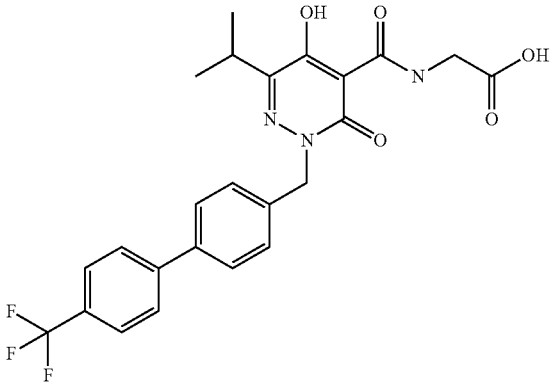

N-[(5-Hydroxy-6-(1 -methylethyl)-3-oxo-2-{[4'-(trifluoromethyl)-4-biphenylyl]methyl}-2,3-dihydro-4-pyridazinyl)carbonyl]glycine To a 5 ml microwave tube was added N-{[2-[(4-bromophenyl)methyl]-5-hydroxy-6-(1-methylethyl)-3-oxo-2,3-dihydro-4-pyridazinyl]carbonyl}glycine (example 61, 40 mg, 0.094 mmol), 4-trifluoromethylphenylboronic acid (22 mg, 0.10 mmol), potassium carbonate (40 mg, 0.290 mmol), and tetrakis(triphenylphosphine)palladium (0) (6 mg, 5 μmol) in 1,4-Dioxane (1.5 ml) and Water (0.500 ml). The mixture was irradiated at 100° C. for 20 minutes, diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (17.1 mg, 0.035 mmol, 37% yield) as a white powder. 1H NMR (400 MHz, DMSO-$d_6$) d ppm 15.89 (s, 1H), 12.98 (br. s., 1H), 10.19 (t, J=5.68 Hz, 1H), 7.88 (d, 2H), 7.81 (d, 2H), 7.72 (d, J=8.34 Hz, 2H), 7.43 (d, J=8.34 Hz, 2H), 5.32 (s, 2H), 4.10 (d, J=5.56 Hz, 2H), 3.20 (sept, J=6.78 Hz, 1H), 1.22 (d, J=6.82 Hz, 6H). MS (ES+) m/e 490 [M+H]+.

Example 65

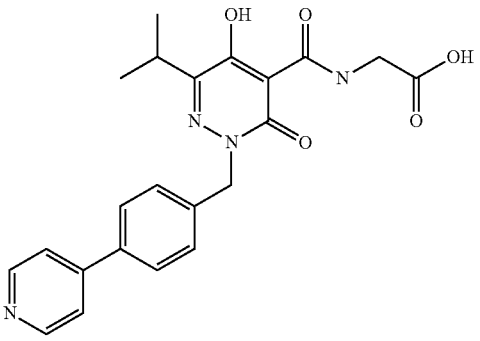

N-[(5-Hydroxy-6-(1-methylethyl)-3-oxo-2-{[4-(4-pyridinyl)phenyl]methyl}-2,3-dihydro-4-pyridazinyl)carbonyl]glycine To a 5 ml microwave tube was added N-{[2-[(4-bromophenyl)methyl]-5-hydroxy-6-(1-methylethyl)-3-oxo-2,3-dihydro-4-pyridazinyl]carbonyl}glycine (example 61, 40 mg, 0.094 mmol), 4-pyridinylboronic acid (14 mg, 0.10 mmol), potassium carbonate (40 mg, 0.290 mmol), and tetrakis(triphenylphosphine)palladium (0) (6 mg, 5 μmol) in 1,4-Dioxane (1.5 ml) and Water (0.500 ml). The mixture was irradiated at 100° C. for 20 minutes, diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (11.0 mg, 0.026 mmol, 28% yield) as a white powder. 1H NMR (400 MHz, DMSO-$d_6$) d ppm 15.91 (s, 1H), 13.01 (s, 1H), 10.17 (t, J=5.56 Hz, 1H), 8.80 (d, J=6.32 Hz, 2H), 8.04 (d, J=6.32 Hz, 2H), 7.91 (d, J=8.34 Hz, 2H), 7.49 (d, J=8.34 Hz, 2H), 5.35 (s, 2H), 4.10 (d, J=5.56 Hz, 2H), 3.20 (m, 1H), 1.22 (d, J=6.82 Hz, 6 H). MS (ES+) m/e 423 [M+H]+.

Example 66

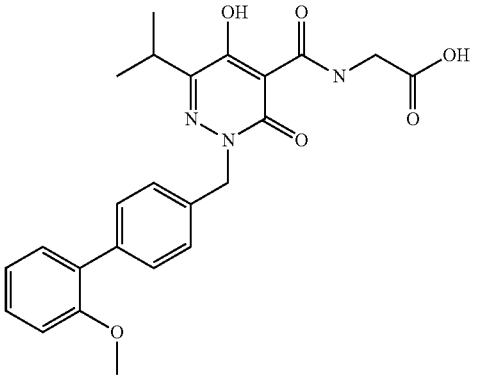

N-[(5-Hydroxy-6-(1-methylethyl)-2-{[2'-(methyloxy)-4-biphenylyl]methyl}-3-oxo-2,3-dihydro-4-pyridazinyl)carbonyl]glycine To a 5 ml microwave tube was added N-{[2-[(4-bromophenyl)methyl]-5-hydroxy-6-(1-methylethyl)-3-oxo-2,3-dihydro-4-pyridazinyl]carbonyl}glycine (example 61, 40 mg, 0.094 mmol), 2-methoxyphenyl boronic acid (17.2 mg, 0.10 mmol), potassium carbonate (40 mg, 0.290 mmol), and tetrakis(triphenylphosphine)palladium (0) (6 mg, 5 μmol) in 1,4-Dioxane (1.5 ml) and Water (0.500 ml). The mixture was irradiated at 100° C. for 20 minutes, diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (15.0 mg, 0.033 mmol, 35% yield) as a white powder. 1H NMR (400 MHz, DMSO-$d_6$) d ppm 15.88 (s, 1H), 12.97 (s, 1H), 10.21 (t, J=5.94 Hz, 1H), 7.41-7.47 (m, 2H), 7.31-7.37 (m, 3H), 7.26 (dd, J=7.58, 1.77 Hz, 1H), 7.10 (d, J=7.58 Hz, 1H), 7.01 (dt, J=7.45, 1.01 Hz, 1H), 5.28 (s, 2H), 4.10 (d, J=5.81 Hz, 2H), 3.74 (s, 3H), 3.20 (m, 1H), 1.23 (d, J=6.82 Hz, 6H). MS (ES+) m/e 452 [M+H]+.

Example 67

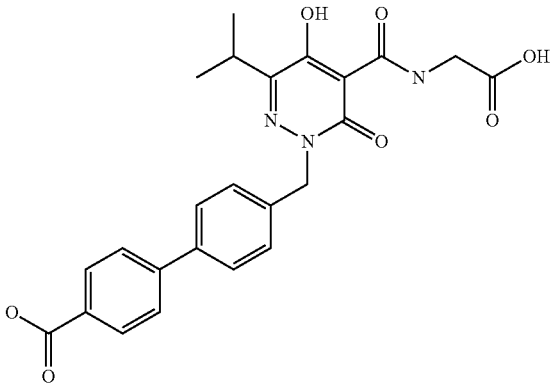

4'-{[5-{[(Carboxymethyl)amino]carbonyl}-4-hydroxy-3-(1-methylethyl)-6-oxo-1(6H)-pyridazinyl]methyl}-4-biphenylcarboxylic acid To a 5 ml microwave tube was added N-{[2-[(4-bromophenyl)methyl]-5-hydroxy-6-(1-methylethyl)-3-oxo-2,3-dihydro-4-pyridazinyl]carbonyl}glycine (example 61, 40 mg, 0.094 mmol), 4-carboxybenzeneboronic acid (19 mg, 0.10 mmol), potassium carbonate (40 mg, 0.290 mmol), and tetrakis(triphenylphosphine)palladium (0) (6 mg, 5 μmol) in 1,4-Dioxane (1.5 ml) and Water (0.500 ml). The mixture was irradiated at 100° C. for 20 minutes, diluted with water (5 ml), acidified with 1N HCl (2 ml), and extracted with ethyl acetate (20 ml). The organic phase was washed with brine, dried over MgSO4, filtered, and solvents removed under reduced pressure. The crude residue was purified by HPLC chromatography (ODS silica, gradient 15-95% acetonitrile/water (0.1% TFA)) to afford the title compound (16.0 mg, 0.034 mmol, 36% yield) as a white powder. 1H NMR (400 MHz, DMSO-$d_6$) d ppm 15.89 (s, 1H), 12.99 (br. s., 1H), 10.19 (t, J=5.68 Hz, 1H), 8.01 (m, 2H), 7.78 (m, 2H), 7.72 (d, J=8.34 Hz, 2H), 7.42 (d, J=8.59 Hz, 2 H), 5.31 (s, 2H), 4.10 (d, J=5.56 Hz, 2H), 3.20 (qq, J=6.85, 6.69 Hz, 1H), 1.22 (d, J=6.82 Hz, 6 H). MS (ES+) m/e 466 [M+H]+.

Example 68

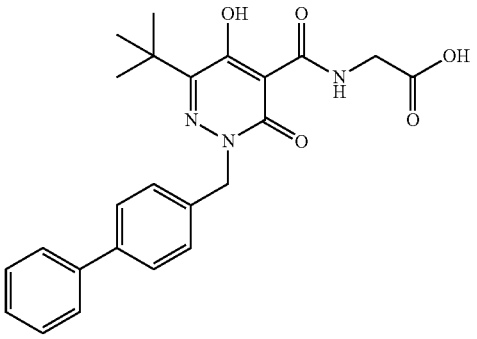

N-{[2-(4-Biphenylylmethyl)-6-(1,1-dimethylethyl)-5-hydroxy-3-oxo-2,3-dihydro-4-pyridazinyl]carbonyl}glycine 68a) Ethyl 2-(4-biphenylylmethyl)-6-(1,1-dimethylethyl)-5-hydroxy-3-oxo-2,3-dihydro-4-pyridazinecarboxylate. Sodium hydride (34 mg, 0.86 mmol) was added to a solution of the compound from example 45c) (94 mg, 0.39 mmol) in N,N-Dimethylformamide (DMF) (1.5 mL) at 0° C. The reaction was brought to room temperature and stirred for 30 minutes. The temperature was then reduced to 0° C. and 4-(bromomethyl)-biphenyl (97 mg, 0.39 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 20-50% EtOAc/Hexanes) to give the title compound (108 mg, 68%). 1H NMR (400 MHz, DMSO-$d_6$) δ ppm 12.60 (s, 1H) 7.60-7.68 (m, 4H) 7.31-7.51 (m, 5H) 5.17 (s, 2H) 4.28 (q, J=7.07 Hz, 2H) 1.33 (s, 9H) 1.27 (t, J=7.20 Hz, 3H).

68b) N-{[2-(4-Biphenylylmethyl)-6-(1,1-dimethylethyl)-5-hydroxy-3 -oxo-2,3 -dihydro-4-pyridazinyl]carbonyl}glycine. Glycine, sodium salt (52 mg, 0.53 mmol) was added to a solution of the compound from example 68a) (108 mg, 0.27 mmol) in 2-methoxyethanol (2 mL) at room temperature. The reaction was heated to reflux and stirred for 2 h. The reaction was cooled back to room temperature and $H_2O$ was added. The solution was filtered and 1N HCl was added to precipitate the product. The product was filtered and washed with $H_2O$ and Hexanes. The product was purified by recrystallization from hot AcOH to give the title compound (44 mg, 37%). 1H NMR (400 MHz, DMSO-$d_6$) δ ppm 16.40

(s, 1H) 12.97 (s, 1H) 10.31 (t, J=5.43 Hz, 1H) 7.59-7.70 (m, 4H) 7.39-7.50 (m, 4H) 7.31-7.39 (m, 1H) 5.28 (s, 2H) 4.11 (d, J=5.56 Hz, 2H) 1.36 (s, 9H).

Example 69

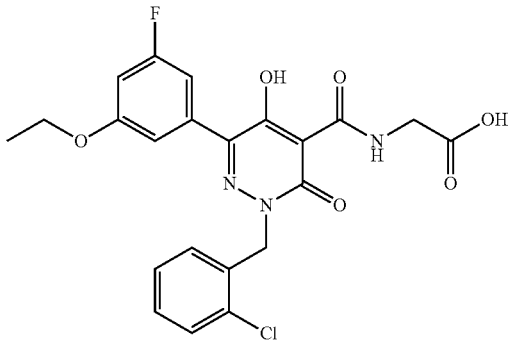

N-({2-[(2-Chlorophenyl)methyl]-6-[3-(ethyloxy)-5-fluorophenyl]-5-hydroxy-3-oxo-2,3-dihydro-4-pyridazinyl}carbonyl)glycine 69a) Ethyl 6-[3-(ethyloxy)-5-fluorophenyl]-5-hydroxy-3-oxo-2,3-dihydro-4-pyridazinecarboxylate. KHMDS (7.28 g, 36.50 mmol) was added in several portions to a solution of the compound from example 30a) (5.00 g, 14.60 mmol) in 1,4-dioxane (55 mL) at room temperature. The reaction was heated to reflux and stirred for 3 h. The reaction was cooled to room temperature and 1N HCl was added to precipitate the product. The solid was filtered and washed with $H_2O$ and Hexanes to give a mixture of the compound from example 30b) and the title compound. The product was purified by preparative reversed phase HPLC (80% $NH_4OAc$ (aq) pH 6.8) to give the title compound (263 mg, 6%). 1H NMR (400 MHz, DMSO-$d_6$) δ ppm 13.11 (s, 1H) 7.01-7.13 (m, 2H) 6.91 (dt, J=10.93, 2.37 Hz, 1H) 4.31 (q, J=7.07 Hz, 2H) 4.07 (q, J=7.07 Hz, 2H) 1.34 (t, J=6.95 Hz, 3H) 1.29 (t, J=7.07 Hz, 3H).

69b) Ethyl 2-[(2-chlorophenyl)methyl]-6-[3-(ethyloxy)-5-fluorophenyl]-5-hydroxy-3-oxo-2,3-dihydro-4-pyridazinecarboxylate. Sodium hydride (31 mg, 0.78 mmol) was added to a solution of the compound from example 69a) (100 mg, 0.31 mmol) in N,N-Dimethylformamide (DMF) (1.5 mL) at 0° C. The reaction was brought to room temperature and stirred for 30 minutes. The temperature was then reduced to 0° C. and 2-chlorobenzyl bromide (0.04 mL, 0.31 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 25-55% EtOAc/Hexanes) to give the title compound (69 mg, 50%). 1H NMR (400 MHz, DMSO-$d_6$) δ ppm 7.47-7.54 (m, 1H) 7.28-7.39 (m, 2H) 7.17-7.24 (m, 1H) 7.03-7.10 (m, 2H) 6.91 (dt, J=11.05, 2.31 Hz, 1H) 5.34 (s, 2H) 4.30 (q, J=7.07 Hz, 2H) 4.04 (q, J=6.82 Hz, 2H) 1.33 (t, J=6.95 Hz, 3H) 1.28 (t, J=7.20 Hz, 3H).

69c) N-({2-[(2-Chlorophenyl)methyl]-6-[3-(ethyloxy)-5-fluorophenyl]-5-hydroxy-3-oxo-2,3-dihydro-4-pyridazinyl}carbonyl)glycine. Glycine, sodium salt (29 mg, 0.30 mmol) was added to a solution of the compound from example 69b) (66 mg, 0.15 mmol) in 2-methoxyethanol (1.5 mL) at room temperature. The reaction was heated to reflux and stirred for 1.5 h. The reaction was cooled back to room temperature and $H_2O$ was added followed by 1N HCl to precipitate the product. The product was filtered and washed with $H_2O$ and Hexanes to give the title compound (61 mg, 86%). 1H NMR (400 MHz, DMSO-$d_6$) δ ppm 13.02 (s, 1H) 10.19 (t, J=5.18 Hz, 1H) 7.52 (dd, J=7.71, 1.64 Hz, 1H) 7.30-7.40 (m, 2H) 7.24-7.30 (m, 1H) 7.10-7.20 (m, 2H) 6.95 (dt, J=11.05, 2.31 Hz, 1H) 5.46 (s, 2H) 4.14 (d, J=5.56 Hz, 2H) 4.04 (q, J=6.99 Hz, 2H) 1.33 (t, J=6.95 Hz, 3H).

Example 70

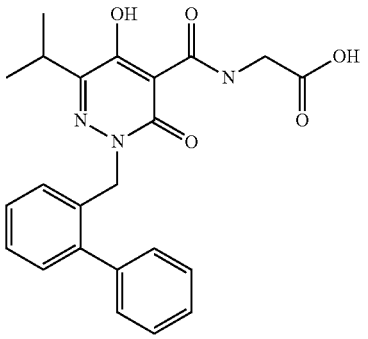

N-{[2-(2-Biphenylylmethyl)-5-hydroxy-6-(1-methylethyl)-3-oxo-2,3-dihydro-4-pyridazinyl]carbonyl}glycine 70a) Ethyl 2-(2-biphenylylmethyl)-5-hydroxy-6-(1-methylethyl)-3-oxo-2,3-dihydro-4-pyridazinecarboxylate. To a solution of ethyl 5-hydroxy-6-(1-methylethyl)-3-oxo-2,3-dihydro-4-pyridazinecarboxylate (example 46(a), 125 mg, 0.55 mmol) in N,N-Dimethylformamide (DMF) (5 ml) at 0° C. was added sodium hydride (55 mg, 0.138 mmol) in portions. The reaction mixture was stirred at room temperature for 45 minutes and then cooled back to 0° C. and 2-phenylbenzyl bromide (101 μl, 0.55 mmol) was added. The mixture was stirred at ambient temperature for 3 hours then quenched with 1N HCl (3 ml) extracted with ethyl acetate (2×20 ml). The organic layers were combined, dried over Magnesium sulfate, filtered and solvents removed with rotary evaporation. The crude oil was purified by flash column chromatography (10-100% ethyl acetate in hexanes) to provide the title compound ethyl 2-(2-biphenylylmethyl)-5-hydroxy-6-(1-methylethyl)-3-oxo-2,3-dihydro-4-pyridazinecarboxylate (126 mg, 0.32 mmol, 58% yield) as a pale yellow oil that was used immediately in the next step. MS (ES+) m/e 393 [M+H]+.

70b) N-{[2-(2-Biphenylylmethyl)-5-hydroxy-6-(1-methylethyl)-3-oxo-2,3-dihydro-4-pyridazinyl]carbonyl}glycine. To a 20 mL microwave tube was added the product of example 70a) (0.125 g, 0.318 mmol) and Glycine Sodium Salt (0.046 g, 0.477 mmol) in 2-methoxyethanol (2 ml) and the mixture was irradiated at 150° C. for 20 minutes. The reaction mixture was diluted with water (4 ml) and acidified with 1N HCl. The gelatinous aqueous solution was extracted with ethyl acetate. The organic phase was dried over MgSO4, filtered, and solvents removed under reduced pressure. The crude residue was purified by HPLC chromatography (ODS silica, gradient 25-95% acetonitrile/water (0.1% TFA)) to afford the title compound (84.0 mg, 0.199 mmol, 62% yield) as an off white powder. 1H NMR (400 MHz, DMSO-$d_6$) d ppm 15.83 (s, 1H), 12.94 (s, 1 H), 10.09 (t, J=5.68 Hz, 1H), 7.29-7.50 (m, 7H), 7.22-7.28 (m, 1H), 7.10-7.16 (m, 1H), 5.25 (s, 2H), 4.07 (d, J=5.56 Hz, 2H), 3.13 (sept, J=6.78 Hz, 1H), 1.13 (d, J=6.82 Hz, 6H). MS (ES+) m/e 422 [M+H]+.

Example 71

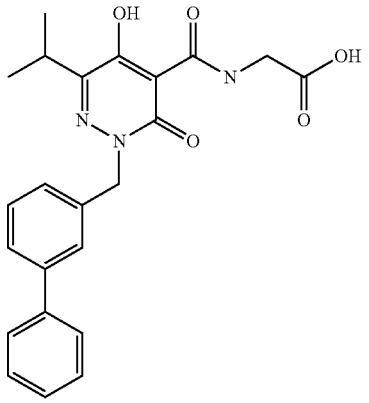

N-{[2-(3-Biphenylylmethyl)-5-hydroxy-6-(1-methylethyl)-3-oxo-2,3-dihydro-4-pyridazinyl]carbonyl}glycine 71a) Ethyl 2-(3-biphenylylmethyl)-5-hydroxy-6-(1-methylethyl)-3-oxo-2,3-dihydro-4-pyridazinecarboxylate. To a solution of ethyl 5-hydroxy-6-(1-methylethyl)-3-oxo-2,3-dihydro-4-pyridazinecarboxylate (example 46(a), 0.125 g, 0.55 mmol) in N,N-Dimethylformamide (DMF) (5 ml) at 0° C. was added sodium hydride (0.055 g, 0.138 mmol) in portions. The reaction mixture was stirred at room temperature for 45 minutes and then cooled back to 0° C. and 3-phenylbenzyl bromide (0.137 g, 0.55 mmol) was added. The mixture was stirred at ambient temperature for 3 hours then quenched with 1N HCl (3 ml) extracted with ethyl acetate (2×20 ml). The organic layers were combined, dried over Magnesium sulfate, filtered and solvents removed with rotary evaporation. The crude oil was purified by flash column chromatography (10-100% ethyl acetate in hexanes) to provide the title compound ethyl 2-(2-biphenylylmethyl)-5-hydroxy-6-(1-methylethyl)-3-oxo-2,3-dihydro-4-pyridazinecarboxylate (125 mg, 0.32 mmol, 58% yield) as a pale yellow solid that was used immediately in the next step. MS (ES+) m/e 393 [M+H]+

71b) N-{[2-(3-Biphenylylmethyl)-5-hydroxy-6-(1-methylethyl)-3-oxo-2,3-dihydro-4-pyridazinyl]carbonyl}glycine. To a 20 mL microwave tube was added the product of example 18a (0.125 g, 0.318 mmol) and Glycine Sodium Salt (0.046 g, 0.477 mmol) in MethoxyEthanol (2 ml) and the mixture was irradiated at 150° C. for 20 minutes. The reaction mixture was diluted with water (4 ml), acidified with 1N HCl, and extracted with ethyl acetate. The organic phase was dried over MgSO4, filtered, and solvents removed under reduced pressure. The crude residue was purified by HPLC chromatography (ODS silica, gradient 25-95% acetonitrile/water (0.1% TFA)) to afford the title compound (94.0 mg, 0.223 mmol, 70% yield) as an off white powder. 1H NMR (400 MHz, DMSO-$d_6$) d ppm 15.88 (s, 1H), 12.97 (br. s., 1H), 10.19 (t, J=5.56 Hz, 1 H), 7.54-7.70 (m, 4H), 7.40-7.51 (m, 3H), 7.37 (tt, J=7.33, 1.26 Hz, 1H), 7.28 (d, J=7.83 Hz, 1H), 5.33 (s, 2H), 4.09 (d, J=5.81 Hz, 2H), 3.19 (sept, J=6.82 Hz, 1H), 1.21 (d, J=6.82 Hz, 6H). MS (ES+) m/e 422 [M+H]+.

Example 72

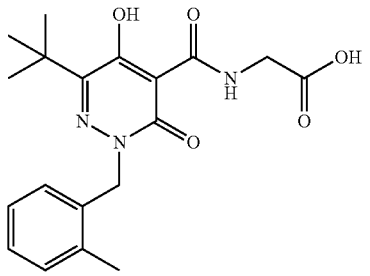

N-({6-(1,1-Dimethylethyl)-5-hydroxy-2-[(2-methylphenyl)methyl]-3-oxo-2,3-dihydro-4-pyridazinyl}carbonyl)glycine 72a) Ethyl 6-(1,1-dimethylethyl)-5-hydroxy-2-[(2-methylphenyl)methyl]-3-oxo-2,3-dihydro-4-pyridazinecarboxylate. Sodium hydride (42 mg, 1.05 mmol) was added to a solution of the compound from example 45c) (100 mg, 0.416 mmol) in N,N-Dimethylformamide (DMF) (1.5 ml) at 0° C. The reaction was brought to room temperature and stirred for 40 minutes. The temperature was then reduced to 0° C. and 1-(bromomethyl)-2-methylbenzene (0.06 ml, 0.45 mmol) was added. The reaction was brought to room temperature and stirred for 3 h followed by addition of 1N HCl. The solution was diluted with $H_2O$ and EtOAc and the layers separated. The aqueous layer was backextracted with EtOAc several times. The combined organic layers were washed with Brine, dried ($MgSO_4$), filtered and concentrated. The product was purified by column chromatography ($SiO_2$, 10-25% EtOAc/Hexanes) to give the title compound (74 mg, 52%). 1H NMR (400 MHz, DMSO-$d_6$) δ ppm 12.57 (s, 1H) 7.05-7.23 (m, 4H) 5.14 (s, 2H) 4.28 (q, J=7.16 Hz, 2H) 2.36 (s, 3H) 1.23-1.31 (m, 12H).

72b) N-({6-(1,1-Dimethylethyl)-5-hydroxy-2-[(2-methylphenyl)methyl]-3-oxo-2,3-dihydro-4-pyridazinyl}carbonyl)glycine. Glycine, sodium salt (37 mg, 0.38 mmol) was added to a solution of the compound from example 72a) (66 mg, 0.19 mmol) in 2-methoxyethanol (1.5 mL) at room temperature. The reaction was heated to reflux and stirred for 2 h. The reaction was then cooled to room temperature and $H_2O$ was added. The solution was filtered and 1N HCl was added to precipitate the product. The product was filtered and purified by precipitation from $CH_2Cl_2$/Hexanes to give the title compound as an off-white solid (54 mg, 75%). 1H NMR (400 MHz, DMSO-$d_6$) δ ppm 12.99 (s, 1H)

10.31 (t, J=5.43 Hz, 1H) 7.07-7.23 (m, 4H) 5.25 (s, 2H) 4.10 (d, J=5.56 Hz, 2H) 2.37 (s, 3H) 1.31 (s, 9H).

Example 73

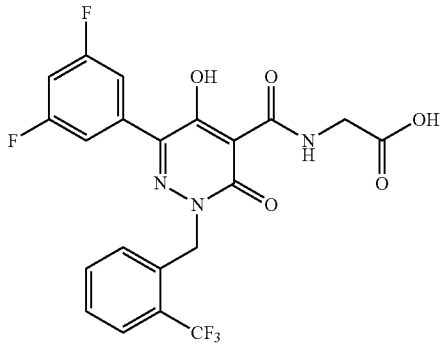

N-[(6-(3,5-Difluorophenyl)-5-hydroxy-3-oxo-2-{[2-(trifluoromethyl)phenyl]methyl}-2,3-dihydro-4-pyridazinyl)carbonyl]glycine 73a) Ethyl 6-(3,5-difluorophenyl)-5-hydroxy-3-oxo-2-{[2-(trifluoromethyl)phenyl]methyl}-2,3-dihydro-4-pyridazinecarboxylate. Sodium hydride (33.8 mg, 0.844 mmol) was added to a solution of the compound from example 30b) (100 mg, 0.338 mmol) in N,N-Dimethylformamide (DMF) (2 ml) at 0° C. The reaction was brought to room temperature and stirred for 40 minutes. The temperature was then reduced to 0° C. and 2-(trifluoromethyl)-benzyl bromide (0.05 ml, 0.328 mmol) was added. The reaction was brought to room temperature and stirred for 3 h followed by the addition of 1N HCl. The reaction was diluted with $H_2O$ and EtOAc and the layers separated. The aqueous layer was backextracted with EtOAc several times. The combined organic layers were washed with Brine, dried ($MgSO_4$), filtered and concentrated. The product was purified by column chromatography ($SiO_2$, 30-70% EtOAc/Hexanes) to give the title compound (99 mg, 65%). 1H NMR (400 MHz, DMSO-$d_6$) δ ppm 7.79 (d, J=7.58 Hz, 1H) 7.65 (t, J=7.58 Hz, 1H) 7.53 (t, J=7.58 Hz, 1H) 7.39-7.46 (m, 2H) 7.36 (tt, J=9.25, 2.37 Hz, 1H) 7.23 (d, J=7.83 Hz, 1 H) 5.45 (s, 2H) 4.30 (q, J=7.07 Hz, 2H) 1.28 (t, J=7.07 Hz, 3H).

73b) N-[(6-(3,5-Difluorophenyl)-5-hydroxy-3-oxo-2-{[2-(trifluoromethyl)phenyl]methyl}-2,3-dihydro-4-pyridazinyl)carbonyl]glycine. Glycine, sodium salt (40 mg, 0.412 mmol) was added to a solution of the compound from example 73a) (94 mg, 0.207 mmol) in 2-methoxyethanol (1.5 ml) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by recrystallization from hot $CH_2Cl_2$ to give the title compound as a white solid (39 mg, 39%). 1H NMR (400 MHz, DMSO-$d_6$) δ ppm 13.03 (s, 1H) 10.07-10.18 (m, 1H) 7.81 (d, J=7.58 Hz, 1H) 7.64 (t J=7.45 Hz, 1H) 7.47-7.59 (m, 3H) 7.41 (tt, J=9.32, 2.31 Hz, 1 H) 7.29 (d, J=7.83 Hz, 1H) 5.57 (s, 2H) 4.12 (d, J=5.81 Hz, 2H).

Example 74

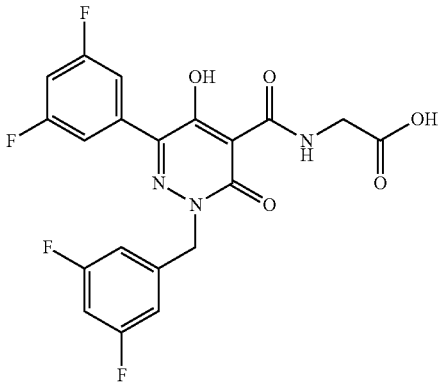

N-({6-(3,5-Difluorophenyl)-2-[(3,5-difluorophenyl)methyl]-5-hydroxy-3-oxo-2,3-dihydro-4-pyridazinyl}carbonyl)glycine 74a) Ethyl 6-(3,5-difluorophenyl)-2-[(3,5-difluorophenyl)methyl]-5-hydroxy-3-oxo-2,3-dihydro-4-pyridazinecarboxylate. Sodium hydride (34 mg, 0.850 mmol) was added to a solution of the compound from example 30b) (100 mg, 0.338 mmol) in N,N-Dimethylformamide (DMF) (2 ml) at 0° C. The reaction was brought to room temperature and stirred for 40 minutes. The temperature was then reduced to 0° C. and 3,5-difluorobenzyl bromide (0.044 ml, 0.338 mmol) was added. The reaction was brought to room temperature and stirred for 3 h followed by addition of 1N HCl. The solution was diluted with $H_2O$ and EtOAc and the layers separated. The aqueous layer was backextracted with EtOAc several times. The combined organic layers were washed with Brine, dried ($MgSO_4$), filtered and concentrated. The crude product was purified by column chromatography ($SiO_2$, 30-70% EtOAc/Hexanes) to give the title compound (98 mg, 69%). 1H NMR (400 MHz, DMSO-$d_6$) δ ppm 7.42-7.51 (m, 2H) 7.37 (tt, J=9.32, 2.31 Hz, 1H) 7.19 (tt, J=9.47, 2.40 Hz, 1H) 7.01-7.11 (m, J=14.91, 6.57, 2.27 Hz, 2H) 5.28 (s, 2H) 4.29 (q, J=7.07 Hz, 2H) 1.28 (t, J=7.07 Hz, 3H).

74b) N-({6-(3,5-Difluorophenyl)-2-[(3,5-difluorophenyl)methyl]-5-hydroxy-3-oxo-2,3-dihydro-4-pyridazinyl}carbonyl)glycine. Glycine, sodium salt (45 mg, 0.464 mmol) was added to a solution of the compound from example 74a) (98 mg, 0.232 mmol) in 2-methoxyethanol (1.5 ml) at room temperature. The reaction was heated to reflux and stirred for 2 h. The reaction was cooled back to room temperature and $H_2O$ was added. The solution was filtered and 1N HCl was added to precipitate the product. The solid was filtered and washed with $H_2O$ and Hexanes. The product was purified by recrystallization from hot $CH_2Cl_2$ to give the title compound as a white solid (53 mg, 51%). 1H NMR (400 MHz, DMSO-$d_6$) δ ppm 13.01 (s, 1H) 10.15 (t, J=5.18 Hz, 1

H) 7.50-7.62 (m, 2H) 7.41 (tt, J=9.25, 2.37 Hz, 1H) 7.19 (tt, J=9.47, 2.27 Hz, 1 H) 7.05-7.15 (m, 2H) 5.39 (s, 2H) 4.13 (d, J=5.56 Hz, 2H).

Example 75

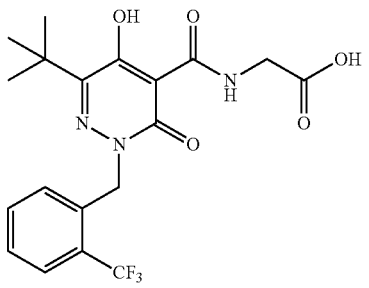

N-[(6-(1,1-Dimethylethyl)-5-hydroxy-3-oxo-2-{[2-(trifluoromethyl)phenyl]methyl}-2,3-dihydro-4-pyridazinyl)carbonyl]glycine 75a) Ethyl 6-(1,1-dimethylethyl)-5-hydroxy-3-oxo-2-{[2-(trifluoromethyl)phenyl]methyl}-2,3-dihydro-4-pyridazinecarboxylate. Sodium hydride (41.6 mg, 1.041 mmol) was added to a solution of the compound from example 45c) (100 mg, 0.416 mmol) in N,N-Dimethylformamide (DMF) (2 ml) at 0° C. The reaction was brought to room temperature and stirred for 1 h. The temperature was then reduced to 0° C. and 2-(trifluoromethyl)-benzyl bromide (99 mg, 0.416 mmol) was added. The reaction was brought to room temperature and stirred for 3 h followed by addition of 1N HCl. The solution was diluted with $H_2O$ and EtOAc and the layers separated. The aqueous layer was backextracted with EtOAc several times. The combined organic layers were washed with Brine, dried ($MgSO_4$), filtered and concentrated. The product was purified by column chromatography ($SiO_2$, 10-25% EtOAc/Hexanes) to give the title compound as a colorless oil (129 mg, 78%). 1H NMR (400 MHz, DMSO-$d_6$) δ ppm 12.72 (s, 1H) 7.77 (d, J=7.83 Hz, 1H) 7.65 (t, J=7.45 Hz, 1 H) 7.52 (t, J=7.58 Hz, 1H) 7.17 (d, J=7.58 Hz, 1H) 5.33 (s, 2H) 4.29 (q, J=7.16 Hz, 2H) 1.20-1.32 (m, 12H).

75b) N-[(6-(1,1-Dimethylethyl)-5-hydroxy-3-oxo-2-{[2-(trifluoromethyl)phenyl]methyl}-2,3-dihydro-4-pyridazinyl)carbonyl]glycine. Glycine, sodium salt (61 mg, 0.629 mmol) was added to a solution of the compound from example 75a) (125 mg, 0.314 mmol) in 2-methoxyethanol (2 ml) at room temperature. The reaction was heated to reflux and stirred for 2 h. The reaction was cooled back to room temperature and $H_2O$ was added. The solution was filtered and 1N HCl was added to precipitate the product as a tan gum. The gum was filtered and washed with $H_2O$ and Hexanes. The product was purified by recrystallization from hot $CH_2Cl_2$ to give the title compound as a white solid (103 mg, 77%). 1H NMR (400 MHz, DMSO-$d_6$) δ ppm 12.98 (s, 1H) 10.23 (t, J=5.31 Hz, 1H) 7.79 (d, J=7.83 Hz, 1H) 7.64 (t, J=7.33 Hz, 1H) 7.53 (t J=7.58 Hz, 1H) 7.21 (d, J=7.83 Hz, 1H) 5.43 (s, 2H) 4.10 (d, J=5.81 Hz, 2H) 1.28 (s, 9 H).

Example 76

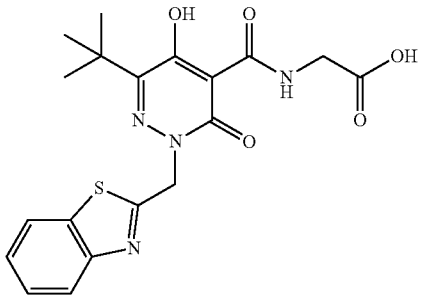

N-{[2-(1,3-Benzothiazol-2-ylmethyl)-5-hydroxy-6-(1-methylethyl)-3-oxo-2,3-dihydro-4-pyridazinyl]carbonyl}glycine 76a) Ethyl 2-(1,3-benzothiazol-2-ylmethyl)-5-hydroxy-6-(1-methylethyl)-3-oxo-2,3-dihydro-4-pyridazinecarboxylate. Sodium hydride (53 mg, 1.326 mmol) was added to a solution of the compound from example 14a) (120 mg, 0.530 mmol) in N,N-Dimethylformamide (DMF) (3 ml) at 0° C. The reaction was brought to room temperature and stirred for 40 minutes. The temperature was then reduced to 0° C. and 2-(bromomethyl)-1,3-benzothiazole (112 mg, 0.491 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 35-60% EtOAc/Hexanes) to give the title compound as an orange oil (61 mg, 0.163 mmol, 31%). 1H NMR (400 MHz, DMSO-$d_6$) δ ppm 12.48 (s, 1H) 8.05-8.11 (m, 1H) 7.97-8.02 (m, 1H) 7.52 (ddd, J=8.21, 7.20, 1.26 Hz, 1H) 7.44 (td, J=7.58, 1.26 Hz, 1H) 5.59 (s, 2H) 4.27 (q, J=7.07 Hz, 2H) 3.20 (sept, J=6.82 Hz, 1H) 1.26 (t, J=7.20 Hz, 3H) 1.19 (d, J=6.82 Hz, 6H).

76b) N-{[2-(1,3-Benzothiazol-2-ylmethyl)-5-hydroxy-6-(1-methylethyl)-3-oxo-2,3-dihydro-4-pyridazinyl]carbonyl}glycine. Glycine, sodium salt (29 mg, 0.299 mmol) was added to a solution of the compound from example 76a) (56 mg, 0.150 mmol) in 2-methoxyethanol (2.5 ml) at room temperature. The reaction was heated to reflux and stirred for 2 h. The reaction was cooled to room temperature and $H_2O$ was added. The solution was filtered and 1N HCl added to precipitate the product. The solid was filtered and washed with $H_2O$ and Hexanes. The product was purified by precipitation from $CH_2Cl_2$/Hexanes to give the title compound as a pale yellow solid (41 mg, 68%). 1H NMR (400 MHz, DMSO-$d_6$) d ppm 1.22 (d, J=6.82 Hz, 6H) 3.14-3.29 (m, 1 H) 4.10 (d, J=5.56 Hz, 2H) 5.70 (s, 2H) 7.41-7.48 (m, 1H) 7.48-7.56 (m, 1H) 7.96-8.04 (m, 1H) 8.06-8.12 (m, 1H) 10.07 (t, J=5.43 Hz, 1H) 12.99 (s, 1H) 16.06 (s, 1H).

Example 77

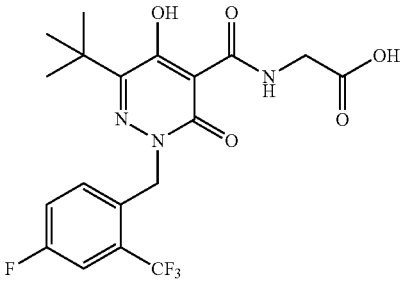

N-[(6-(1,1-Dimethylethyl)-2-{[4-fluoro-2-(trifluoromethyl)phenyl]methyl}-5-hydroxy-3-oxo-2,3-dihydro-4-pyridazinyl)carbonyl]glycine 77a) Ethyl 6-(1,1-dimethylethyl)-2-{[4-fluoro-2-(trifluoromethyl)phenyl]methyl}-5-hydroxy-3-oxo-2,3-dihydro-4-pyridazinecarboxylate. Sodium hydride (46 mg, 1.150 mmol) was added to a solution of the compound from example 45c) (110 mg, 0.458 mmol) in N,N-Dimethylformamide (DMF) (2.5 ml) at 0° C. The reaction was brought to room temperature and stirred for 40 minutes. The temperature was then reduced to 0° C. and 4-fluoro-2-(trifluoromethyl)-benzyl bromide (118 mg, 0.458 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 25-50% EtOAc/Hexanes) to give the title compound as a colorless oil (136 mg, 71%). 1H NMR (400 MHz, DMSO-$d_6$) δ ppm 12.71 (s, 1H) 7.68 (dd, J=9.35, 2.78 Hz, 1H) 7.54 (td, J=8.53, 2.65 Hz, 1H) 7.30 (dd, J=8.72, 5.43 Hz, 1H) 5.29 (s, 2H) 4.29 (q, J=7.07 Hz, 2H) 1.27 (t, J=7.07 Hz, 3H) 1.24 (s, 9H).

77b) N-[(6-(1,1-dimethylethyl)-2-{[4-fluoro-2-(trifluoromethyl)phenyl]methyl}-5-hydroxy-3-oxo-2,3-dihydro-4-pyridazinyl)carbonyl]glycine. Glycine, sodium salt (27 mg, 0.365 mmol) was added to a solution of the compound from example 77a) (75 mg, 0.180 mmol) in 2-methoxyethanol (2 ml) at room temperature. The reaction was heated to reflux and stirred for 2 h. The reaction was then cooled to room temperature and $H_2O$ added. The solution was filtered and 1N HCl added to precipitate the product. The solid was filtered then redissolved in a 1N NaOH solution in MeOH/THF. After stirring for 1 h at room temperature, the solvent was removed under reduced pressure and $H_2O$ was added. 1N HCl was added to precipitate the product, which was filtered as a tan gum. The gum was dissolved in hot $CH_2Cl_2$ and the solution concentrated to give the title compound as an off-white solid (60 mg, 75%). 1H NMR (400 MHz, DMSO-$d_6$) δ ppm 10.23 (t, J=5.31 Hz, 1H) 7.69 (dd, J=9.09, 2.78 Hz, 1H) 7.53 (td, J=8.46, 2.78 Hz, 1H) 7.34 (dd, J=8.59, 5.31 Hz, 1H) 5.39 (s, 2H) 4.09 (d, J=5.81 Hz, 2H) 1.26 (s, 9H).

Example 78

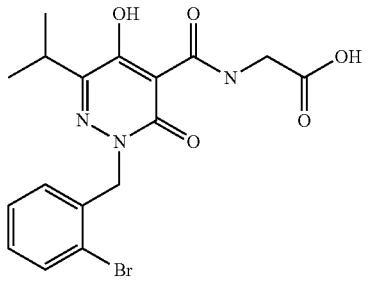

N-{[2-[(2-Bromophenyl)methyl]-5-hydroxy-6-(1-methylethyl)-3-oxo-2,3-dihydro-4-pyridazinyl]carbonyl}glycine 78a) Ethyl 2-[(2-bromophenyl)methyl]-5-hydroxy-6-(1-methylethyl)-3-oxo-2,3-dihydro-4-pyridazinecarboxylate. To a solution of ethyl 5-hydroxy-6-(1-methylethyl)-3-oxo-2,3-dihydro-4-pyridazinecarboxylate (example 46(a), 3 g, 13.26 mmol) in N,N-Dimethylformamide (DMF) (50 ml) at 0° C. was added sodium hydride (0.796 g, 19.89 mmol) in portions. The reaction mixture was stirred at room temperature for 45 minutes and then cooled back to 0° C. and 2-bromobenzylbromide (3.31 g, 13.26) was added portionwise. The mixture was stirred at ambient temperature for 2.5 hours then quenched with 1N HCl (10 ml) and diluted with water (30 ml). The aqueous solution was extracted with ethyl acetate (2×100 ml), the organic layers combined and washed with water (100 ml) and brine (100 ml), dried over Magnesium sulfate, filtered and solvents removed with rotary evaporation. The crude solid was triturated with ether and filtered. The solid material was 100% starting material (1 g). The filtrate was purified by flash column chromatography (10-100% ethyl acetate in hexanes) to provide the title compound (ethyl 2-[(2-bromophenyl)methyl]-5-hydroxy-6-(1-methylethyl)-3-oxo-2,3-dihydro-4-pyridazinecarboxylate (1.3 g, 2.96 mmol, 22.32% yield) as a pale yellow solid. 1H NMR (400 MHz, DMSO-$d_6$) d ppm 12.33 (br. s., 1H), 7.66 (dd, J=8.08, 1.26 Hz, 1H), 7.35 (td, J=7.52, 1.14 Hz, 1H), 7.25 (td, J=7.58, 1.77 Hz, 1H), 7.03 (dd, J=7.83, 1.52 Hz, 1H), 5.20 (s, 2H), 4.28 (q, J=7.07 Hz, 2H), 3.15 (sept, J=6.82 Hz, 1H), 1.26 (t, J=7.07 Hz, 3H), 1.11 (d, J=6.82 Hz, 6 H). MS (ES+) m/e 396 [M+H]+.

78b) N-{[2-[(2-Bromophenyl)methyl]-5-hydroxy-6-(1-methylethyl)-3-oxo-2,3-dihydro-4-pyridazinyl]carbonyl}glycine. To a 20 mL microwave tube was added ethyl 2-[(2-bromophenyl)methyl]-5-hydroxy-6-(1-methylethyl)-3-oxo-2,3-dihydro-4-pyridazinecarboxylate (1.2 g, 3.04 mmol) and Glycine Sodium Salt (0.589 g, 6.07 mmol) in 2-methoxyethanol (8 ml) and the mixture was irradiated at 150° C. for 20 minutes. The reaction mixture was diluted with water (10 ml) and acidified with 1N HCl to give a off-white precipitate that was collected by filtration and washed with water, hexanes and ether to give N-{[2-[(2-bromophenyl)methyl]-5-hydroxy-6-(1-methylethyl)-3-oxo-2,3-dihydro-4-pyridazinyl]carbonyl}glycine (1.06 g, 2.499 mmol, 82% yield). 1H NMR (400 MHz, DMSO-$d_6$) d ppm 15.94 (s, 1H), 12.99 (s, 1H), 10.15 (t, J=5.43 Hz, 1H), 7.67 (dd, J=7.83, 1.26

Hz, 1H), 7.35 (td, J=7.52, 1.14 Hz, 1H), 7.26 (td, J=7.58, 1.77 Hz, 1 H), 7.08 (dd, J=7.71, 1.64 Hz, 1H), 5.31 (s, 2H), 4.10 (d, J=5.81 Hz, 2H), 3.17 (sept, J=6.82 Hz, 1H), 1.14 (d, J=6.82 Hz, 6H). MS (ES+) m/e 425 [M+H]+.

Example 79

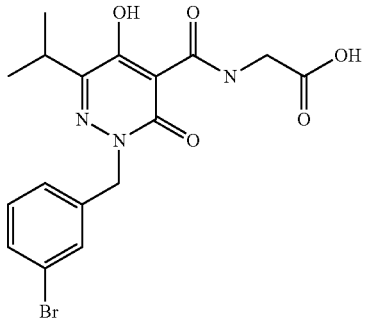

N-{[2-[(3-Bromophenyl)methyl]-5-hydroxy-6-(1-methylethyl)-3-oxo-2,3-dihydro-4-pyridazinyl]carbonyl}glycine 79a) Ethyl 2-[(3-bromophenyl)methyl]-5-hydroxy-6-(1-methylethyl)-3-oxo-2,3-dihydro-4-pyridazinecarboxylate. To a solution of ethyl 5-hydroxy-6-(1-methylethyl)-3-oxo-2,3-dihydro-4-pyridazinecarboxylate (example 46(a), 3 g, 13.26 mmol) in N,N-Dimethylformamide (DMF) (50 ml) at 0° C. was added sodium hydride (0.796 g, 19.89 mmol) in portions. The reaction mixture was stirred at room temperature for 45 minutes and then cooled back to 0° C. and 3-bromobenzyl bromide (3.31 g, 13.26 mmol) was added portionwise. The mixture was stirred at ambient temperature for 2.5 hours then quenched with 1N HCl (10 ml) and diluted with water (30 ml). The aqueous solution was extracted with ethyl acetate (2×100 ml), the organic layers combined and washed with water (100 ml) and brine (100 ml), dried over Magnesium sulfate, filtered and solvents removed with rotary evaporation. The crude oil was purified by flash column chromatography (10-100% ethyl acetate in hexanes) to provide the title compound (ethyl 2-[(3-bromophenyl)methyl]-5-hydroxy-6-(1-methylethyl)-3-oxo-2,3-dihydro-4-pyridazinecarboxylate (890 mg, 1.801 mmol, 13.58% yield) as a pale yellow solid. The product isolated was a 5:1 mixture of the desired mono alkylated to the bis-alkylated(4-O-benzyl) (LCMS=564). 1H NMR (400 MHz, DMSO-$d_6$) d ppm 12.33 (s, 1H), 7.46-7.53 (m, 2H), 7.24-7.35 (m, 2H), 5.14 (s, 2 H), 4.26 (q, J=7.07 Hz, 2H), 3.17 (sept, J=6.78 Hz, 1H), 1.26 (t, J=7.20 Hz, 3H), 1.16 (d, J=6.82 Hz, 6H). MS (ES+) m/e 396 [M+H]+.

79b) N-{[2-[(3-Bromophenyl)methyl]-5-hydroxy-6-(1-methylethyl)-3-oxo-2,3-dihydro-4-pyridazinyl]carbonyl}glycine. To a 20 mL microwave tube was added ethyl 2-[(3-bromophenyl)methyl]-5-hydroxy-6-(1-methylethyl)-3-oxo-2,3-dihydro-4-pyridazinecarboxylate (700 mg, 1.771 mmol) and Glycine Sodium Salt (172 mg, 1.771 mmol) in MethoxyEthanol (8 ml) and the mixture was irradiated at 150° C. for 20 minutes. The reaction mixture was diluted with water (10 ml) and acidified with 1N HCl to give a off-white precipitate that was collected by filtration and washed with water, hexanes and ether to give N-{[2-[(3-bromophenyl)methyl]-5-hydroxy-6-(1-methylethyl)-3-oxo-2,3-dihydro-4-pyridazinyl]carbonyl}glycine (270 mg, 0.636 mmol, 35.9% yield). 1H NMR (400 MHz, DMSO-$d_6$) d ppm 15.91 (s, 1H), 12.98 (s, 1H), 10.15 (t, J=5.43 Hz, 1H), 7.53 (t, J=1.52 Hz, 1H), 7.50 (dt, J=7.58, 1.77 Hz, 1H), 7.32 (t, J=7.71 Hz, 1 H), 7.28 (ddd, J=7.71, 1.39, 1.26 Hz, 1H), 5.25 (s, 2H), 4.10 (d, J=5.56 Hz, 2H), 3.19 (sept, J=6.78 Hz, 1H), 1.20 (d, J=7.07 Hz, 6H). MS (ES+) m/e 425 [M+H]+.

Example 80

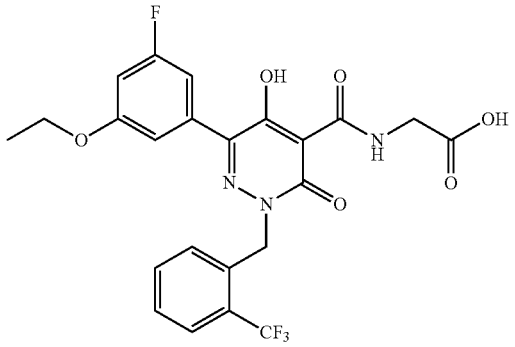

N-[(6-[3-(Ethyloxy)-5-fluorophenyl]-5-hydroxy-3-oxo-2-{[2-(trifluoromethyl)phenyl]methyl}-2,3-dihydro-4-pyridazinyl)carbonyl]glycine 80a) Ethyl 6-[3-(ethyloxy)-5-fluorophenyl]-5-hydroxy-3-oxo-2-{[2-(trifluoromethyl)phenyl]methyl}-2,3-dihydro-4-pyridazinecarboxylate. Sodium hydride (24 mg, 0.600 mmol) was added to a solution of the compound from example 69a) (78 mg, 0.242 mmol) in N,N-Dimethylformamide (DMF) (2 ml) at 0° C. The reaction was brought to room temperature and stirred for 40 minutes. The temperature was then reduced to 0° C. and 2-(trifluoromethyl)-benzyl bromide (58 mg, 0.243 mmol) was added. The reaction was brought to room temperature and stirred for 3 h followed by addition of 1N HCl. The reaction was diluted with $H_2O$ and EtOAc and the layers separated. The aqueous phase was backextracted with EtOAc several times. The combined organic layers were washed with Brine, dried ($MgSO_4$), filtered and concentrated. The product was purified by column chromatography ($SiO_2$, 25-50% EtOAc/Hexanes) to give the title compound (104 mg, 89%). 1H NMR (400 MHz, DMSO-$d_6$) δ ppm 7.79 (d, J=7.58 Hz, 1H) 7.65 (t, J=7.45 Hz, 1H) 7.53 (t, J=7.71 Hz, 1H) 7.22 (d, J=7.83 Hz, 1H) 7.03-7.10 (m, 2H) 6.91 (dt, J=10.86, 2.27 Hz, 1H) 5.44 (s, 2H) 4.30 (q, J=7.16 Hz, 2H) 4.04 (q, J=6.99 Hz, 2H) 1.32 (t, J=6.95 Hz, 3H) 1.28 (t, J=7.07 Hz, 3H).

80b) N-[(6-[3-(Ethyloxy)-5-fluorophenyl]-5-hydroxy-3-oxo-2-{[2-(trifluoromethyl)phenyl]methyl}-2,3-dihydro-4-pyridazinyl)carbonyl]glycine. Glycine, sodium salt (41 mg, 0.422 mmol) was added to a solution of the compound from example 80a) (101 mg, 0.210 mmol) in 2-methoxyethanol (2 ml) at room temperature. The reaction was heated to reflux and stirred for 2 h. The reaction was cooled back to room temperature and $H_2O$ was added followed by 1N HCl to precipitate the product. The solid was filtered and washed with $H_2O$ and Hexanes. The product was purified by recrystallization from hot EtOH to give the title compound as a white solid (77 mg, 72%). 1H NMR (400 MHz, DMSO-$d_6$) δ ppm 13.01 (s, 1H) 10.15 (t, J=5.18 Hz, 1H) 7.81 (d, J=7.58 Hz, 1H) 7.64 (t, J=7.45 Hz, 1H) 7.54 (t, J=7.58 Hz, 1H) 7.29 (d, J=7.83 Hz, 1H) 7.12-7.19 (m, 2H) 6.95 (dt, J=10.93, 2.37 Hz, 1H) 5.56 (s, 2H) 4.13 (d, J=5.81 Hz, 2H) 4.05 (q, J=6.91 Hz, 2H) 1.33 (t, J=6.95 Hz, 3H).

Example 81

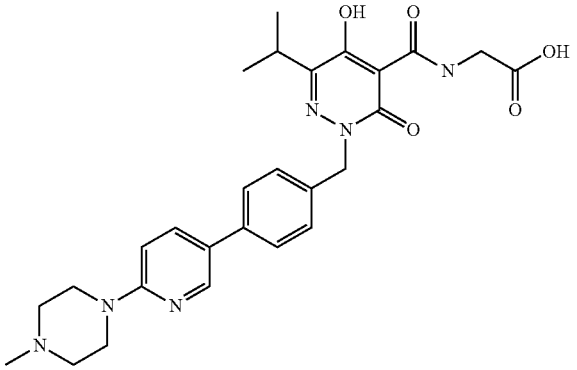

N-{[5-Hydroxy-6-(1 -methylethyl)-2-({4-[6-(4-methyl-1-piperazinyl)-3-pyridinyl]phenyl}methyl)-3-oxo-2,3-dihydro-4-pyridazinyl]carbonyl}glycine To a 5 mL microwave tube was added N-{[2-[(4-bromophenyl)methyl]-5-hydroxy-6-(1-methylethyl)-3-oxo-2,3-dihydro-4-pyridazinyl]carbonyl}glycine (example 61, 31 mg, 0.073 mmol), 1-methyl-4-[5-(4,4,5,5-tetramethyl-1,3,2-dioxaborolan-2-yl)-2-pyridinyl]piperazine (22.16 mg, 0.073 mmol), potassium carbonate (30.3 mg, 0.219 mmol), and tetrakis(triphenylphosphine)palladium (0) (2.53 mg, 2.192 μmol) in 1,4-Dioxane (1.5 ml) and Water (0.500 ml). The mixture was irradiated at 100° C. for 20 minutes. The reaction mixture was diluted with water (4 ml) and acidified with 1N HCl (1 ml) then filtered to remove any residue followed by purification by HPLC chromatography (ODS silica, gradient 10-75% acetonitrile/water (0.1% TFA)) to afford the title compound N-{[5-hydroxy-6-(1-methylethyl)-2-({4-[6-(4-methyl-1-piperazinyl)-3-pyridinyl]phenyl}methyl)-3-oxo-2,3-dihydro-4-pyridazinyl]carbonyl}glycine (23 mg, 0.036 mmol, 49.7% yield) as a white powder tfa salt. 1H NMR (400 MHz, DMSO-$d_6$) d ppm 15.87 (s, 1H), 10.19 (t, J=5.68 Hz, 1H), 9.94 (s, 1 H), 8.48 (d, J=2.53 Hz, 1H), 7.94 (dd, J=9.09, 2.53 Hz, 1H), 7.62 (d, J=8.34 Hz, 2H), 7.38 (d, J=8.34 Hz, 2 H), 7.06 (d, J=9.09 Hz, 1H), 5.28 (s, 2H), 4.47 (d, J=13.39 Hz, 2H), 4.10 (d, J=5.56 Hz, 2H), 3.53 (dd, J=10.23, 6.44 Hz, 2H), 2.99-3.26 (m, 5H), 2.85 (s, 3H), 1.22 (d, J=6.82 Hz, 6H). MS (ES+) m/e 521 [M+H]+.

Example 82

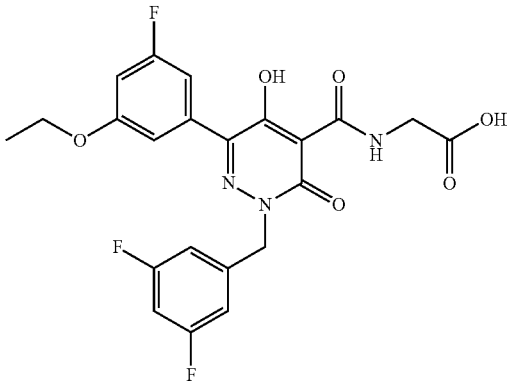

N-({2-[(3,5-Difluorophenyl)methyl]-6-[3-(ethyloxy)-5-fluorophenyl]-5-hydroxy-3-oxo-2,3-dihydro-4-pyridazinyl}carbonyl)glycine 82a) Ethyl 2-[(3,5-difluorophenyl)methyl]-6-[3-(ethyloxy)-5-fluorophenyl]-5-hydroxy-3-oxo-2,3-dihydro-4-pyridazinecarboxylate. Sodium hydride (23 mg, 0.575 mmol) was added to a solution of the compound from example 69a) (75 mg, 0.233 mmol) in N,N-Dimethylformamide (DMF) (2 ml) at 0° C. The reaction was brought to room temperature and stirred for 40 minutes. The temperature was then reduced to 0° C. and 3,5-difluorobenzylbromide (0.030 ml, 0.232 mmol) was added. After stirring for 3 h at room temperature, $H_2O$ was added followed by 1N HCl to precipitate the product. The solid was filtered and purified by column chromatography ($SiO_2$, 25-50% EtOAc/Hexanes) to give the title compound as a white solid (66 mg, 63%). 1H NMR (400 MHz, DMSO-$d_6$) δ ppm 7.19 (tt, J=9.44, 2.31 Hz, 1H) 7.00-7.13 (m, 4H) 6.93 (dt, J=11.12, 2.27 Hz, 1H) 5.27 (s, 2H) 4.30 (q, J=7.07 Hz, 2H) 4.07 (q, J=6.99 Hz, 2H) 1.34 (t, J=7.07 Hz, 3H) 1.28 (t, J=7.20 Hz, 3H).

82b) N-({2-[(3,5-Difluorophenyl)methyl]-6-[3-(ethyloxy)-5-fluorophenyl]-5-hydroxy-3-oxo-2,3-dihydro-4-pyridazinyl}carbonyl)glycine. Glycine, sodium salt (27 mg, 0.278 mmol) was added to a solution of the compound from example 82a) (63 mg, 0.141 mmol) in 2-methoxyethanol (1.5 ml) at room temperature. The reaction was heated to reflux and stirred for 2 h. The reaction was cooled back to room temperature and $H_2O$ was added followed by 1N HCl to precipitate the product. The solid was filtered and washed with $H_2O$ and Hexanes. The product was purified by recrystallization from hot EtOH to give the title compound as a white solid (15 mg, 22%). 1H NMR (400 MHz, DMSO-$d_6$) δ ppm 13.01 (s, 1H) 10.16 (t, J=5.31 Hz, 1H) 7.15-7.24 (m, 3H) 7.05-7.14 (m, 2H) 6.97 (dt, J=11.05, 2.31 Hz, 1H) 5.39 (s, 2H) 4.13 (d, J=5.81 Hz, 2H) 4.08 (q, J=7.07 Hz, 2H) 1.34 (t, J=6.95 Hz, 3H).

Example 83

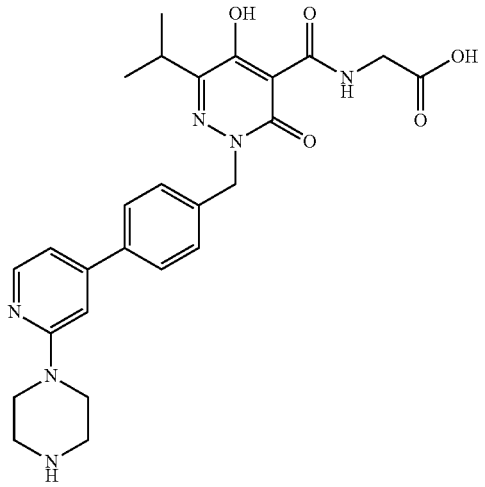

N-{[5-Hydroxy-6-(1 -methylethyl)-3-oxo-2-({4-[2-(1 -piperazinyl)-4-pyridinyl]phenyl}methyl)-2,3-dihydro-4-pyridazinyl]carbonyl}glycine To a 5 mL microwave tube was added N-{[2-[(4-bromophenyl)methyl]-5-hydroxy-6-(1-methylethyl)-3-oxo-2,3-dihydro-4-pyridazinyl]carbonyl}glycine (example 61, 31 mg, 0.073 mmol), 1-[4-(4,4,5,5-tetramethyl-1,3,2-dioxaborolan-2-yl)-2-pyridinyl]piperazine (21.13 mg, 0.073 mmol), potassium carbonate (30.3 mg, 0.219 mmol), and tetrakis(triphenylphosphine)palladium (0) (2.53 mg, 2.192 μmol) in 1,4-Dioxane (1.5 ml) and Water (0.500 ml). The mixture was irradiated at 100° C. for 20 minutes. The reaction mixture was diluted with water (10 ml) and acidified with 1N HCl. The mixture was then extracted with ethyl acetate (2×50 mL) and the organic layers combined, dried over magnesium sulfate, filtered, and solvents removed by rotary evaporation. The mixture of products, by tlc, was purified by HPLC chromatography (ODS silica, gradient 10-100% acetonitrile/water (0.1% TFA)). However, the product was not there but found in the aqueous extract, 100% clean, which was evaporated to afford the title compound N-{[5-hydroxy-6-(1-methylethyl)-3-oxo-2-({4-[2-(1-piperazinyl)-4-pyridinyl]phenyl}methyl)-2,3-dihydro-4-pyridazinyl]carbonyl}glycine (26 mg, 0.049 mmol, 66.7% yield) as a tfa salt. 1H NMR (400 MHz, DMSO-$d_6$) d ppm 15.89 (s, 1H), 10.18 (t, J=5.81 Hz, 1H), 8.80 (br. s., 2H), 8.21 (d, J=5.56 Hz, 1H), 7.78 (d, J=8.34 Hz, 2H), 7.43 (d, J=8.34 Hz, 2H), 7.23 (s, 1H), 7.09 (dd, J=5.31, 1.01 Hz, 1H), 5.32 (s, 2H), 4.11 (d, J=5.81 Hz, 2H), 3.76-3.87 (m, 4H), 3.13-3.29 (m, 5H), 1.22 (d, J=7.07 Hz, 6H). MS (ES+) m/e 507 [M+H]+.

Example 84

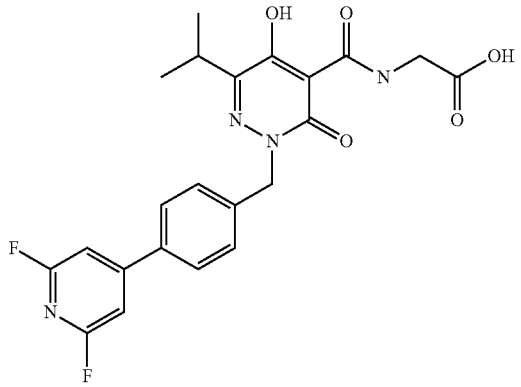

N-{[2-{[4-(2,6-Difluoro-4-pyridinyl)phenyl]methyl}-5-hydroxy-6-(1-methylethyl)-3-oxo-2,3-dihydro-4-pyridazinyl]carbonyl}glycine To a 5 mL microwave tube was added N-{[2-[(4-bromophenyl)methyl]-5-hydroxy-6-(1-methylethyl)-3-oxo-2,3-dihydro-4-pyridazinyl]carbonyl}glycine (example 61, 31 mg, 0.073 mmol), 2,6-difluoropyridine-4-boronic acid (11.61 mg, 0.073 mmol), potassium carbonate (30.3 mg, 0.219 mmol), and tetrakis(triphenylphosphine)palladium (0) (2.53 mg, 2.192 μmol) in 1,4-Dioxane (1.5 ml) and Water (0.500 ml). The mixture was irradiated at 100° C. for 20 minutes. The reaction mixture was diluted with water (4 ml), acidified with 1N HCl (1 ml), and diluted with methanol (2 ml) then filtered to remove any residue followed by purification by HPLC chromatography (ODS silica, gradient 10-75% acetonitrile/water (0.1% TFA)) to afford the title compound N-{[2-{[4-(2,6-difluoro-4-pyridinyl)phenyl]methyl}-5-hydroxy-6-(1-methylethyl)-3-oxo-2,3-dihydro-4-pyridazinyl]carbonyl}glycine (15 mg, 0.033 mmol, 44.8% yield) as a white powder. 1H NMR (400 MHz, DMSO-$d_6$) d ppm 15.91 (s, 1H), 12.98 (s, 1H), 10.17 (t, J=5.56 Hz, 1H), 7.89 (d, J=8.34 Hz, 2H), 7.57 (s, 2H), 7.45 (d, J=8.34 Hz, 2H), 5.33 (s, 2H), 4.10 (d, J=5.56 Hz, 2H), 3.20 (sept, J=6.82 Hz, 1H), 1.21 (d, J=6.82 Hz, 6H). MS (ES+) m/e 459 [M+H]+.

Example 85

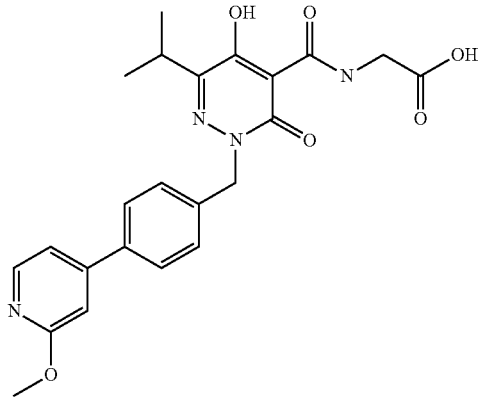

N-{[5-Hydroxy-6-(1-methylethyl)-2-({4-[2-(methyloxy)-4-pyridinyl]phenyl}methyl)-3-oxo-2,3-dihydro-4-pyridazinyl]carbonyl}glycine To a 20 mL microwave tube was added N-{[2-[(4-bromophenyl)methyl]-5-hydroxy-6-(1-methylethyl)-3-oxo-2,3-dihydro-4-pyridazinyl]carbonyl}glycine (example 61, 31 mg, 0.073 mmol), [2-(methyloxy)-4-pyridinyl]boronic acid (11.18 mg, 0.073 mmol), potassium carbonate (30.3 mg, 0.219 mmol), and tetrakis(triphenylphosphine)palladium (0) (2.53 mg, 2.192 μmol) in 1,4-Dioxane (1.5 ml) and Water (0.500 ml). The mixture was irradiated at 100° C. for 20 minutes. The reaction mixture was diluted with water (4 ml) and acidified with 1N HCl (1 ml) then filtered to remove any residue followed by purification by HPLC chromatography (ODS silica, gradient 10-75% acetonitrile/water (0.1% TFA)) to afford the title compound N-{[5-hydroxy-6-(1-methylethyl)-2-({4-[2-(methyloxy)-4-pyridinyl]phenyl}methyl)-3-oxo-2,3-dihydro-4-pyridazinyl]carbonyl}glycine (15 mg, 0.031 mmol, 43.1% yield). 1H NMR (400 MHz, DMSO-$d_6$) d ppm 15.89 (s, 1H), 12.96 (br. s., 1H), 10.18 (t, J=5.56 Hz, 1H), 8.22 (d, J=5.31 Hz, 1H), 7.76 (d, J=8.34 Hz, 2H), 7.42 (d, J=8.34 Hz, 2H), 7.30 (dd, J=5.43, 1.39 Hz, 1H), 7.10 (s, 1H), 5.31 (s, 2H), 4.10 (d, J=5.81 Hz, 2H), 3.89 (s, 3H), 3.19 (sept, J=6.78 Hz, 1H), 1.21 (d, J=6.82 Hz, 6H). MS (ES+) m/e 453 [M+H]+.

Example 86

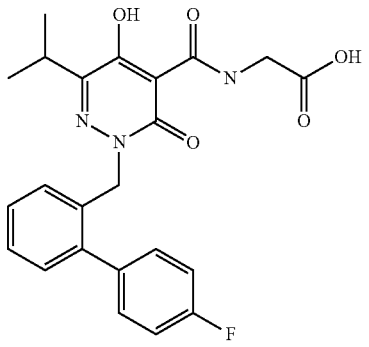

N-{[2-[(4'-Fluoro-2-biphenylyl)methyl]-5-hydroxy-6-(1-methylethyl)-3-oxo-2,3-dihydro-4-pyridazinyl]carbonyl}glycine To a 5 ml microwave tube was added N-{[2-[(2-bromophenyl)methyl]-5-hydroxy-6-(1-methylethyl)-3-oxo-2,3-dihydro-4-pyridazinyl]carbonyl}glycine (example 78(b), 75 mg, 0.177 mmol), 4-fluorobenzeneboronic acid (24.74 mg, 0.177 mmol), potassium carbonate (73.3 mg, 0.530 mmol), and tetrakis(triphenylphosphine)palladium (0) (6.13 mg, 5.30 μmol) in 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 10-75% acetonitrile/water (0.1% TFA)) to afford the title compound N-{[2-[(4'-fluoro-2-biphenylyl)methyl]-5-hydroxy-6-(1-methylethyl)-3-oxo-2,3-dihydro-4-pyridazinyl]carbonyl}glycine (42 mg, 0.095 mmol, 53.5% yield) as a white powder. 1H NMR (400 MHz, DMSO-$d_6$) δ ppm 15.83 (s, 1H), 12.95 (s, 1H), 10.08 (t, J=5.68 Hz, 1 H), 7.44 (ddd, J=11.94, 5.37, 2.91 Hz, 2H), 7.31-7.38 (m, 2H), 7.22-7.30 (m, 3H), 7.11-7.19 (m, 1H), 5.24 (s, 2H), 4.07 (d, J=5.81 Hz, 2H), 3.13 (sept, J=6.82 Hz, 1H), 1.12 (d, J=6.82 Hz, 6H). MS (ES+) m/e 440 [M+H]+.

Example 87

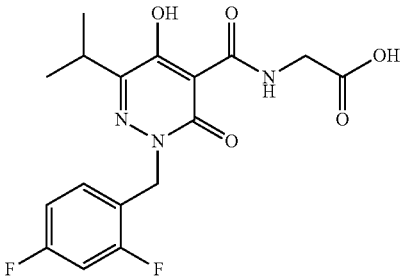

N-{[2-[(2,4-Difluorophenyl)methyl]-5-hydroxy-6-(1-methylethyl)-3-oxo-2,3-dihydro-4-pyridazinyl]carbonyl}glycine 87a) Ethyl 2-[(2,4-difluorophenyl)methyl]-5-hydroxy-6-(1-methylethyl)-3-oxo-2,3-dihydro-4-pyridazinecarboxylate. Sodium hydride (46 mg, 1.150 mmol) was added to a solution of the compound from example 14a) (105 mg, 0.464 mmol) in N,N-Dimethylformamide (DMF) (3 ml) at 0° C. The reaction was brought to room temperature and stirred for 40 minutes. The temperature was then reduced to 0° C. and 2,4-difluorobenzylbromide (0.06 ml, 0.468 mmol) was added. The reaction was brought to room temperature and stirred for 3 h followed by the addition of 1N HCl. The solution was diluted with EtOAc and $H_2O$ and the layers separated. The aqueous layer was backextracted with EtOAc several times. The combined organic layers were washed with Brine, dried ($MgSO_4$), filtered and concentrated. The product was purified by column chromatography ($SiO_2$, 15-35% EtOAc/Hexanes) to give the title compound as a white solid (132 mg, 81%). 1H NMR (400 MHz, DMSO-$d_6$) δ ppm 12.30 (s, 1H) 7.33 (td, J=8.59, 6.82 Hz, 1H) 7.26 (ddd, J=10.29, 9.54, 2.65 Hz, 1H) 7.03-7.11 (m, J=8.56, 8.56, 2.59, 1.01 Hz, 1H) 5.16 (s, 2 H) 4.26 (q, J=7.16 Hz, 2H) 3.14 (qq, J=6.95, 6.80 Hz, 1H) 1.26 (t, J=7.20 Hz, 3H) 1.12 (d, J=6.82 Hz, 6H).

87b) N-{[2-[(2,4-Difluorophenyl)methyl]-5-hydroxy-6-(1-methylethyl)-3-oxo-2,3-dihydro-4-pyridazinyl]carbonyl}glycine. Glycine, sodium salt (71 mg, 0.732 mmol) was added to a solution of the compound from example 87a) (128 mg, 0.363 mmol) in 2-methoxyethanol (2 ml) at room temperature. The reaction was heated to reflux and stirred for 2 h. The reaction was then cooled to room temperature and $H_2O$ added. The solution was filtered and 1N HCl was added to precipitate the product. The product was purified by recrystallization from hot EtOH to give the title compound as a white solid (61 mg, 44%). 1H NMR (400 MHz, DMSO-$d_6$) δ ppm 15.90 (s, 1H) 12.97 (s, 1H) 10.14 (t, J=5.56 Hz, 1H) 7.37 (td, J=8.53, 6.69 Hz, 1H) 7.27 (ddd, J=10.42, 9.41, 2.65 Hz, 1H) 7.02-7.12 (m, J=8.53, 8.53, 2.53, 0.88 Hz, 1H) 5.27 (s, 2H) 4.09 (d, J=5.81 Hz, 2 H) 3.17 (m, 1H) 1.16 (d, J=7.07 Hz, 6H).

Example 88

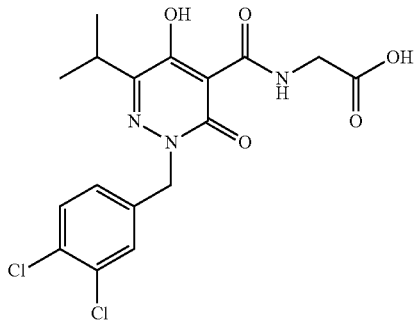

N-{[2-[(3,4-Dichlorophenyl)methyl]-5-hydroxy-6-(1-methylethyl)-3-oxo-2,3-dihydro-4-pyridazinyl]carbonyl}glycine 88a) Ethyl 2-[(3,4-dichlorophenyl)methyl]-5-hydroxy-6-(1-methylethyl)-3-oxo-2,3-dihydro-4-pyridazinecarboxylate. Sodium hydride (46 mg, 1.150 mmol) was added to a solution of the compound from example 14a) (105 mg, 0.464 mmol) in N,N-Dimethylformamide (DMF) (3 ml) at 0° C. The reaction was brought to room temperature and stirred for 40 minutes. The temperature was then reduced to 0° C. and 3,4-dichlorobenzyl bromide (0.07 ml, 0.481 mmol) was added. The reaction was brought to room temperature and stirred for 3 h followed by the addition of 1N HCl. The reaction was diluted with $H_2O$ and EtOAc and the layers separated. The aqueous phase was backextracted with EtOAc several times. The combined organic layers were washed with Brine, dried ($MgSO_4$), filtered and concentrated. The product was purified by column chromatography ($SiO_2$, 15-35% EtOAc/Hexanes) to give the title compound as a white solid (136 mg, 76%). 1H NMR (400 MHz, DMSO-$d_6$) δ ppm 12.35 (s, 1H) 7.62 (d, J=8.34 Hz, 1H) 7.54 (d, J=2.02 Hz, 1 H) 7.24 (dd, J=8.34, 2.02 Hz, 1H) 5.14 (s, 2H) 4.26 (q, J=7.07 Hz, 2H) 3.16 (sept, J=6.82 Hz, 1 H) 1.26 (t, J=7.07 Hz, 3H) 1.16 (d, J=6.82 Hz, 6H).

88b) N-{[2-[(3,4-Dichlorophenyl)methyl]-5-hydroxy-6-(1-methylethyl)-3-oxo-2,3-dihydro-4-pyridazinyl]carbonyl}glycine. Glycine, sodium salt (68.0 mg, 0.701 mmol) was added to a solution of the compound from example 88a) (135 mg, 0.350 mmol) in 2-methoxyethanol (2.5 ml) at room temperature. The reaction was heated to reflux and stirred for 2 h. The reaction was then cooled to room temperature and $H_2O$ added. The solution was filtered and 1N HCl added to precipitate the product. The product was filtered then purified by recrystallization from hot EtOH to give the title compound as a pale pink solid (81 mg, 56%). 1H NMR (400 MHz, DMSO-$d_6$) δ ppm 15.92 (s, 1H) 12.98 (s, 1H) 10.13 (t, J=5.31 Hz, 1H) 7.62 (d, J=8.08 Hz, 1H) 7.59 (d, J=1.77 Hz, 1H) 7.27 (dd, J=8.34, 2.02 Hz, 1H) 5.25 (s, 2H) 4.09 (d, J=5.56 Hz, 2H) 3.18 (sept, J=6.82 Hz, 1H) 1.19 (d, J=6.82 Hz, 6H).

Example 89

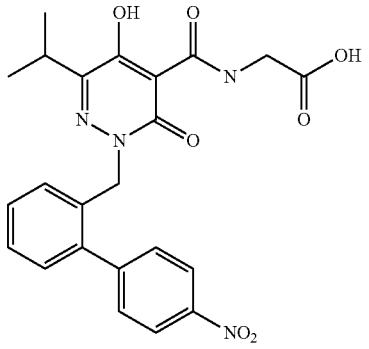

N-({5-Hydroxy-6-(1-methylethyl)-2-[(4'-nitro-2-biphenylyl)methyl]-3-oxo-2,3-dihydro-4-pyridazinyl}carbonyl)glycine To a 5 ml microwave tube was added N-{[2-[(2-bromophenyl)methyl]-5-hydroxy-6-(1-methylethyl)-3-oxo-2,3-dihydro-4-pyridazinyl]carbonyl}glycine (example 78(b), 75 mg, 0.177 mmol), (4-nitrophenyl)boronic acid (29.5 mg, 0.177 mmol), potassium carbonate (73.3 mg, 0.530 mmol), and tetrakis(triphenylphosphine)palladium (0) (6.13 mg, 5.30 μmol) in 1,4-Dioxane (1.5 ml) and Water (0.500 ml). The mixture was irradiated at 100° C. for 20 minutes. The reaction mixture was diluted with water (4 ml), acidified with 1N HCl (1 ml), and diluted with methanol (2 ml) then filtered to remove any residue followed by purification by HPLC chromatography (ODS silica, gradient 10-75% acetonitrile/water (0.1% TFA)) to afford the title compound N-({5-hydroxy-6-(1-methylethyl)-2-[(4'-nitro-2-biphenylyl)methyl]-3-oxo-2,3-dihydro-4-pyridazinyl}carbonyl)glycine (41 mg, 0.087 mmol, 49.2% yield) as a white powder. 1H NMR (400 MHz, DMSO-$d_6$) d ppm 10.04 (t, J=5.43 Hz, 1H), 8.27 (ddd, J=9.03, 2.40, 2.21 Hz, 2 H), 7.69 (ddd, J=9.03, 2.40, 2.21 Hz, 2H), 7.37-7.48 (m, 2H), 7.20-7.34 (m, 2H), 5.27 (s, 2H), 4.03 (d, J=5.81 Hz, 2H), 3.10 (sept, J=6.86 Hz, 1H), 1.09 (d, J=6.82 Hz, 6 H). MS (ES+) m/e 467 [M+H]+.

Example 90

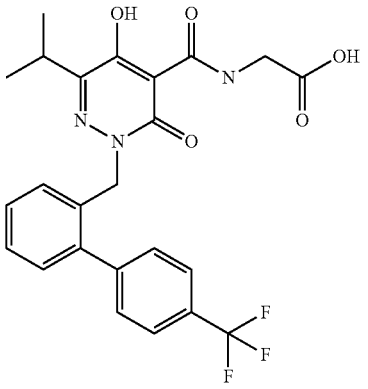

N-[(5-Hydroxy-6-(1-methylethyl)-3-oxo-2-{[4'-(trifluoromethyl)-2-biphenylyl]methyl}-2,3-dihydro-4-pyridazinyl)carbonyl]glycine To a 5 ml microwave tube was added N-{[2-[(2-bromophenyl)methyl]-5-hydroxy-6-(1-methylethyl)-3-oxo-2,3-dihydro-4-pyridazinyl]carbonyl}glycine (example 78(b), 75 mg, 0.177 mmol), 4-trifluoromethylphenylboronic Acid (33.6 mg, 0.177 mmol), potassium carbonate (73.3 mg, 0.530 mmol), and tetrakis(triphenylphosphine)palladium (0) (6.13 mg, 5.30 mol) in 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 10-75% acetonitrile/water (0.1% TFA)) to afford the title compound N-[(5-hydroxy-6-(1 -methylethyl)-3-oxo-2-{[4'-(trifluoromethyl)-2-biphenylyl]methyl}-2,3-dihydro-4-pyridazinyl)carbonyl]glycine (44 mg, 0.081 mmol, 45.8% yield) as a white powder. 1H NMR (400 MHz, DMSO-$d_6$) d ppm 15.81 (s, 1H), 12.99 (s, 1H), 10.05 (t, J=5.56 Hz, 1H), 7.77 (d, J=8.08 Hz, 2H), 7.61 (d, J=8.08 Hz, 2H), 7.35-7.49 (m, 2H), 7.21-

7.35 (m, 2H), 5.27 (s, 2H), 4.06 (d, J=5.56 Hz, 2H), 3.09 (sept, J=6.82 Hz, 1H), 1.09 (d, J=6.82 Hz, 6 H). MS (ES+) m/e 490 [M+H]+.

Example 91

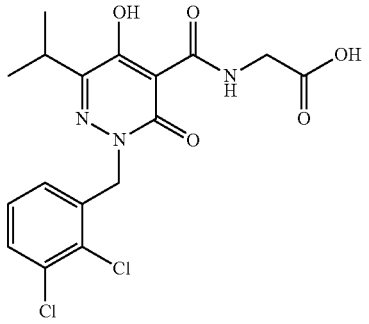

N-{[2-[(2,3-Dichlorophenyl)methyl]-5-hydroxy-6-(1-methylethyl)-3-oxo-2,3-dihydro-4-pyridazinyl] carbonyl}glycine 91a) Ethyl 2-[(2,3-dichlorophenyl)methyl]-5-hydroxy-6-(1-methylethyl)-3-oxo-2,3-dihydro-4-pyridazinecarboxylate. Sodium hydride (44 mg, 1.100 mmol) was added to a solution of the compound from example 14a) (100 mg, 0.442 mmol) in N,N-Dimethylformamide (DMF) (3 ml) at 0° C. The reaction was brought to room temperature and stirred for 40 minutes. The temperature was then reduced to 0° C. and 2,3-dichlorobenzyl bromide (106 mg, 0.442 mmol) was added. The reaction was brought to room temperature and stirred for 3 h. $H_2O$ was added followed by 1N HCl to precipitate the product. The product was filtered and purified by column chromatography ($SiO_2$, 15-40% EtOAc/Hexanes) to give the title compound as a white solid (130 mg, 76%). 1H NMR (400 MHz, DMSO-$d_6$) δ ppm 12.38 (s, 1H) 7.60 (dd, J=8.08, 1.52 Hz, 1H) 7.35 (t, J=7.83 Hz, 1H) 7.06 (dd, J=7.71, 1.39 Hz, 1H) 5.27 (s, 2H) 4.27 (q, J=7.24 Hz, 2H) 3.15 (sept, J=6.82 Hz, 1H) 1.26 (t, J=7.20 Hz, 3H) 1.11 (d, J=6.82 Hz, 6H).

91b) N-{[2-[(2,3-Dichlorophenyl)methyl]-5-hydroxy-6-(1-methylethyl)-3-oxo-2,3-dihydro-4-pyridazinyl] carbonyl}glycine. Glycine, sodium salt (35 mg, 0.361 mmol) was added to a solution of the compound from example 91a) (90 mg, 0.234 mmol) in Ethanol (3 ml) at room temperature. The reaction was heated in the microwave at 150° C. for 20 minutes. The reaction was cooled and $H_2O$ was added followed by 1N HCl to precipitate the product. The product was filtered and washed several times with $H_2O$ and Hexanes to give the title compound as a white solid (72 mg, 74%). 1H NMR (400 MHz, DMSO-$d_6$) δ ppm 15.96 (s, 1H) 12.98 (s, 1H) 10.11 (t, J=5.43 Hz, 1 H) 7.61 (dd, J=8.08, 1.52 Hz, 1H) 7.34 (t, J=7.83 Hz, 1H) 7.12 (dd, J=7.83, 1.26 Hz, 1H) 5.37 (s, 2H) 4.10 (d, J=5.81 Hz, 2H) 3.17 (m, 1H) 1.14 (d, J=6.82 Hz, 6H).

Example 92

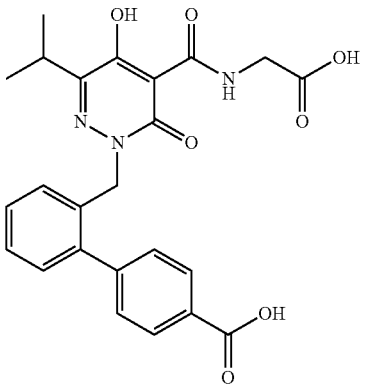

2'-{[5-{[(carboxymethyl)amino] carbonyl}-4-hydroxy-3-(1-methylethyl)-6-oxo-1(6H)-pyridazinyl] methyl}-4-biphenylcarboxylic acid To a 5 ml microwave tube was added N-{[2-[(2-bromophenyl)methyl]-5-hydroxy-6-(1-methylethyl)-3-oxo-2,3-dihydro-4-pyridazinyl]carbonyl}glycine (example 78(b), 75 mg, 0.177 mmol), 4-carboxybenzeneboronic acid (29.3 mg, 0.177 mmol), potassium carbonate (73.3 mg, 0.530 mmol), and tetrakis(triphenylphosphine)palladium (0) (6.13 mg, 5.30 μmol) in 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 10-75% acetonitrile/water (0.1% TFA)) to afford the title compound 2'-{[5-{[(carboxymethyl)amino]carbonyl}-4-hydroxy-3-(1-methylethyl)-6-oxo-1(6H)-pyridazinyl]methyl}-4-biphenylcarboxylic acid (non-preferred name) (30 mg, 0.064 mmol, 36.1% yield) as a white powder. 1H NMR (400 MHz, DMSO-$d_6$) d ppm 15.82 (s, 1H), 12.99 (br. s., 2 H), 10.06 (t, J=5.68 Hz, 1H), 7.99 (d, J=8.34 Hz, 2H), 7.52 (d, J=8.34 Hz, 2 H), 7.38 (dt, J=4.36, 2.24 Hz, 2H), 7.25-7.32 (m, 1H), 7.17-7.24 (m, 1H), 5.26 (s, 2H), 4.06 (d, J=5.56 Hz, 2H), 3.11 (sept, J=6.82 Hz, 1H), 1.10 (d, J=6.82 Hz, 6H). MS (ES+) m/e 466 [M+H]+.

Example 93

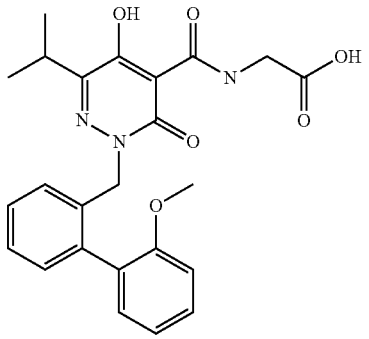

N-[(5-Hydroxy-6-(1-methylethyl)-2-{[2'-(methyloxy)-2-biphenylyl]methyl}-3-oxo-2,3-dihydro-4-pyridazinyl)carbonyl]glycine To a 5 ml microwave tube was added N-{[2-[(2-bromophenyl)methyl]-5-hydroxy-6-(1-methylethyl)-3-oxo-2,3-dihydro-4-pyridazinyl]carbonyl}glycine (example 78(b), 75 mg, 0.177 mmol), 2-methoxyphenylboronic acid (26.9 mg, 0.177 mmol), potassium carbonate (73.3 mg, 0.530 mmol), and tetrakis(triphenylphosphine)palladium (0) (6.13 mg, 5.30 μmol) in 1,4-Dioxane (1.5 ml) and Water (0.500 ml). The mixture was irradiated at 100° C. for 20 minutes. The reaction mixture was diluted with water (5 ml), acidified with 1N HCl (2 ml), and extracted with ethyl acetate (20 ml). The organic phase was dried over MgSO4, filtered, and solvents removed under reduced pressure. The crude residue was purified by HPLC chromatography (ODS silica, gradient 10-75% acetonitrile/water (0.1% TFA)) to afford the title compound N-[(5-hydroxy-6-(1-methylethyl)-2-{[2'-(methyloxy)-2-biphenylyl]methyl}-3-oxo-2,3-dihydro-4-pyridazinyl)carbonyl] glycine (40 mg, 0.088 mmol, 49.6% yield) as a white powder. 1H NMR (400 MHz, DMSO-$d_6$) d ppm 15.80 (s, 1H), 12.99 (br. s., 1H), 10.09 (t, J=4.93 Hz, 1 H), 7.26-7.39 (m, 3H), 7.04-7.19 (m, 4H), 6.98 (td, J=7.45, 0.76 Hz, 1H), 5.00-5.16 (m, rotomers, 2H), 4.06 (d, J=5.81 Hz, 2H), 3.74 (s, 3H), 3.08 (m, 1H), 1.03-1.13 (m, rotomers, 6H). MS (ES+) m/e 452 [M+H]+.

Example 94

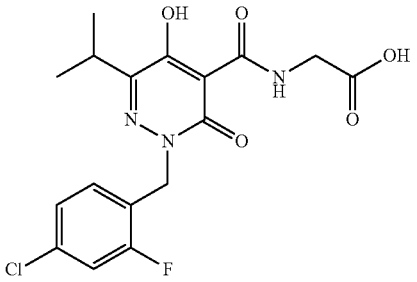

N-{[2-[(4-Chloro-2-fluorophenyl)methyl]-5-hydroxy-6-(1-methylethyl)-3-oxo-2,3-dihydro-4-pyridazinyl]carbonyl}glycine 94a) Ethyl 2-[(4-chloro-2-fluorophenyl)methyl]-5-hydroxy-6-(1-methylethyl)-3-oxo-2,3-dihydro-4-pyridazinecarboxylate. Sodium hydride (44 mg, 1.100 mmol) was added to a solution of the compound from example 14a) (100 mg, 0.442 mmol) in N,N-Dimethylformamide (DMF) (3 ml) at 0° C. The reaction was brought to room temperature and stirred for 40 minutes. The temperature was then reduced to 0° C. and 4-chloro-2-fluorobenzyl bromide (99 mg, 0.442 mmol) was added. The reaction was brought to room temperature and stirred for 3 h followed by the addition of 1N HCl. $H_2O$ and EtOAc were added and the layers separated. The aqueous layer was backextracted with EtOAc several times. The combined organic layers were washed with Brine, dried ($MgSO_4$), filtered and concentrated. The product was purified by column chromatography ($SiO_2$, 15-35% EtOAc/Hexanes) to give the title compound as a white solid (124 mg, 76%). 1H NMR (400 MHz, DMSO-$d_6$) δ ppm 12.32 (s, 1H) 7.45 (dd, J=9.73, 1.14 Hz, 1H) 7.24-7.31 (m, 2 H) 5.17 (s, 2H) 4.26 (q, J=7.24 Hz, 2H) 3.14 (sept, J=6.82 Hz, 1H) 1.26 (t, J=7.07 Hz, 3H) 1.12 (d, J=6.82 Hz, 6H).

94b) N-{[2-[(4-Chloro-2-fluorophenyl)methyl]-5-hydroxy-6-(1-methylethyl)-3-oxo-2,3-dihydro-4-pyridazinyl]carbonyl}glycine. Glycine, sodium salt (49 mg, 0.505 mmol) was added to a solution of the compound from example 94a) (94 mg, 0.255 mmol) in Ethanol (3 ml) at room temperature. The reaction was heated in the microwave at 150° C. for 20 minutes. The reaction was cooled and $H_2O$ added. The solution was filtered and 1N HCl added to precipitate the product. The product was filtered and purified by recrystallization from hot EtOH to give the title compound as a white solid (48 mg, 47%). 1H NMR (400 MHz, DMSO-$d_6$) δ ppm 15.92 (s, 1H) 12.97 (s, 1H) 10.12 (t, J=5.56 Hz, 1H) 7.47 (dd, J=9.98, 1.89 Hz, 1H) 7.22-7.36 (m, 2H) 5.28 (s, 2H) 4.10 (d, J=5.56 Hz, 2H) 3.16 (qq, J=6.85, 6.69 Hz, 1H) 1.16 (d, J=6.82 Hz, 6H).

Example 95

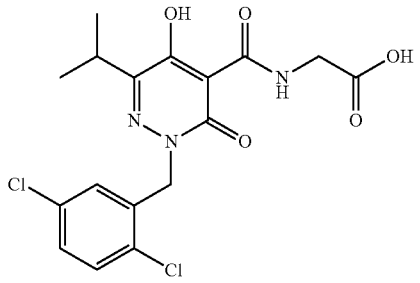

N-{[2-[(2,5-Dichlorophenyl)methyl]-5-hydroxy-6-(1-methylethyl)-3-oxo-2,3-dihydro-4-pyridazinyl]carbonyl}glycine 95a) Ethyl 2-[(2,5-dichlorophenyl)methyl]-5-hydroxy-6-(1-methylethyl)-3-oxo-2,3-dihydro-4-pyridazinecarboxylate. Sodium hydride (44 mg, 1.100 mmol) was added to a solution of the compound from example 14a) (100 mg, 0.442 mmol) in N,N-Dimethylformamide (DMF) (3 ml) at 0° C. The reaction was brought to room temperature and stirred for 40 minutes. The temperature was then reduced to 0° C. and 2,5-dichlorobenzyl bromide (106 mg, 0.442 mmol) was added. The reaction was brought to room temperature and stirred for 3 h followed by the addition of 1N HCl. The reaction was diluted with $H_2O$ and EtOAc and the layers separated. The aqueous phase was backextracted with EtOAc several times. The combined organic layers were washed with Brine, dried ($MgSO_4$), filtered and concentrated. The product was purified by column chromatography ($SiO_2$, 15-30% EtOAc/Hexanes) to give the title compound as a white solid (122 mg, 0.317 mmol, 72%). 1H NMR (400 MHz, DMSO-$d_6$) δ ppm 12.40 (s, 1H) 7.51-7.55 (m, 1H) 7.43 (dd, J=8.59, 2.53 Hz, 1H) 7.22 (d, J=2.53 Hz, 1H) 5.22 (s, 2H) 4.28 (q, J=7.07 Hz, 2H) 3.15 (qq, J=7.07, 6.82 Hz, 1H) 1.27 (t, J=7.07 Hz, 3H) 1.11 (d, J=6.82 Hz, 6H).

95b) N-{[2-[(2,5-Dichlorophenyl)methyl]-5-hydroxy-6-(1-methylethyl)-3-oxo-2,3-dihydro-4-pyridazinyl] carbonyl}glycine. Glycine, sodium salt (41 mg, 0.422 mmol) was added to a solution of the compound from example 95a) (82 mg, 0.213 mmol) in Ethanol (2 ml) at room temperature. The reaction was heated in the microwave at 150° C. for 15 minutes. The reaction was cooled and $H_2O$ added. The solution was filtered and 1N HCl added to precipitate the product. The product was filtered and purified by recrystallization from hot EtOH to give the title compound as a white solid (17 mg, 19%). 1H NMR (400 MHz, DMSO-$d_6$) δ ppm 15.95 (s, 1H) 12.97 (s, 1H) 10.11 (t, J=5.56 Hz, 1H) 7.54 (d, J=8.59 Hz, 1H) 7.44 (dd, J=8.59, 2.53 Hz, 1H) 7.32 (d, J=2.53 Hz, 1H) 5.32 (s, 2H) 4.10 (d, J=5.56 Hz, 2H) 3.17 (sept, J=6.82 Hz, 1H) 1.14 (d, J=6.82 Hz, 6H).

Example 96

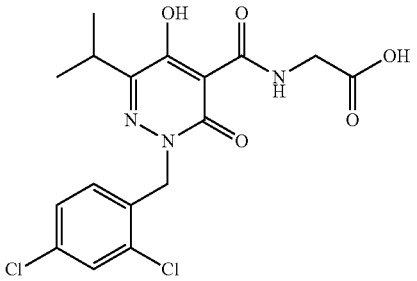

N-{[2-[(2,4-Dichlorophenyl)methyl]-5-hydroxy-6-(1-methylethyl)-3-oxo-2,3-dihydro-4-pyridazinyl] carbonyl}glycine 96a) Ethyl 2-[(2,4-dichlorophenyl)methyl]-5-hydroxy-6-(1-methylethyl)-3-oxo-2,3-dihydro-4-pyridazinecarboxylate. Sodium hydride (50 mg, 1.250 mmol) was added to a solution of the compound from example 14a) (113 mg, 0.499 mmol) in N,N-Dimethylformamide (DMF) (3 ml) at 0° C. The reaction was brought to room temperature and stirred for 40 minutes. The temperature was then reduced to 0° C. and 2,4-dichlorobenzyl chloride (0.07 ml, 0.501 mmol) was added. The reaction was brought to room temperature and stirred for 3 h followed by the addition of 1N HCl. The reaction was diluted with $H_2O$ and EtOAc and the layers separated. The aqueous phase was backextracted with EtOAc several times. The combined organic layers were washed with Brine, dried ($MgSO_4$), filtered and concentrated. The product was purified by column chromatography ($SiO_2$, 15-30% EtOAc/Hexanes) to give the title compound as a white solid (90 mg, 47%). 1H NMR (400 MHz, DMSO-$d_6$) δ ppm 12.36 (s, 1H) 7.66 (d, J=2.02 Hz, 1H) 7.42 (dd, J=8.34, 2.27 Hz, 1H) 7.16 (d, J=8.34 Hz, 1H) 5.21 (s, 2H) 4.27 (q, J=7.24 Hz, 2H) 3.14 (sept, J=6.78 Hz, 1 H) 1.26 (t, J=7.07 Hz, 3H) 1.11 (d, J=6.82 Hz, 6H).

96b) N-{[2-[(2,4-Dichlorophenyl)methyl]-5-hydroxy-6-(1-methylethyl)-3-oxo-2,3-dihydro-4-pyridazinyl] carbonyl}glycine. Glycine, sodium salt (44 mg, 0.453 mmol) was added to a solution of the compound from example 96a) (88 mg, 0.228 mmol) in 2-methoxyethanol (2 ml) at room temperature. The reaction was heated to refluxed for 2 h. The reaction was then cooled to room temperature and $H_2O$ added. The solution was filtered and 1N HCl added to precipitate the product. The product was filtered and washed several times with $H_2O$ and Hexanes to give the title compound as an off-white solid (43 mg, 45%). 1H NMR (400 MHz, DMSO-$d_6$) δ ppm 15.94 (s, 1H) 12.98 (s, 1H) 10.12 (t, J=5.56 Hz, 1H) 7.68 (d, J=2.02 Hz, 1H) 7.41 (dd, J=8.34, 2.27 Hz, 1H) 7.21 (d, J=8.34 Hz, 1H) 5.32 (s, 2H) 4.10 (d, J=5.81 Hz, 2H) 3.16 (sept, J=6.78 Hz, 1 H) 1.14 (d, J=6.82 Hz, 6H).

Example 97

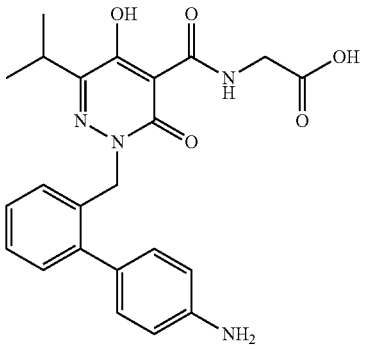

N-{[2-[(4'-Amino-2-biphenylyl)methyl]-5-hydroxy-6-(1-methylethyl)-3-oxo-2,3-dihydro-4-pyridazinyl] carbonyl}glycine To a Parr shaker flask was added N-({5-hydroxy-6-(1-methylethyl)-2-[(4'-nitro-2-biphenylyl)methyl]-3-oxo-2,3-dihydro-4-pyridazinyl}carbonyl)glycine (example 89, 65 mg, 0.139 mmol) and palladium on carbon (7.41 mg, 0.070 mmol) in Methanol (10 ml) and Ethyl acetate (2.500 ml) under a nitrogen atmosphere. The mixture was placed on a Parr shaker under 50 psi Hydrogen for 1 hour. The reaction mixture was filtered to remove the palladium on carbon followed by removal of the solvent by rotary evaporation and purification by HPLC chromatography (ODS silica, gradient 10-85% acetonitrile/water (0.1% TFA)) to afford the title compound N-{[2-[(4'-amino-2-biphenylyl)methyl]-5-hydroxy-6-(1-methylethyl)-3-oxo-2,3-dihydro-4-pyridazinyl] carbonyl}glycine (29 mg, 0.063 mmol, 45.3% yield) as a white powder. 1H NMR (400 MHz, DMSO-$d_6$) d ppm 15.86 (s, 1H), 10.11 (t, J=5.56 Hz, 1H), 7.19-7.36 (m, 5 H), 7.05 (d, J=7.07 Hz, 1H), 6.93 (d, J=7.33 Hz, 2H), 5.25 (s, 2H), 4.08 (d, J=5.56 Hz, 2H), 3.16 (sept, J=6.82 Hz, 1H), 1.15 (d, J=6.82 Hz, 6H). MS (ES+) m/e 437 [M+H]+.

Example 98

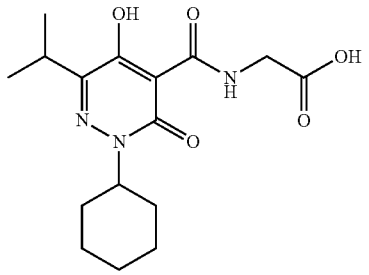

N-{[2-Cyclohexyl-5-hydroxy-6-(1-methylethyl)-3-oxo-2,3-dihydro-4-pyridazinyl]carbonyl}glycine 98$_a$) Ethyl-2-(cyclohexylhydrazono)-3-methylbutanoate. Ethyl 3-methyl-2-oxobutanoate (1 ml, 6.78 mmol) and DBU (1.23 ml, 8.16 mmol) were added to a solution of cyclohexylhydrazine hydrochloride (1.23 g, 8.16 mmol) in Ethanol (10 ml) at room temperature. The reaction was heated in the microwave at 150° C. for 45 min. The reaction was cooled and diluted with $H_2O$ and EtOAc. The layers were separated and the aqueous layer backextracted with EtOAc several times. The combined organic layers were washed with 1N HCl (2×) and Brine. The solution was dried ($MgSO_4$), filtered, and concentrated. The product was purified by column chromatography ($SiO_2$, 5-20% EtOAc/Hexanes) to give the title compound as a colorless oil (1.21 g, 74%). 1H NMR (400 MHz, DMSO-$d_6$) d ppm 9.94 (d, J=5.05 Hz, 1H) 4.15 (q, J=7.24 Hz, 2H) 3.16-3.31 (m, J=13.89, 9.35, 4.80 Hz, 1H) 2.82 (sept, J=6.78 Hz, 1H) 1.78-1.92 (m, 2H) 1.46-1.73 (m, 3H) 1.26-1.38 (m, 4H) 1.24 (t, J=7.07 Hz, 3H) 1.08-1.21 (m, 1H) 1.02 (d, J=6.82 Hz, 6H).

98b) Ethyl-2-{cyclohexyl[3-(ethyloxy)-3-oxopropanoyl]hydrazono}-3-methylbutanoate. DBU (0.35 ml, 2.322 mmol) was added to a solution of the compound from example 98a) (0.51 g, 2.122 mmol) in Tetrahydrofuran (THF) (1 ml) at 0° C. The reaction was brought to room temperature and stirred for 10 minutes. The temperature was then reduced to 0° C. and ethyl malonyl chloride (0.32 ml, 2.374 mmol) was added. The reaction was brought to room temperature and stirred for 2.5 h. 1N HCl was added and the solution diluted with $H_2O$ and EtOAc. The layers were separated and aqueous phase backextracted with EtOAc several times. The combined organic layers were washed with Brine, dried ($MgSO_4$), filtered and concentrated. The product was purified by column chromatography ($SiO_2$, 10-25% EtOAc/Hexanes) to give a mixture of the title compound and the cyclized product 55c) (126 mg, 13%). LCMS ($ES^+$) m/z 355.2, 309.2 (MH+).

98c) Ethyl 2-cyclohexyl-5-hydroxy-6-(1-methylethyl)-3-oxo-2,3-dihydro-4-pyridazinecarboxylate. DBU (0.06 mL, 0.398 mmol) was added to a solution of the compound from example 98b) (92 mg, 0.260 mmol) in 1,4-dioxane (1.5 ml) at room temperature. The reaction was heated in the microwave at 130° C. for 20 minutes. The reaction was cooled and $H_2O$ and EtOAc were added. The layers were separated and the aqueous phase backextracted with EtOAc several times. The combined organic layers were washed with Brine, dried ($MgSO_4$), filtered and concentrated. The product was purified by column chromatography ($SiO_2$, 10-20% EtOAc/Hexanes) to give the title compound as a colorless oil (36 mg, 45%). 1H NMR (400 MHz, DMSO-$d_6$) d ppm 12.06 (s, 1H) 4.66 (tt, J=11.37, 4.04 Hz, 1H) 4.26 (q, J=7.07 Hz, 2H) 3.15 (sept, J=6.78 Hz, 1H) 1.51-1.89 (m, 7H) 1.29-1.44 (m, 2H) 1.26 (t, J=7.07 Hz, 3H) 1.16 (d, J=6.82 Hz, 6H) 1.08-1.22 (m, 1H).

98d) N-{[2-Cyclohexyl-5-hydroxy-6-(1 -methylethyl)-3-oxo-2,3-dihydro-4-pyridazinyl]carbonyl}glycine. Glycine, sodium salt (19 mg, 0.196 mmol) was added to a solution of the compound from example 98c) (30 mg, 0.097 mmol) in 2-methoxyethanol (1 ml) at room temperature. The reaction was heated to reflux and stirred for 2 h. The reaction was cooled and diluted with $H_2O$. The solution was filtered and 1N HCl added to precipitate the product. The product was filtered and washed with $H_2O$ and Hexanes to give the title compound as a white solid (24 mg, 73%). 1H NMR (400 MHz, DMSO-$d_6$) δ ppm 15.77 (s, 1H) 13.01 (s, 1H) 10.35 (t, J=4.80 Hz, 1H) 4.67-4.83 (m, 1H) 4.11 (d, J=5.56 Hz, 2H) 3.18 (sept, J=6.86 Hz, 1H) 1.55-1.91 (m, 7H) 1.31-1.48 (m, 2H) 1.20 (d, J=6.82 Hz, 6H) 1.14-1.25 (m, 1 H).

Example 99

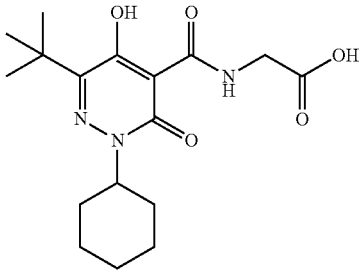

N-{[2-Cyclohexyl-6-(1,1-dimethylethyl)-5-hydroxy-3-oxo-2,3-dihydro-4-pyridazinyl]carbonyl}glycine 99a) Ethyl-2-(cyclohexylhydrazono)-3,3-dimethylbutanoate. To a solution of trimethylpyruvic acid (0.6 g, 2.77 mmol) in MTBE (4.0 ml) was added DBU (0.58 ml, 3.85 mmol) followed by bromoethane (0.5 ml, 6.70 mmol) at room temperature. The reaction was heated in the microwave at 120° C. for 20 minutes. The reaction was cooled and 10% $NaHCO_3$ (aq) added. The layers were separated and the organic layer was washed again with 10% $NaHCO_3$ (aq). The aqueous layer backextracted with $Et_2O$ several times. The combined organic layers were washed with Brine, dried ($MgSO_4$), filtered and concentrated. The resulting oil was redissolved in Ethanol (5.0 mL) and cyclohexylhydrazine hydrochloride (0.500 g, 3.32 mmol) and DBU (0.500 ml, 3.32 mmol) were added. The reaction was heated in the microwave at 150° C. for 25 minutes. The reaction was cooled to room temperature and 1N HCl added. The solution was diluted with $H_2O$ and EtOAc and the layers separated. The aqueous layer was backextracted with EtOAc several times. The combined organic layers were washed with Brine, dried ($MgSO_4$), filtered and concentrated. The product was purified by column chromatography ($SiO_2$, 5-15% EtOAc/Hexanes) to give the title compound as a colorless oil (0.403 g, 57%). 1H NMR (400 MHz, DMSO-$d_6$) d ppm 9.32 (d, J=4.80 Hz, 1H) 4.20 (q, J=7.07 Hz, 2H) 3.08-3.26 (m, 1H) 1.79-1.94 (m, 2H) 1.48-1.74 (m, 3H) 1.26 (t, J=7.07 Hz, 3H) 1.22-1.37 (m, 5H) 1.15 (s, 9H).

99b) Ethyl-2-{cyclohexyl[3-(ethyloxy)-3-oxopropanoyl]hydrazono}-3,3-dimethylbutanoate. DBU (0.21 ml, 1.393 mmol) was added to a solution of the compound from example 99a) (0.323 g, 1.270 mmol) in Tetrahydrofuran (THF) (1 ml) at 0° C. The reaction was brought to room temperature and stirred for 10 minutes. The temperature was then reduced to 0° C. and ethyl malonyl chloride (0.19 ml, 1.410 mmol) was added. The reaction stirred for 2.5 h at room temperature followed by the addition of 1N HCl. The solution was diluted with $H_2O$ and EtOAc and the layers separated. The aqueous phase was backextracted with EtOAc several times. The combined organic layers were washed with Brine, dried ($MgSO_4$), filtered and concentrated. The product was purified by column chromatography ($SiO_2$, 5-25% EtOAc/Hexanes) to give a mixture of the title compound and the cyclized product 56c) (197 mg, 42%). LCMS (ES+) m/z 369.0, 323.0 ($MH^+$).

99c) Ethyl 2-cyclohexyl-6-(1,1-dimethylethyl)-5-hydroxy-3-oxo-2,3-dihydro-4-pyridazinecarboxylate. DBU (0.11 ml, 0.730 mmol) was added to a solution of the compound from example 99b) (173 mg, 0.470 mmol) in 1,4-dioxane (2.5 ml) at room temperature. The reaction was heated to reflux and stirred for 2 h. The reaction was cooled back to room temperature and $H_2O$ was added. The solution was filtered and 1N HCl was added to precipitate the product as a tan gum. The gum was filtered and washed with $H_2O$ and Hexanes. The product was purified by recrystallization from hot $CH_2Cl_2$ to give the title compound as a white solid (103 mg, 77%). 1H NMR (400 MHz, DMSO-$d_6$) d ppm 12.39 (s, 1H) 4.65 (tt, J=11.49, 3.79 Hz, 1H) 4.27 (q, J=7.07 Hz, 2H) 1.52-1.87 (m, 7H) 1.33-1.44 (m, 2H) 1.32 (s, 9 H) 1.26 (t, J=7.07 Hz, 3H) 1.06-1.21 (m, 1H).

99d) N-{[2-Cyclohexyl-6-(1,1-dimethylethyl)-5-hydroxy-3-oxo-2,3-dihydro-4-pyridazinyl]carbonyl}glycine. Glycine, sodium salt (58 mg, 0.598 mmol) was added to a solution of the compound from example 99c) (97 mg, 0.301 mmol) in 2-methoxyethanol (1.5 mL) at room temperature. The reaction was heated to reflux and stirred for 1.5 h. The reaction was then cooled to room temperature and $H_2O$ was added. The solution was filtered and 1N HCl added to precipitate the product. The product was filtered and redissolved in $CH_2Cl_2$. The solution was concentrated under reduced pressure and Hexanes added. The product was filtered to give the title compound as an off-white solid (79 mg, 75%). 1H NMR (400 MHz, DMSO-$d_6$) δ ppm 16.27 (s, 1 H) 13.01 (s, 1H) 10.45 (t, J=5.43 Hz, 1H) 4.66-4.83 (m, 1H) 4.12 (d, J=5.56 Hz, 2H) 1.57-1.89 (m, 7H) 1.36-1.52 (m, 2H) 1.34 (s, 9H) 1.05-1.30 (m, 1H).

Example 100

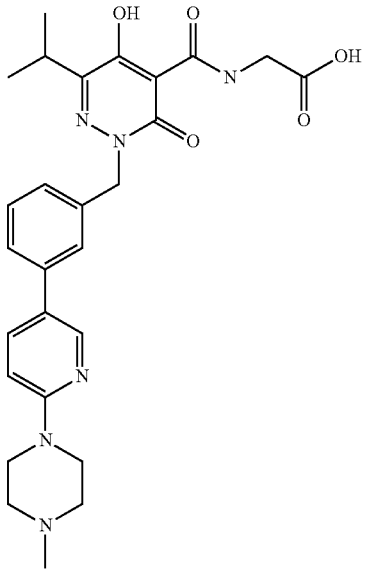

N-{[5-Hydroxy-6-(1-methylethyl)-2-({3-[6-(4-methyl-1-piperazinyl)-3-pyridinyl]phenyl}methyl)-3-oxo-2,3-dihydro-4-pyridazinyl]carbonyl}glycine To a 5 mL microwave tube was added N-{[2-[(3-bromophenyl)methyl]-5-hydroxy-6-(1-methylethyl)-3-oxo-2,3-dihydro-4-pyridazinyl]carbonyl}glycine (example 79, 31 mg, 0.073 mmol), 1-methyl-4-[5-(4,4,5,5-tetramethyl-1,3,2-dioxaborolan-2-yl)-2-pyridinyl]piperazine (22.16 mg, 0.073 mmol), potassium carbonate (303 mg, 2.192 mmol), and tetrakis(triphenylphosphine)palladium (0) (2.53 mg, 2.192 μmol) in 1,4-Dioxane (1.5 ml) and Water (0.500 ml). The mixture was irradiated at 100° C. for 20 minutes. The reaction mixture was diluted with water (4 ml) and acidified with 1N HCl (1 ml) then filtered to remove any residue followed by purification by HPLC chromatography (ODS silica, gradient 10-75% acetonitrile/water (0.1% TFA)) to afford the title compound N-{[5-hydroxy-6-(1 -methylethyl)-2-({3-[6-(4-methyl-1-piperazinyl)-3-pyridinyl]phenyl}methyl)-3-oxo-2,3-dihydro-4-pyridazinyl]carbonyl}glycine (32 mg, 0.048 mmol, 65.7% yield) as a white powder. 1H NMR (400 MHz, DMSO-$d_6$) d ppm 15.88 (s, 1H), 12.98 (br. s., 1H), 10.18 (t, J=5.56 Hz, 1 H), 9.71 (br. s., 1H), 8.46 (d, J=2.27 Hz, 1H), 7.91 (dd, J=8.84, 2.53 Hz, 1H), 7.52-7.61 (m, 2H), 7.42 (t, J=8.08 Hz, 1H), 7.23 (d, J=7.58 Hz, 1H), 7.07 (d, J=9.09 Hz, 1H), 5.32 (s, 2H), 4.48 (d, J=12.63 Hz, 2H), 4.09 (d, J=5.56 Hz, 2H), 3.52 (d, J=10.36 Hz, 2H), 3.00-3.26 (m, 5H), 2.86 (d, J=4.04 Hz, 3H), 1.21 (d, J=6.82 Hz, 6H). MS (ES+) m/e 521 [M+H]+.

Example 101

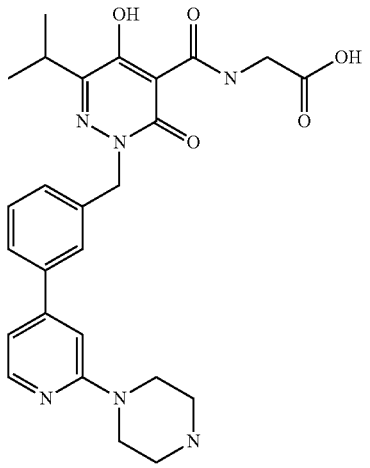

N-{[5-Hydroxy-6-(1-methylethyl)-3-oxo-2-({3-[2-(1-piperazinyl)-4-pyridinyl]phenyl}methyl)-2,3-dihydro-4-pyridazinyl]carbonyl}glycine To a 5 mL microwave tube was added N-{[2-[(3-bromophenyl)methyl]-5-hydroxy-6-(1-methylethyl)-3-oxo-2,3-dihydro-4-pyridazinyl]carbonyl}glycine (example 79, 31 mg, 0.073 mmol), 1-[4-(4,4,5,5-tetramethyl-1,3,2-dioxaborolan-2-yl)-2-pyridinyl]piperazine (21.13 mg, 0.073 mmol), potassium carbonate (30.3 mg, 0.219 mmol), and tetrakis(triphenylphosphine)palladium (0) (2.53 mg, 2.192 μmol) in 1,4-Dioxane (1.5 ml) and Water (0.500 ml). The mixture was irradiated at 100° C. for 20 minutes. The reaction mixture was diluted with water (3 ml) and acidified with 1N HCl. The mixture was then filtered to remove residual salts and purified by HPLC chromatography (ODS silica, gradient 10-75% acetonitrile/water (0.1% TFA)). The title compound, N-{[5-hydroxy-6-(1-methylethyl)-3-oxo-2-({3-[2-(1-piperazinyl)-4-pyridinyl]phenyl}methyl)-2,3-dihydro-4-pyridazinyl]carbonyl}glycine (22 mg, 0.034 mmol, 46.2% yield), was obtained as a white solid tfa salt. 1H NMR (400 MHz, DMSO-$d_6$) d ppm 15.88 (s, 1 H), 12.90 (br. s., 1H), 10.17 (t, J=5.81 Hz, 1H), 8.75 (br. s., 2H), 8.22 (d, J=5.56 Hz, 1H), 7.72 (s, 1H), 7.70 (d, J=8.59 Hz, 1H), 7.48 (t, J=7.71 Hz, 1H), 7.35 (d, J=7.58 Hz, 1H), 7.14 (s, 1H), 7.01 (dd, J=5.31, 1.01 Hz, 1H), 5.34 (s, 2H), 4.09 (d, J=5.56 Hz, 2H), 3.75-3.84 (m, 4H), 3.13-3.27 (m, 5H), 1.21 (d, J=6.82 Hz, 6H). MS (ES+) m/e 507 [M+H]+.

Example 102

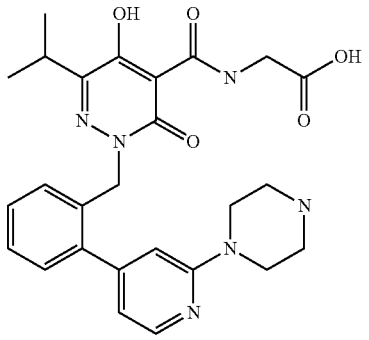

N-{[5-Hydroxy-6-(1-methylethyl)-3-oxo-2-({2-[2-(1-piperazinyl)-4-pyridinyl]phenyl}methyl)-2,3-dihydro-4-pyridazinyl]carbonyl}glycine To a 5 mL microwave tube was added N-{[2-[(2-bromophenyl)methyl]-5-hydroxy-6-(1-methylethyl)-3-oxo-2,3-dihydro-4-pyridazinyl]carbonyl}glycine (example 78(b), 75 mg, 0.177 mmol), 1-[4-(4,4,5,5-tetramethyl-1,3,2-dioxaborolan-2-yl)-2-pyridinyl]piperazine (51.1 mg, 0.177 mmol), potassium carbonate (73.3 mg, 0.530 mmol), and tetrakis(triphenylphosphine)palladium (0) (6.13 mg, 5.30 μmol) in 1,4-Dioxane (1.5 ml) and Water (0.500 ml). The mixture was irradiated at 100° C. for 20 minutes. The reaction mixture was diluted with water (3 ml) and 1N HCl (1 mL). The mixture was then filtered to remove residual salts and purified by HPLC chromatography (ODS silica, gradient 10-75% acetonitrile/water (0.1% TFA)). The title compound, N-{[5-hydroxy-6-(1-methylethyl)-3-oxo-2-({2-[2-(1 -piperazinyl)-4-pyridinyl]phenyl}methyl)-2,3-dihydro-4-pyridazinyl]carbonyl}glycine (52 mg. 0.083 mmol, 47.0% yield), was obtained as a white solid (tfa salt) after trituration with ether. 1H NMR (400 MHz, DMSO-$d_6$) d ppm 15.83 (s, 1 H), 13.02 (br. s., 1H), 10.07 (t, J=5.43 Hz, 1H), 8.79 (br. s., 2H), 8.19 (d, J=5.05 Hz, 1H), 7.39 (dd, J=5.68, 3.41 Hz, 2H), 7.24-7.31 (m, 1H), 7.21 (dd, J=5.43, 3.66 Hz, 1H), 6.93 (s, 1H), 6.78 (d, J=5.05 Hz, 1H), 5.30 (s, 2H), 4.08 (d, J=5.56 Hz, 2H), 3.69-3.85 (m, 4H), 3.20 (br. s., 4H), 3.12 (m, 1H), 1.12 (d, J=6.82 Hz, 6H). MS (ES+) m/e 507 [M+H]+.

Example 103

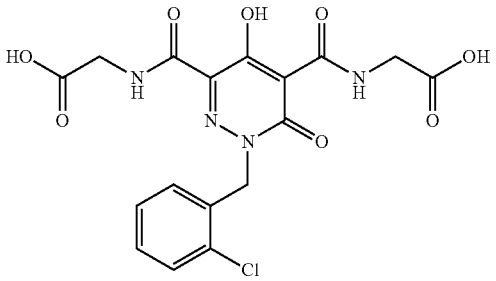

2,2'-{{1-[(2-Chlorophenyl)methyl]-4-hydroxy-6-oxo-1,6-dihydropyridazine-3,5-diyl}bis[oxomethanediyl)imino]}diacetic acid 103a) Diethyl 4-hydroxy-6-oxo-1,6-dihydro-3,5-pyridazinedicarboxylate. Diethyl ketomalonate (5 ml, 32.8 mmol) and catalytic AcOH (0.45 ml, 7.86 mmol) were added to a solution of ethyl-3-hydrazino-3-oxopropionate (5.75 g, 39.3 mmol) in Ethanol (50 ml) at room temperature. The reaction was heated to reflux and stirred for 3.5 h. The reaction was then cooled to room temperature and solvent removed under reduced pressure. The residue was redissolved in EtOAc and washed with 1N HCl (2×). The aqueous phase was backextracted with EtOAc several times. The combined organic layers were washed with Brine, dried ($MgSO_4$), filtered and concentrated to give a yellow oil. The oil was dissolved in Ethanol (60 ml) and DBU (7.4 ml, 49.1 mmol) was added at room temperature. The reaction was heated to reflux and stirred for 2 h. The reaction was cooled to and $H_2O$ was added followed by 6N HCl to precipitate the product. The suspension was cooled to 0° C. and allowed to set for 15 min. The solid was filtered and washed several times with $H_2O$ and Hexanes. The product was purified by recrystallization from hot EtOH to give the title compound as a brown solid (1.73 g, 21%). 1H NMR (400 MHz, DMSO-$d_6$) δ ppm 13.53 (s, 1H) 4.34 (q, J=7.24 Hz, 2H) 4.27 (q, J=7.07 Hz, 2H) 1.31 (t, J=7.20 Hz, 3H) 1.26 (t, J=7.20 Hz, 3H).

103b) Diethyl 1-[(2-chlorophenyl)methyl]-4-hydroxy-6-oxo-1,6-dihydro-3,5-pyridazinedicarboxylate. Sodium hydride (273 mg, 6.83 mmol) was added to a solution of the compound from example 103a) (700 mg, 2.73 mmol) in N,N-Dimethylformamide (DMF) (10 ml) at 0° C. The reaction was brought to room temperature and stirred for 30 minutes. The temperature was then reduced to 0° C. and 2-chlorobenzyl bromide (0.36 ml, 2.77 mmol) was added. The reaction was brought to room temperature and stirred for 3.5 h followed by the addition of 1N HCl. $H_2O$ and EtOAc were added and the layers separated. The aqueous phase was backextracted with EtOAc several times. The combined organic layers were washed with Brine, dried ($MgSO_4$), filtered and concentrated. The product was purified by column chromatography ($SiO_2$, 0-5% MeOH/$CH_2Cl_2$) to give the title compound as a light yellow solid (681 mg, 66%). 1H NMR (400 MHz, DMSO-$d_6$) δ ppm 7.48-7.53 (m, 1H) 7.24-7.42 (m, 2H) 7.03-7.15 (m, 1H) 5.34 (s, 2H) 4.33 (q, J=7.07 Hz, 2H) 4.27 (q, J=7.07 Hz, 2H) 1.28 (t, J=7.07 Hz, 3H) 1.26 (t, J=7.07 Hz, 3H).

103c) 2,2'-{{1-[(2-Chlorophenyl)methyl]-4-hydroxy-6-oxo-1,6-dihydropyridazine-3,5-diyl}bis[oxomethanediyl) imino]}diacetic acid. Glycine, sodium salt (175 mg, 1.799 mmol) was added to a solution of the compound from example 103b) (571 mg, 1.500 mmol) in Ethanol (10 ml) at room temperature. The reaction was heated in the microwave at 120° C. for 25 minutes. The reaction was cooled and solvent removed under reduced pressure. $H_2O$ was added followed by 1N HCl to precipitate the product. The solid was filtered then redissolved in DMSO. The product was purified by HPLC (10-85% ACN/$H_2O$) to give the title compound as a white solid (13 mg, 2%). 1H NMR (400 MHz, DMSO-$d_6$) δ ppm 16.26 (s, 1H) 12.99 (s, 1H) 12.75 (s, 1H) 10.00 (t, J=5.43 Hz, 1H) 8.85 (s, 1H) 7.51 (dd, J=7.71, 1.39 Hz, 1H) 7.27-7.39 (m, 2H) 7.10-7.16 (m, 1H) 5.40 (s, 2H) 4.11 (d, J=5.56 Hz, 2H) 3.95 (d, J=5.81 Hz, 2H).

Example 104

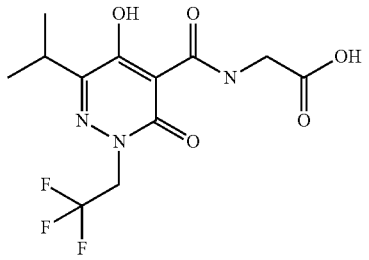

N-{[5-Hydroxy-6-(1-methylethyl)-3-oxo-2-(2,2,2-trifluoroethyl)-2,3-dihydro-4-pyridazinyl] carbonyl}glycine 104a) Ethyl-3-methyl-2-[(2,2,2-trifluoroethyl)hydrazono] butanoate. To a microwave tube was added ethyl-3-methyl-2-oxobutyrate (2.212 g, 15.34 mmol) and 2,2,2-trifluoroethylhydrazine (2.5 g, 15.34 mmol) in Ethanol (10 ml) and Acetic Acid (0.5 ml). The reaction was irridatiated at 150° C. for 20 minutes. The reaction mixture was partitioned between water (15 ml) and ethyl acetate (25 ml) the organic layer separated. After another extraction the organic layers were combined, dried over MgSO4, filtered then evaporated down to give a clear oil. The crude oil was purified by flash column chromatography (5%-25% EtOAc:Hexanes) to give the product as a clear oil (ethyl-3-methyl-2-[(2,2,2-trifluoroethyl)hydrazono]butanoate (2.55 g, 10.51 mmol, 68.5% yield). 1H NMR (400 MHz, CHLOROFORM-d) d ppm 10.07 (s, 1H), 4.26 (q, J=7.07 Hz, 2H), 3.92 (dq, J=8.88, 5.18 Hz, 2H), 2.91 (sept, J=6.78 Hz, 1H), 1.35 (t, J=7.20 Hz, 3H), 1.10 (d, J=6.82 Hz, 6H). MS (ES+) m/e 241 [M+H]+.

104b) Ethyl-5-hydroxy-6-(1-methylethyl)-3-oxo-2-(2,2,2-trifluoroethyl)-2,3-dihydro-4-pyridazinecarboxylate. To a microwave tube was added ethyl-3-methyl-2-[(2,2,2-trifluoroethyl)hydrazono]butanoate (2.5 g, 10.41 mmol) and Ethyl Malonyl Chloride (1.539 ml, 11.45 mmol) in 1,4-Dioxane (15 ml). The reaction was irridatiated at 150° C. for 20 minutes. The crude reaction mixture was evaporated down to give a yellow oil. The crude oil was resuspended in 1,4-Dioxane (20 ml) and DBU (1.726 ml, 11.45 mmol) was added. The solution was irridatiated at 150° C. for 20 minutes, diluted with water (5 ml) and acidified with 6N HCl. The crude oil was purified by flash column chromatography (5%-25% EtOAc: Hexanes). The desired product was inseparable but present by LCMS and the material carried on to the next step. ethyl 5-hydroxy-6-(1 -methylethyl)-3-oxo-2-(2,2,2-trifluoroethyl)-2,3-dihydro-4-pyridazinecarboxylate (50 mg, 0.162 mmol, 1.559% yield). MS (ES+) m/e 309 [M+H]+.

104c) N-{[5-Hydroxy-6-(1-methylethyl)-3-oxo-2-(2,2,2-trifluoroethyl)-2,3-dihydro-4-pyridazinyl]carbonyl}glycine. To a 20 mL microwave tube was added ethyl 5-hydroxy-6-(1-methylethyl)-3-oxo-2-(2,2,2-trifluoroethyl)-2,3-dihydro-4-pyridazinecarboxylate (35 mg, 0.114 mmol) and Glycine Sodium Salt (27.5 mg, 0.284 mmol) in 2-methoxyethanol (2 ml) and the mixture was irradiated at 150° C. for 20 minutes. The reaction mixture was diluted with water (10 ml) and acidified with 1N HCl to give a off-white precipitate that was collected by filtration and washed with water, hexanes and ether to give N-{[5-hydroxy-6-(1-methylethyl)-3-oxo-2-(2,2,2-trifluoroethyl)-2,3-dihydro-4-pyridazinyl] carbonyl}glycine (21 mg, 0.062 mmol, 54.3% yield). 1H NMR (400 MHz, DMSO-$d_6$) d ppm 16.25 (br. s., 1H), 13.01 (br. s., 1H), 10.01 (t, J=5.68 Hz, 1H), 4.95 (q, J=9.01 Hz, 2H), 4.12 (d, J=5.56 Hz, 2H), 3.12-3.25 (m, 1 H), 1.19 (d, J=6.82 Hz, 6H). MS (ES+) m/e 338 [M+H]+.

Example 105

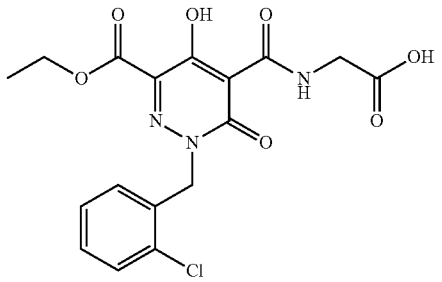

N-({2-[(2-Chlorophenyl)methyl]-6-[(ethyloxy)carbonyl]-5-hydroxy-3-oxo-2,3-dihydro-4-pyridazinyl}carbonyl)glycine Glycine, sodium salt (175 mg, 1.799 mmol) was added to a solution of the compound from example 103b) (571 mg, 1.500 mmol) in Ethanol (10 ml) at room temperature. The reaction was heated in the microwave at 120° C. for 25 minutes. The reaction was cooled and solvent removed under reduced pressure. $H_2O$ was added followed by 1N HCl to precipitate the product. The solid was filtered then redissolved in DMSO. The product was purified by HPLC (10-85% ACN/$H_2O$) to give the title compound as a white solid (75 mg, 12%). 1H NMR (400 MHz, DMSO-$d_6$) δ ppm 13.01 (s, 1H) 9.96 (t, J=5.05 Hz, 1H) 7.51 (dd, J=7.71, 1.39 Hz, 1H)

7.27-7.40 (m, 2H) 7.17 (dd, J=7.58, 1.52 Hz, 1H) 5.41 (s, 2H) 4.32 (q, J=7.07 Hz, 2H) 4.10 (d, J=5.81 Hz, 2H) 1.28 (t, J=7.20 Hz, 3H).

Example 106

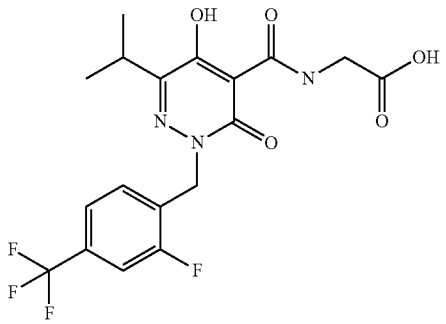

N-{[2-{[2-Fluoro-4-(trifluoromethyl)phenyl]methyl}-5-hydroxy-6-(1-methylethyl)-3-oxo-2,3-dihydro-4-pyridazinyl]carbonyl}glycine 106a) Ethyl 2-{[2-fluoro-4-(trifluoromethyl)phenyl]methyl}-5-hydroxy-6-(1-methylethyl)-3-oxo-2,3-dihydro-4-pyridazinecarboxylate. To a solution of ethyl 5-hydroxy-6-(1-methylethyl)-3-oxo-2,3-dihydro-4-pyridazinecarboxylate (example 14(a), 0.5 g, 2.210 mmol) in N,N-Dimethylformamide (DMF) (50 ml) at 0° C. was added sodium hydride (0.133 g, 3.32 mmol) in portions. The reaction mixture was stirred at room temperature for 45 minutes and then cooled back to 0° C. and 1-(bromomethyl)-2-fluoro-4-(trifluoromethyl)benzene (0.568 g, 2.210 mmol) was added portionwise. The mixture was stirred at ambient temperature for 2.5 hours then quenched with 1N HCl (2 ml) and diluted with water (10 ml). The aqueous solution was extracted with ethyl acetate (2×30 ml), the organic layers combined and washed with water (100 ml) and brine (100 ml), dried over Magnesium sulfate, filtered and solvents removed with rotary evaporation. The crude oil was purified by flash column chromatography (5-100% ethyl acetate in hexanes) to provide the title compound (ethyl 2-{[2-fluoro-4-(trifluoromethyl)phenyl]methyl}-5-hydroxy-6-(1-methylethyl)-3-oxo-2,3-dihydro-4-pyridazinecarboxylate (335 mg, 0.749 mmol, 33.9% yield) as a clear oil. 1H NMR (400 MHz, DMSO-$d_6$) dppm 12.36 (s, 1H), 7.67-7.73 (m, 1H), 7.58 (d, J=8.84 Hz, 1H), 7.45 (t, J=7.58 Hz, 1H), 5.27 (s, 2H), 4.27 (q, J=7.07 Hz, 2H), 3.15 (sept, J=6.78 Hz, 1H), 1.26 (t, J=7.07 Hz, 3H), 1.13 (d, J=6.82 Hz, 6H). MS (ES+) m/e 403 [M+H]+.

106b) N-{[2-{[2-Fluoro-4-(trifluoromethyl)phenyl]methyl}-5-hydroxy-6-(1 -methylethyl)-3-oxo-2,3-dihydro-4-pyridazinyl]carbonyl}glycine. To a 5 mL microwave tube was added ethyl 2-{[2-fluoro-4-(trifluoromethyl)phenyl]methyl}-5-hydroxy-6-(1 -methylethyl)-3-oxo-2,3-dihydro-4-pyridazinecarboxylate (275 mg, 0.684 mmol) and Glycine Sodium Salt (166 mg, 1.709 mmol) in 2-methoxyethanol (2 ml) and the mixture was irradiated at 150° C. for 20 minutes. The crude reaction mixture turned a violet blue. The mixture was diluted with water (10 ml) and acidified with 1N HCl. The aqueous solution was then extracted with ethyl acetate (40 mL), organics dried over MgSO4, filtered and solvents removed by evaporation. The crude blue oil was purified by HPLC chromatography (ODS silica, gradient 25-95% acetonitrile/water (0.1% TFA)) to afford the title compound, N-{[2-{[2-fluoro-4-(trifluoromethyl)phenyl]methyl}-5-hydroxy-6-(1-methylethyl)-3-oxo-2,3-dihydro-4-pyridazinyl]carbonyl}glycine (45 mg, 0.103 mmol, 15.11% yield), as a white solid. 1H NMR (400 MHz, DMSO-$d_6$) d ppm 15.94 (s, 1H), 12.97 (br. s., 1H), 10.09 (t, J=5.18 Hz, 1H), 7.72 (d, J=10.11 Hz, 1H), 7.54-7.62 (m, 1H), 7.49 (t, J=7.45 Hz, 1H), 5.38 (s, 2H), 4.09 (d, J=5.56 Hz, 2H), 3.17 (sept, J=6.82 Hz, 1H), 1.17 (d, J=6.82 Hz, 6 H). MS (ES+) m/e 432 [M+H]+.

Example 107

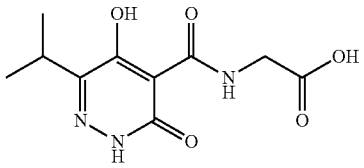

N-{[5-Hydroxy-6-(1-methylethyl)-3-oxo-2,3-dihydro-4-pyridazinyl]carbonyl}glycine To a 100 mL round bottom flask was added ethyl 5-hydroxy-6-(1-methylethyl)-3-oxo-2,3-dihydro-4-pyridazinecarboxylate (example 14(a), 55 mg, 0.243 mmol) and Glycine Sodium Salt (59.0 mg, 0.608 mmol) in 2-methoxyethanol (10 ml) and the mixture was refluxed at 130° C. for 2 hours. The mixture was diluted with water (10 ml) and acidified with 1N HCl. The aqueous solution was then extracted with ethyl acetate (40 mL), organics dried over MgSO4, filtered and solvents removed by evaporation. The crude oil was purified by HPLC chromatography (ODS silica, gradient 25-95% acetonitrile/water (0.1% TFA)) to afford the title compound, N-{[5-hydroxy-6-(1-methylethyl)-3-oxo-2,3-dihydro-4-pyridazinyl]carbonyl}glycine (45 mg, 0.175 mmol, 71.8% yield), as a white solid. 1H NMR (400 MHz, DMSO-$d_6$) d ppm 15.74 (br. s., 1H), 13.07 (s, 1H), 10.19 (t, J=5.68 Hz, 1H), 4.11 (d, J=5.81 Hz, 2H), 3.14 (sept, J=6.82 Hz, 1H), 1.17 (d, J=6.82 Hz, 6H). MS (ES+) m/e 256 [M+H]+.

Example 108

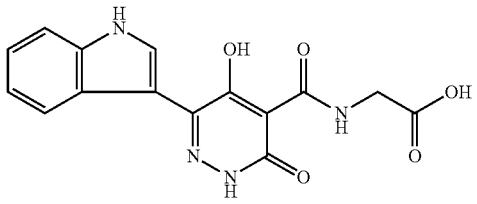

N-{[5-Hydroxy-6-(1H-indol-3-yl)-3-oxo-2,3-dihydro-4-pyridazinyl]carbonyl}glycine To a microwave tube was added ethyl 1H-indol-3-yl(oxo) acetate (1 g, 4.60 mmol) and Ethyl Malonyl hydrazine (0.807 g, 5.52 mmol) in Ethanol (5 ml) and Acetic Acid (0.5 ml). The reaction was irridatiated at 150° C. for 20 minutes. The crude reaction mixture was evaporated down to give a yellow oil.

The crude oil was resuspended in 1,4-Dioxane (20 ml) and DBU (1.041 ml, 6.91 mmol) was added. The solution was irridatiated at 150° C. for 20 minutes, diluted with water (5 ml) and acidified with 6N HCl to cause a precipitate. The orange precipitate was collected by filtration and dried. The precipitate was determined to contain the desired intermediate ester by LCMS and carried on into the next reaction without purification. To a 5 mL microwave tube, a mixture of the crude intermediate ester (50 mg, 0.167 mmol), Glycine Sodium Salt (40.5 mg, 0.418 mmol) and 2-methoxyethanol (2 ml) was refluxed at 150° C. for 20 minutes. The mixture was diluted with water (10 ml) and acidified with 1N HCl. The aqueous solution was then extracted with ethyl acetate (40 mL), organics dried over MgSO4, filtered and solvents removed by evaporation. The crude oil was purified by HPLC chromatography (ODS silica, gradient 10-85% acetonitrile/water (0.1% TFA)) to afford the title compound, N-{[5-hydroxy-6-(1H-indol-3-yl)-3-oxo-2,3-dihydro-4-pyridazinyl]carbonyl}glycine (11 mg, 0.032 mmol, 19.05% yield), as a yellow solid. 1H NMR (400 MHz, DMSO-$d_6$) d ppm 13.23 (s, 1H), 12.99 (br. s., 1H), 11.47-11.77 (m, 1H), 10.22-10.55 (m, 1H), 8.02-8.37 (m, 2H), 7.48 (d, J=8.08 Hz, 1H), 7.17-7.24 (m, 1H), 7.09-7.17 (m, 1H), 4.16 (d, J=5.56 Hz, 2H). MS (ES+) m/e 329 [M+H]+.

Example 109

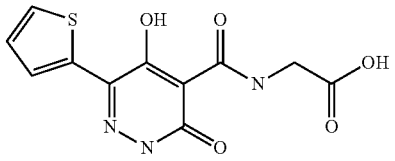

N-{[5-Hydroxy-3-oxo-6-(2-thienyl)-2,3-dihydro-4-pyridazinyl]carbonyl}glycine

109a) Ethyl 3-{(2E)-2-[2-(ethyloxy)-2-oxo-1-(2-thienyl)ethylidene]hydrazino}-3-oxopropanoate. To a microwave tube was added ethyl oxo(2-thienyl)acetate (2 g, 10.86 mmol) and Ethyl Malonyl hydrazine (1.904 g, 13.03 mmol) in Ethanol (5 ml) and Acetic Acid (0.5 ml). The reaction was irridatiated at 150° C. for 20 minutes. The crude reaction mixture was evaporated down to give a yellow oil. The crude oil was purified by flash column chromatography (5%-25% EtOAc: hexanes) to give the product as a clear oil, ethyl 3-{(2E)-2-[2-(ethyloxy)-2-oxo-1-(2-thienyl)ethylidene]hydrazino}-3-oxopropanoate (0.6 g, 1.921 mmol, 17.69% yield). 1H NMR (400 MHz, DMSO-$d_6$) d ppm 11.52 (s, 1H), 7.67 (dd, J=5.05, 1.01 Hz, 1H), 7.39 (dd, J=3.79, 1.01 Hz, 1H), 7.11 (dd, 1H), 4.41 (q, J=7.24 Hz, 2H), 4.11 (q, J=7.24 Hz, 2 H), 3.69 (s, 2H), 1.33 (t, J=7.07 Hz, 3H), 1.19 (t, J=7.07 Hz, 3H). MS (ES+) m/e 313 [M+H]+.

109b) Ethyl 5-hydroxy-3-oxo-6-(2-thienyl)-2,3-dihydro-4-pyridazinecarboxylate. To a microwave tube was added ethyl 3-{(2E)-2-[2-(ethyloxy)-2-oxo-1-(2-thienyl)ethylidene]hydrazino}-3-oxopropanoate (600 mg, 1.921 mmol) and potassium carbonate (133 mg, 0.960 mmol) in Ethanol (2 ml). The reaction was irridatiated at 150° C. for 20 minutes. The crude reaction mixture was diluted with water (10 ml) and acidified with 1N HCl which gave a precipitate. The precipitate was filtered and dried to give the product, ethyl 5-hydroxy-3-oxo-6-(2-thienyl)-2,3-dihydro-4-pyridazinecarboxylate (450 mg, 1.690 mmol, 88% yield) as an off white powder. 1H NMR (400 MHz, DMSO-$d_6$) d ppm 13.02 (s, 1H), 7.83 (dd, J=3.66, 1.14 Hz, 1H), 7.65 (dd, J=5.05, 1.26 Hz, 1H), 7.15 (dd, J=5.05, 3.79 Hz, 1H), 4.31 (q, J=7.07 Hz, 2H), 1.29 (t, J=7.07 Hz, 3H). MS (ES+) m/e 267 [M+H]+.

109c) N-{[5-Hydroxy-3-oxo-6-(2-thienyl)-2,3-dihydro-4-pyridazinyl]carbonyl}glycine. To a 5 mL microwave tube was added ethyl 5-hydroxy-3-oxo-6-(2-thienyl)-2,3-dihydro-4-pyridazinecarboxylate (60 mg, 0.225 mmol) and Glycine Sodium Salt (54.7 mg, 0.563 mmol) in 2-methoxyethanol (2 ml) and the mixture was irradiated at 150° C. for 20 minutes. The mixture was diluted with water (10 ml) and acidified with 1N HCl. The precipitate was collected by filtration and recrystallized in ethanol to afford the title compound, N-{[5-hydroxy-3-oxo-6-(2-thienyl)-2,3-dihydro-4-pyridazinyl]carbonyl}glycine (30 mg, 0.101 mmol, 44.6% yield), as an off white solid. 1H NMR (400 MHz, DMSO-$d_6$) d ppm 13.41 (s, 1H), 13.00 (s, 1H), 10.25 (t, J=5.81 Hz, 1H), 7.79-7.97 (m, 1H), 7.70 (d, J=4.55 Hz, 1H), 7.18 (dd, J=5.05, 3.79 Hz, 1H), 4.16 (d, J=5.81 Hz, 2H). MS (ES+) m/e 296 [M+H]+.

BIOLOGICAL BACKGROUND

The following references set out information about the target enzymes, HIF prolyl hydroxylases, and methods and materials for measuring inhibition of same by small molecules.

M. Hirsilä, P. Koivunen, V. Günzler, K. I. Kivirikko, and J. Myllyharju "Characterization of the Human Prolyl 4-Hydroxylases That Modify the Hypoxia-inducible Factor" J. Biol. Chem., 2003, 278, 30772-30780.

C. Willam, L. G. Nicholls, P. J. Ratcliffe, C. W. Pugh, P. H. Maxwell "The prolyl hydroxylase enzymes that act as oxygen sensors regulating destruction of hypoxia-inducible factor α" Advan. Enzyme Regul., 2004, 44, 75-92

M. S. Wiesener, J. S. Jürgensen, C. Rosenberger, C. K. Scholze, J. H. Hörstrup, C. Warnecke, S. Mandriota, I. Bechmann, U. A. Frei, C. W. Pugh, P. J. Ratcliffe, S. Bachmann, P. H. Maxwell, and K.-U. Eckardt "Widespread hypoxia-inducible expression of HIF-2α in distinct cell populations of different organs" FASEB J, 2003, 17, 271-273.

S. J. Klaus, C. J. Molineaux, T. B. Neff, V. Guenzler-Pukall, I. Lansetmo Parobok, T. W. Seeley, R. C. Stephenson "Use of hypoxia-inducible factor α (HIFα) stabilizers for enhancing erythropoiesis" PCT Int. Appl. (2004), WO 2004108121 A1

C. Warnecke, Z. Zaborowska, J. Kurreck, V. A. Erdmann, U. Frei, M. Wiesener, and K.-U. Eckardt "Differentiating the functional role of hypoxia-inducible factor (HIF)-1α and HIF-2α (EPAS-1) by the use of RNA interference: erythropoietin is a HIF-2α target gene in Hep3B and Kelly cells" FASEB J., 2004, 18, 1462-1464.

For the expression of EGLN3 see:

R. K. Bruick and S. L. McKnight "A Conserved Family of Prolyl-4-Hydroxylases That Modify HIF" Science, 2001, 294, 1337-1340.

For the expression of HIF2α-CODD see:

a) P. Jaakkola, D. R. Mole, Y.-M. Tian, M. I. Wilson, J. Gielbert, S. J. Gaskell, A. von Kriegsheim, H. F. Hebestreit, M. Mukherji, C. J. Schofield, P. H. Maxwell, C. W. Pugh, P, J. Ratcliffe "Targeting of HIF-α to the von Hippel-Lindau Ubiquitylation Complex by $O_2$-Regulated Prolyl Hydroxylation" Science, 2001, 292, 468-472.

b) M. Ivan, K. Kondo, H. Yang, W. Kim, J. Valiando, M. Ohh, A. Salic, J. M. Asara, W. S. Lane, W. G. Kaelin Jr. "HIFα

Targeted for VHL-Mediated Destruction by Proline Hydroxylation: Implications for $O_2$ Sensing" Science, 2001, 292, 464-468.

For the expression of VHL, elongin b and elongin c see:

A. Pause, S. Lee, R. A. Worrell, D. Y. T. Chen, W. H. Burgess, W. M. Linehan, R. D. Klausner "The von Hippel-Lindau tumor-suppressor gene product forms a stable complex with human CUL-2, a member of the Cde53 family of proteins" Proc. Natl. Acad. Sci. USA, 1997, 94, 2156-2161.

Biological Assay(s)

EGLN3 Assay

Materials:

His-MBP-EGLN3 (6HisMBPAttB1EGLN3(1-239)) was expressed in E. Coli and purified from an amylase affinity column. Biotin-VBC [6HisSumoCysVHL(2-213), 6HisSumoElonginB(1-118), and 6HisSumoElonginC(1-112)] and His-GB1-HIF2α-CODD (6HisGB1tevHIF2A (467-572)) were expressed from E. Coli.

Method:

Cy5-labelled HIF2α CODD, and a biotin-labeled VBC complex were used to determine EGLN3 inhibition. EGLN3 hydroxylation of the Cy5CODD substrate results in its recognition by the biotin-VBC. Addition of a Europium/streptavidin (Eu/SA) chelate results in proximity of Eu to Cy5 in the product, allowing for detection by energy transfer. A ratio of Cy5 to Eu emission (LANCE Ratio) is the ultimate readout, as this normalized parameter has significantly less variance than the Cy5 emission alone.

Then 50 nL of inhibitors in DMSO (or DMSO controls) were stamped into a 384-well low volume Corning NBS plate, followed by addition of2.5 μL of enzyme [50 mL buffer (50 mM HEPES/50 mM KCl)+1 mL of a 10 mg/mL BSA in buffer+6.25 μL of a 10 mg/mL $FeCl_2$ solution in water+100 μL of a 200 mM solution of ascorbic acid in water+15.63 μL EGLN3] or control [50 mL buffer+1 mL of a 10 mg/mL BSA in buffer+6.25 μL of a 10 mg/mL $FeCl_2$ solution in water+100 μL of a 200 mM solution of ascorbic acid in water]. Following a 3 minutes incubation, 2.5 μL of substrate [50 mL Buffer+68.6 μL biotin-VBC+70.4 μL Eu (at 710 μg/mL stock)+91.6 μL Cy5CODD+50 μL of a 20 mM solution of 2-oxoglutaric acid in water+0.3 mM CHAPS] was added and incubated for 30 minutes. The plate was loaded into a PerkinElmer Viewlux for imaging. For dose response experiments, normalized data were fit by ABASE/XC50 using the equation y=a+(b−a)/(1+(10ˆx/10ˆc)ˆd), where a is the minimum % activity, b is the maximum % activity, c is the $pIC_{50}$, and d is the Hill slope.

The $IC_{50}$ for exemplified compounds in the EGLN3 assay ranged from approximately 1-3200 nanomolar. This range represents the data accumulated as of the time of the filing of this initial application. Later testing may show variations in $IC_{50}$ data due to variations in reagents, conditions and variations in the method(s) used from those given herein above. So this range is to be viewed as illustrative, and not a absolute set of numbers.

Measure Epo Protein Produced by Hep3B Cell Line Using ELISA Method.

Hep3B cells obtained from the American Type Culture Collection (ATCC) are seeded at 2×10ˆ4 cells/well in Dulbecco's Modified Eagle Medium (DMEM)+10% FBS in 96-well plates. Cells are incubated at 37 deg C./5% CO2/90% humidity (standard cell culture incubation conditions). After overnight adherence, medium is removed and replaced with DMEM without serum containing test compound or DMSO negative control. Following 48 hours incubation, cell culture medium is collected and assayed by ELISA to quantitate Epo protein.

Measure Epo Protein Produced by Hep3B Cell Line Using AlphaLISA Method.

Hep3B cells obtained from the American Type Culture Collection (ATCC) are seeded at 2×10ˆ4 cells/well in Dulbecco's Modified Eagle Medium (DMEM)+10% FBS in 96-well plates. Cells are incubated at 37 deg C./5% CO2/90% humidity (standard cell culture incubation conditions). After overnight adherence, medium is removed and replaced with DMEM with 2% serum containing test compound or DMSO negative control. Following 48 hours incubation, cell culture medium is collected and either frozen for later assay or assayed immediately by AlphaLISA to quantitate Epo protein.

The $EC_{50}$ for exemplar compounds in the Hep3B ELISA and AlphaLISA assay ranged from approximately 0.4-100 micromolar, except example 26, using the reagents and under the conditions outlined herein above. Example 26 has demonstrated an $EC_{50}$ in the Hep3B ELISA assay of greater than 100 micromolar, the maximum concentration tested. This range represents the data accumulated as of the time of the filing of this initial application. Later testing may show variations in $EC_{50}$ data due to variations in reagents, conditions and variations in the method(s) used from those given herein above. So this range is to be viewed as illustrative, and not a absolute set of numbers.

These compound are believed to be useful in therapy as defined above and to not have unacceptable or untoward effects when used in compliance with a permitted therapeutic regime.

The foregoing examples and assay have been set forth to illustrate the invention, not limit it. What is reserved to the inventors is to be determined by reference to the claims.

What is claimed is:

1. A compound which is N-{[2-[(4-bromo-2-fluorophenyl)methyl]-5-hydroxy-6-(1 -methylethyl)-3-oxo-2,3-dihydro-4-pyridazinyl]carbonyl}glycine or a salt thereof.

2. A compound according to claim 1 which is N-{[2-[(4-bromo-2-fluorophenyl)methyl]-5-hydroxy-6-(1-methylethyl)-3-oxo-2,3-dihydro-4-pyridazinyl]carbonyl}glycine.

3. A compound according to claim 1 which is Na, K, Li, Ca, or Mg salt of N-{[2-[(4-bromo-2-fluorophenyl)methyl]-5-hydroxy-6-(1-methylethyl)-3-oxo-2,3-dihydro-4-pyridazinyl]carbonyl}glycine.

[4. A method for treating anemia in a mammal, which method comprises administering an effective amount of N-{[2-[(4-bromo-2-fluorophenyl)methyl]-5-hydroxy-6-(1-methylethyl)-3-oxo-2,3-dihydro-4-pyridazinyl]carbonyl}glycine or a salt thereof to a mammal suffering from anemia which can be treated by inhibiting HIF prolyl hydroxylases.]

5. A pharmaceutical composition comprising N-{[2-[(4-bromo-2-fluorophenyl)methyl]-5-hydroxy-6-(1-methylethyl)-3-oxo-2,3-dihydro-4-pyridazinyl]carbonyl}glycine or a salt thereof and one or more of pharmaceutically acceptable carriers, diluents and excipients.

6. A compound which is N-{[2-[(3,4'-difluoro-4-biphenylyl)methyl]-5-hydroxy-6-(1-methylethyl)-3-oxo-2,3-dihydro-4-pyridazinyl]carbonyl}glycine or a pharmaceutically acceptable salt thereof.

7. A compound according to claim 6 which is N-{[2-[(3,4'-difluoro-4-biphenylyl)methyl]-5-hydroxy-6-(1 -methylethyl)-3-oxo-2,3-dihydro-4-pyridazinyl]carbonyl}glycine.

8. A compound according to claim 6 which is the Na, K, Li, Ca, or Mg salt of N-{[2-[(3,4'-difluoro-4-biphenylyl)methyl]-5-hydroxy-6-(1-methylethyl)-3-oxo-2,3-dihydro-4-pyridazinyl]carbonyl}glycine.

[9. A method for treating anemia in a mammal, which method comprises administering an effective amount of N-{[2-[(3,4'-difluoro-4-biphenylyl)methyl]-5-hydroxy-6-(1-methylethyl)-3-oxo-2,3-dihydro-4-pyridazinyl]carbonyl}glycine or a salt thereof to a mammal suffering from anemia which can be treated by inhibiting HIF prolyl hydroxylases.]

10. A pharmaceutical composition comprising N-{[2-[(3,4'-difluoro-4-biphenylyl)methyl]-5-hydroxy-6-(1 -methylethyl)-3-oxo-2,3-dihydro-4-pyridazinyl]carbonyl}glycine or a salt thereof and one or more of pharmaceutically acceptable carriers, diluents and excipients.

*11. A compound of Formula (I)*

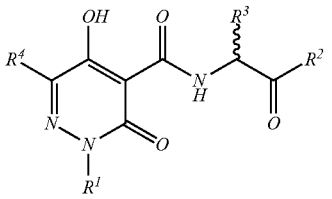

(I)

*wherein*

*$R^1$ is 2-fluoro-4-bromobenzyl, 4-bromobenzyl, 4-(halophenyl)benzyl, 2-fluoro-4-(halophenyl)benzyl, 2-fluoro-4-trifluoromethylbenzyl, 4-trifluoromethylbenzyl, or 2-fluoro-4-($C_1$-$C_4$alkoxyphenyl)benzyl;*

*$R^2$ is OH;*

*$R^3$ is H; and*

*$R^4$ is isopropyl, t-butyl or cyclohexyl; or*

*a pharmaceutically acceptable salt thereof.*

*12. A pharmaceutical composition comprising a compound of claim 11, or a salt thereof and one or more of pharmaceutically acceptable carriers, diluents or excipients.*

*13. The compound:*

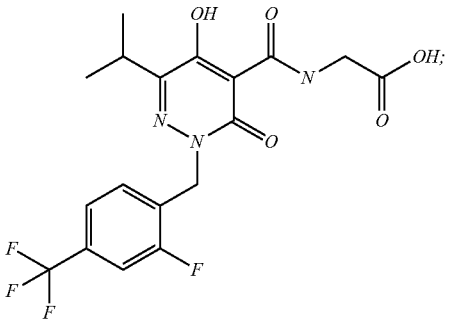

*or a salt thereof.*

*14. The compound:*

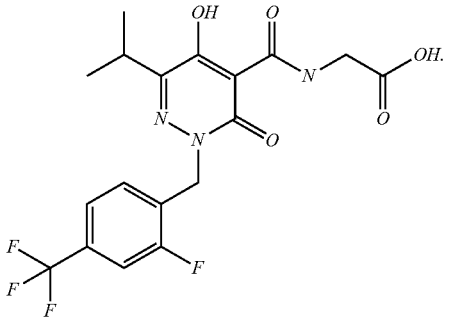

*15. A pharmaceutical composition comprising a compound according to claim 13, and one or more of pharmaceutically acceptable carriers, diluents or excipients.*

*16. The compound:*

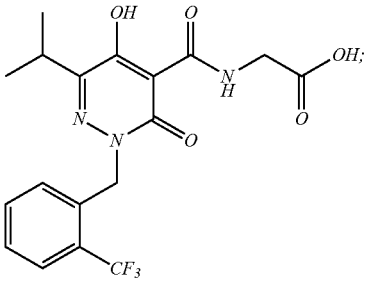

*or a salt thereof.*

*17. The compound:*

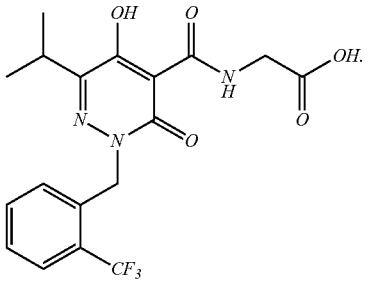

*18. A pharmaceutical composition comprising a compound of claim 16, and one or more of pharmaceutically acceptable carriers, diluents or excipients.*

*19. A method for treating anemia associated with renal disease in a human, said method comprising administering a compound according to claim 13.*

*20. A method for treating anemia associated with renal disease in a human, said method comprising administering a compound according to claim 16.*

*21. A method for treating anemia associated with cancer chemotherapy in a human, said method comprising administering a compound according to claim 13.*

*22. A method for treating anemia associated with cancer chemotherapy in a human, said method comprising administering a compound according to claim 16.*

*23. A method for treating anemia associated with reduced erythropoietin production in a human, said method comprising administering a compound according to claim 13.*

*24. A method for treating anemia associated with reduced erythropoietin production in a human, said method comprising administering a compound according to claim 16.*

*25. A method for increasing erythropoietin production in a human, said method comprising administering a compound according to claim 13.*

*26. A method for increasing erythropoietin production in a human, said method comprising administering a compound according to claim 16.*

* * * * *